US012662663B2

(12) United States Patent
Serero et al.

(10) Patent No.: US 12,662,663 B2
(45) Date of Patent: Jun. 23, 2026

(54) USE OF A DEFICIENT FUSION PROTEIN FOR NUCLEASE ACTIVITY SO AS TO INDUCE MEIOTIC RECOMBINATIONS

(71) Applicants:MEIOGENIX, Paris (FR); INSTITUT CURIE, Paris Cedex (FR); CENTRE NATIONAL DE LA RECHERCHE SCIENTIFIQUE, Paris (FR); SORBONNE UNIVERSITE, Paris (FR)

(72) Inventors: Alexandre Serero, Colombes (FR); Alain Nicolas, Paris (FR)

(73) Assignees: MEIOGENIX, Paris (FR); INSTITUT CURIE, Paris Cedex (FR); CENTRE NATIONAL DE LA RECHERCHE SCIENTIFIQUE, Paris (FR); SORBONNE UNIVERSITE, Paris (FR)

( * ) Notice: Subject to any disclaimer, the term of this patent is extended or adjusted under 35 U.S.C. 154(b) by 682 days.

(21) Appl. No.: 17/926,208

(22) PCT Filed: May 20, 2021

(86) PCT No.: PCT/FR2021/050919
§ 371 (c)(1),
(2) Date: Nov. 18, 2022

(87) PCT Pub. No.: WO2021/234317
PCT Pub. Date: Nov. 25, 2021

(65) Prior Publication Data
US 2023/0174960 A1     Jun. 8, 2023

(30) Foreign Application Priority Data
May 20, 2020    (FR) ...................................... 2005361

(51) Int. Cl.
*C12N 9/22*        (2006.01)
*C12N 9/90*        (2006.01)
*C12N 15/63*       (2006.01)

(52) U.S. Cl.
CPC ................. *C12N 9/22* (2013.01); *C12N 9/90* (2013.01); *C12N 15/63* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 7,273,758 B2 | 9/2007 | Nicolas et al. | |
| 7,279,334 B2 | 10/2007 | Nicolas et al. | |
| 11,248,240 B2 | 2/2022 | Bastianelli et al. | |
| 2004/0033494 A1 | 2/2004 | Nicolas et al. | |
| 2014/0273235 A1 | 9/2014 | Voytas et al. | |
| 2015/0307868 A1 | 10/2015 | Nicolas et al. | |
| 2016/0017393 A1 | 1/2016 | Jacobson et al. | |
| 2018/0023091 A1* | 1/2018 | Bastianelli ......... | C12N 15/8213 435/6.11 |
| 2021/0230619 A1 | 7/2021 | Bastianelli et al. | |
| 2022/0162647 A1 | 5/2022 | Bastianelli et al. | |
| 2024/0263157 A1 | 8/2024 | Serero et al. | |

FOREIGN PATENT DOCUMENTS

| | | | |
|---|---|---|---|
| CA | 2963080 A1 | 4/2016 | |
| FR | 1261456 A | 5/1961 | |
| FR | 2998898 A1 | 6/2014 | |
| WO | WO-2014099744 A1 | 6/2014 | |
| WO | WO-2014104878 A1 | 7/2014 | |
| WO | WO-2016054326 A1 | 4/2016 | |
| WO | WO 2016/120480 | 8/2016 | |
| WO | WO-2016149352 A1 | 9/2016 | |
| WO | WO-2017024047 A1 | 2/2017 | |
| WO | WO-2018197520 A1 | 11/2018 | |
| WO | WO-2019140064 A1 | 7/2019 | |
| WO | WO 2021/234315 | 11/2021 | |

OTHER PUBLICATIONS

Mali et al., Cas9 as a versatile tool for engineering biology. Nature methods (2013), 10: 957-963 (Year: 2013).*
Makarova et al., Evolutionary classification of CRISPR-Cas systems: a burst of class 2 and derived variants. Nature Reviews Microbiology (2020), 18: 67-83 (Year: 2020).*
McGinn et al., Molecular mechanisms of CRISPR-Cas spacer acquisition. Nature Reviews Microbiology (2019), 17:7-12 (Year: 2019).*
Tang et al., Programmable system of Cas13-mediated RNA modification and its biological and biomedical applications. Frontiers in Cell and Developmental Biology (2021), 9: 677587 (Year: 2021).*
He et al., Cas3 protein—a review of a multi-tasking machine. Genes (2020), 11: 208; doi:10.3390/genes11020208 (Year: 2020).*
Sasanuma et al., Meiotic association between Spo11 regulated by Rec102, Rec104 and Rec114. Nucleic Acids Research (2007), 35: 1119-1133 (Year: 2007).*
Laughery et al., R-loop formation by dCas9 is mutagenic in Saccharomyces cerevisiae. Nucleic Acids Research (2019), 47: 2389-2401 (Year: 2019).*
Ran et al., Double nicking by RNA-guided CRISPR Cas9 for enhanced genome editing specificity. Cell (2013), 154: 1380-1389 (Year: 2013).*
Hartung et al., The Catalytically Active Tyrosine Residues of Both SPO11-1 and SPO11-2 Are Required for Meiotic Double-Strand Break Induction in *Arabidopsis*. Plant Cell (2007), 19: 3090-3099 (Year: 2007).*

(Continued)

*Primary Examiner* — Catherine Konopka
(74) *Attorney, Agent, or Firm* — Morrison & Foerster LLP

(57)        ABSTRACT

The present invention relates to a fusion protein comprising a domain of a nuclease from the class II CRISPR system, and a Spo11 domain, wherein both domains of the fusion protein have deficient nuclease activity, as well as the use of this protein to induce targeted meiotic recombinations in a eukaryotic cell.

30 Claims, 1 Drawing Sheet

Specification includes a Sequence Listing.

(56) References Cited

OTHER PUBLICATIONS

Written Opinion in International Application No. PCT/FR2021/050919, Sep. 13, 2021, pp. 1-9.

Sarno, R. et al. "Programming sites of meiotic crossovers using Spo11 fusion proteins" *Nucleic Acids Research,* Aug. 24, 2017, pp. 1-14, vol. 45, No. 19, e164.

Fayos, I et al. "Engineering meiotic recombination pathways in rice" *Plant Biotechnology Journal,* 2019, pp. 2062-2077, vol. 17.

Taagen, E et al. "Counting on Crossovers: Controlled Recombination for Plant Breeding" *Trends in Plant Science,* May 2020, pp. 455-465, vol. 25, No. 5.

Abudayyeh et al., (2016). "C2c2 is a single-component programmable RNA-guided RNA-targeting CRISPR effector," Science, 353(6299):aaf5573, 23 pages.

Acquaviva et al., (2013). "The COMPASS subunit Spp1 links histone methylation to initiation of meiotic recombination," Science, 339:215-8, 7 pages.

Bassett et al., (2014). "CRISPR/Cas9 and genome editing in *Drosophila,*" Journal of Genetics and Genomics, 41:7-19.

Baudat et al., (2000). "Chromosome synapsis defects and sexually dimorphic meiotic progression in mice lacking Spo11," Molecular Cell, 6:989-998.

Baudat et al., (2004). "SPO11: une activite de coupure de l'ADN indispensable a la meiose," Medicine/Sciences, 20:213-218, 13 pages. English translation.

Bergerat et al., (1997). "An atypical topoisomerase II from archaea with implications for meiotic recombination," Nature, 386:414-417.

Blattner, (2015). "TOPO6: a nuclear single-copy gene for plant phylogenetic inference," Plant Syst. Evol., 302:239-244, 6 pages.

Bowles et al., (2006). "Retinoid signaling determines germ cell fate in mice," Science, 312(5773):596-600.

Broothaerts et al., (2005). "Gene transfer to plants by diverse species of bacteria," Nature, 433:629-633.

Care et al., (1999). "The MET3 promoter: a new tool for Candida albicans molecular genetics," Molecular Microb, 34:792-798.

Carlile et al., (2008). "Meiosis I is established through division-specific translational control of a cyclin," Cell, 133:280-91.

Carroll, (2012). "A CRISPR approach to gene targeting," Molecular Therapy, 20(9):1658-1660.

Cho et al., (2000). "High-efficiency induction of soybean hairy roots and propagation of the soybean cyst nematode," Planta, 210:195-204.

Clough et al., (1998). "Floral dip: a simplified method for Agrobacterium-mediated transformation of *Arabidopsis thaliana,*" Plant J., 16(6):735-43.

Da Ines et al., (2013). "Meiotic recombination in *Arabidopsis* is catalysed by DMC1, with RAD51 playing a supporting role," PLoS Genet, 9:e1003787, 11 pages.

Ding et al., (2016). "Recent advances in genome editing using CRISPR/Cas9," Frontiers in Plant Science, 7:703, 12 pages.

Egholm et al., (1992). "Peptide nucleic acids (PNA)—Oligonucleotide analogues with an achiral peptide backbone," J. Am. Chem. Soc., 114:1895-1897.

Eid et al., (2016). "High efficiency of targeted mutagenesis in arabidopsis via meiotic promoter-driven expression of Cas9 endonuclease," Plant Cell Rep, 35(7):1555-8, 4 pages.

Esposito et al., (1974). "Genetic Recombination and Commitment to Meiosis in *Saccharomyces,*" PNAS, 71:3172-3176.

Fraley et al., (1986). "Genetic transformation in higher plants," Crit. Rev. Plant. Sci., 4(1):1-46.

Fromm et al., (1985). "Expression of genes transferred into monocot and dicot plant cells by electroporation," PNAS USA, 82:5824-8.

Fromm et al., (1990). "Inheritance and expression of chimeric genes in the progeny of transgenic maize plants," Biotechnology, 8:833-839.

Gao et al., (2017). "Engineered Cpf1 variants with altered PAM specificities," Nat Biotechnol., 35(8):789-792, 15 pages.

Gelvin, (2005). "Viral-mediated plant transformation gets a boost," Nature Biotechnology, 23:684-685.

Grelon et al., (2001). "AtSPO11-1 is necessary for efficient meiotic recombination in plants," Embo J., 20:589-600.

Griesbach, (1987). "Chromosome-mediated transformation via microinjection," Plant Sci., 50:69-77.

Honigberg et al., (1994). "Reversal of cell determination in yeast meiosis: Postcommitment arrest allows return to mitotic growth," PNAS USA, 91:6559-6563.

Hunter et al., (2003). "Synaptonemal complexities and commonalities," Molecular Cell, 12:533-535.

Jinek et al., (2012). "A programmable dual-RNA-guided DNA endonuclease in adaptive bacterial immunity," Science, 337:816-821.

Jinek et al., (2012). "A Programmable Dual-RNA-Guided DNA Endonuclease in Adaptive Bacterial Immunity" Science, Supplementary Materials Only, 37 pages.

Kasama et al., (2006). "Spo5/Mug12, a Putative Meiosis-Specific RNA-Binding Protein, Is Essential for Meiotic Progression and Forms Mei2 Dot-Like Nuclear Foci," Eukaryotic Cell, 5(8):1301-1313.

Kassir et al., (1991). "Monitoring meiosis and sporulation in *Saccharomyces cerevisiae,*" Meth. Enzymol., 194:94-110.

Keeney, (2001). "Mechanism and control of meiotic recombination initiation," Curr. Top. Dev. Biol, 52:1-53.

Kisselev, (2002). "Polypeptide release factors in prokaryotes and eukaryotes: same function, different structure," Structure, 10:8-9.

Klein et al., (1987). "High-velocity microprojectiles for delivering nucleic acids into living cells," Nature, 327:70-73.

Lam et al., (2014). "Mechanism and Regulation of Meiotic Recombination Initiation," Cold Spring Harb Perspect in Biol, 7(1):a016634, 24 pages.

Lee et al., (2008). "T-DNA Binary Vectors and Systems," Plant Physiology, 146(2):325-332.

Li et al., (2006). "Double-stranded DNA breaks and gene functions in recombination in meiosis," Cell Research, 16:402-412.

Li et al., (2012). "Characterization of a set of novel meiotically-active promoters in Arabidopsis," BMC Plant Biol., 12:104, 12 pages.

Li et al., (2013). "Heritable gene targeting in the mouse and rat using a CRISPR-Cas system," Nature Biotechnology, 31(8):681-683.

Liti et al., (2012). "Advances in quantitative trait analysis in yeast," PLoS Genetics, 8(8):e1002912, 7 pages.

Ma et al., (2015). "A Robust CRISPR/Cas9 System for Convenient, High-Efficiency Multiplex Genome Editing in Monocot and Dicot Plants," Molecular Plant, 8(8):1274-1284.

MacGregor et al., (2019). "Large-scale chromatin organisation in interphase, mitosis and meiosis," Biochemical Journal, 476:2141-2156, 23 pages.

Makarova et al., (2011). "Evolution and classification of the CRISPR-Cas systems," Nat. Rev. Microbiol., 9:467-477, 23 pages.

Malkova et al., (1996). "Meiotic Recombination Initiated by a Double-Strand Break in rad50Δ Yeast Cells Otherwise Unable to Initiate Meiotic Recombination," Genetics, 143:741-754.

McKim et al., (1998). "mei-W68 in *Drosophila melanogaster* encodes a Spo11 homolog: evidence that the mechanism for initiating meiotic recombination is conserved," Genes Dev, 12(18):2932-42.

Miao et al., (2019). "Systematically investigating the key features of the DNase deactivated Cpf1 for tunable transcription regulation in prokaryotic cells," Synthetic and Systems Biotechnology 4:1-9.

Milo et al. "What are the concentrations of different ions in cells?" http://book.bionumbers.org/what-are-the-concentrations-of-different-ions-in-cells, on Dec. 20, 2016 from the online version of Cell Biology by the Numbers, published Dec. 7, 2015. 4 pages.

Morrill et al., (1984). "Role of calcium in regulating intracellular pH following the stepwise release of the metabolic blocks at first-meiotic prophase and second-meiotic metaphase in amphibian oocytes," Biochimica et Biophysica Acta, 804:107-117.

Murakami et al., (2009). "Gel electrophoresis assays for analyzing DNA double-strand breaks in *Saccharomyces cerevisiae* at various spatial resolutions," Methods Mol Biol, 557:117-142, 25 pages.

(56) References Cited

OTHER PUBLICATIONS

Murakami et al., (2009). "Locally, meiotic double-strand breaks targeted by Gal4BD-Spo11 occur at discrete sites with a sequence preference," Mol. Cell. Biol, 29:3500-16.

Nishimasu et al., (2014). "Crystal structure of Cas9 in complex with guide RNA and target DNA," Cell, 156:935-949.

OriGene, (2014). "In Vitro digestion of DNA with Cas9 nuclease and sgRNA," available online at <https://cdn.origene.com/assets/documents/protein/In%20vitro%20digestion%20with%20Cas9%20nuclease%20and%20sgRNA.pdf>, 2 pages.

Panizza et al., (2011). "Spo11-Accessory Proteins Link Double-Strand Break Sites to the Chromosome Axis in Early Meiotic Recombination," Cell, 146:372-383.

Pecina et al., (2002). "Targeted Stimulation of Meiotic Recombination," Cell, 111:173-184.

Robert et al., (2016). "The TopoVIB-Like protein family is required for meiotic DNA double-strand break formation," Science, 351(6276):943-949.

Ronspies et al., (2021). "CRISPR-Cas-mediated chromosome engineering for crop improvement and synthetic biology," Nature Plants, 7(5):566-573.

Sadowski et al., (2009). "The sequence-structure relationship and protein function prediction," Current Opinion in Structural Biology, 19:357-362.

Safari et al., (2019). "CRISPR Cpf1 proteins: structure, function and implications for genome editing," Cell Biosci, 9:36, 21 pages.

Scott et al., (2014). "Targeted genome regulation and modification using transcription activator-like effectors," FEBS J, 281(20):4583-97.

Seffernick et al., (2001). "Melamine deaminase and atrazine chlorohydrolase: 98 percent identical but functionally different," J. Bacterial., 183(8):2405-2410.

Shao et al., (2017). "Enhancing CRISPR/Cas9-mediated homology-directed repair in mammalian cells by expressing *Saccharomyces cerevisiae* Rad52," International Journal of Biochemistry and Cell Biology, 92:43-52.

Sherman et al., (1963). "Evidence for Two Types of Allelic Recombination in Yeast," Genetics, 48:255-261.

Sherman, (1991). "Getting started with yeast," Meth. Enzymol., 194:3-21.

Shingu et al., (2012). "The double-stranded break-forming activity of plant SPO11s and a novel rice SPO11 revealed by a *Drosophila* bioassay," BMC Mol Biol, 13:1, 16 pages.

Shmakov et al., (2015). "Discovery and Functional Characterization of Diverse Class 2 CRISPR-Cas Systems," Molecular Cell, 60(3):385-397.

Singh et al., (2018). "Protein Engineering Approaches in the Post-Genomic Era," Current Protein and Peptide Science, 19(1):5-15.

Smith et al., (1998). "Recombination at work for meiosis," Curr. Opin. Genet. Dev, 8:200-211.

Sood et al., (2011). "Problems and possibilities of monocot transformation," Biologia Plantarum, 55:1-15.

Sprink et al., (2014). "The splicing fate of plant SPO11 genes," Frontiers in Plant Science, 5:214, 9 pages.

Sun et al., (2014). "Reconstitution of gametogenesis in vitro: Meiosis is the biggest obstacle," Journal of Genetics and Genomics, 41:87-95.

Tang et al., (2013). "Identification of Dehalobacter reductive dehalogenases that catalyse dechlorination of chloroform, 1,1,1-trichloroethane and 1,1-dichloroethane," Phil Trans R Soc B, 368:20120318, 10 pages.

Tang et al., (2019). "Methods for Enhancing Clustered Regularly Interspaced Short Palindromic Repeats/Cas9-Mediated Homology-Directed Repair Efficiency," Frontiers in Genetics, 10:551, 9 pages.

Valton et al. (2012). "5'-Cytosine-Phosphoguanine (CpG) Methylation Impacts the Activity of Natural and Engineered Meganucleases" The Journal Of Biological Chemistry, 287(36):30139-30150.

Wan et al., (1994). "Generation of Large Nos. of Independently Transformed Fertile Barley Plants," Plant Physiol., 104:37-48.

Whisstock et al., (2003). "Prediction of protein function from protein sequence and structure," Q Rev Biophys, 36(3):307-340.

Witkowski et al., (1999). "Conversion of a beta-ketoacyl synthase to a malonyl decarboxylase by replacement of the active-site cysteine with glutamine," Biochemistry, 38(36):11643-50.

Wu et al., (1994). "Meiosis-Induced Double-Strand Break Sites Determined by Yeast Chromatin Structure," Science, 263:515-518.

Xu et al., (2018). "The Application of a Meiocyte-Specific CRISPR/Cas9 (MSC) System and a Suicide-MSC System in Generating Inheritable and Stable Mutations in *Arabidopsis*," Front. Plant Sci., 9:1007, 12 pages.

Yelina et al., (2022). "Coexpression of MEIOTIC-TOPOISOMERASE VIB-dCas9 with guide RNAs specific to a recombination hotspot is insufficient to increase crossover frequency in *Arabidopsis*," G3, 12(7):jkac105, 12 pages.

Yu et al., (2010). "OsSPO11-1 is essential for both homologous chromosome pairing and crossover formation in rice," Chromosoma, 119:625-636.

Zale et al., (2009). "Evidence for stable transformation of wheat by floral dip in Agrobacterium tumefaciens," Plant Cell Reports, 28:903-913.

Zenvirth et al., (1997). "Switching yeast from meiosis to mitosis: double-strand break repair, recombination and synaptonemal complex," Genes to Cells, 2:487-498.

Zetsche et al., (2015). "Cpf1 is a single RNA-guided endonuclease of a class 2 CRISPR-Cas system," Cell, 163:759-771.

Dicarlo et al., (2013). "Genome engineering in Saccharomyces cerevisiae using CRISPR-Cas systems," Nucleic Acids Research, 41(7):4336-4343.

Weitzel et al., (2021). "Meiotic Cas9 expression mediates gene conversion in the male and female mouse germline," PLoS Biol, 19(12):e3001478, 16 pages.

Yelina et al., (2021). "CRISPR targeting of MEIOTIC-TOPOISOMERASE VIB-dCas9 to a recombination hotspot is insufficient to increase crossover frequency in *Arabidopsis*," bioRxiv, available online at <https://www.biorxiv.org/content/10.1101/2021.02.01.429210v1>, 42 pages.

* cited by examiner

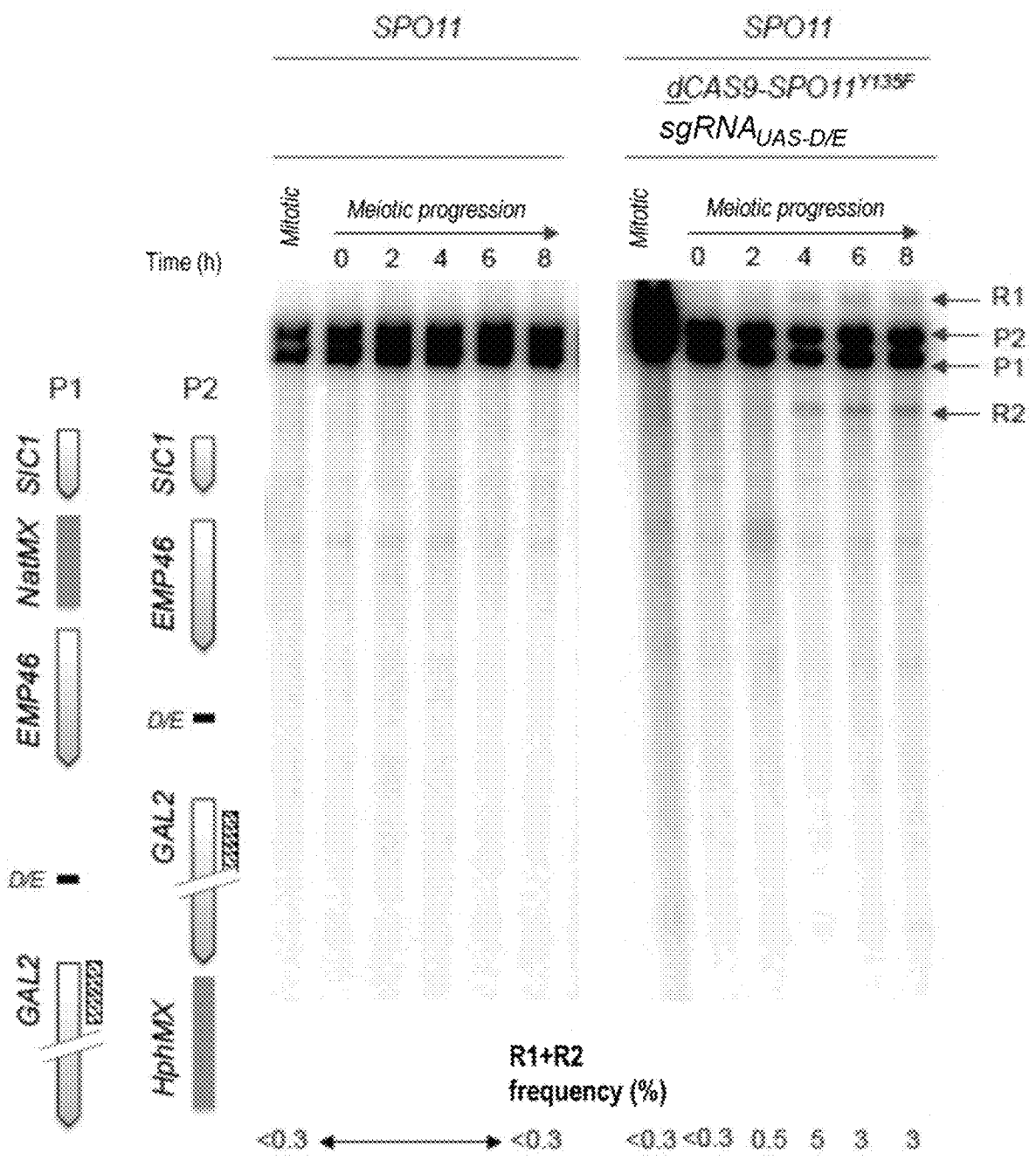

USE OF A DEFICIENT FUSION PROTEIN FOR NUCLEASE ACTIVITY SO AS TO INDUCE MEIOTIC RECOMBINATIONS

CROSS-REFERENCE TO RELATED APPLICATION

This application is the U.S. national stage application of International Patent Application No. PCT/FR2021/050919, filed May 20, 2021.

REFERENCE TO SEQUENCE LISTING

The Sequence Listing for this application is labeled "Seq-List-replace.txt" which was created on Dec. 7, 2022 and is 342,419 bytes. The entire content of the sequence listing is incorporated herein by reference in its entirety.

TECHNICAL FIELD

The present invention pertains to the field of targeted genetic modifications in eukaryotes. It relates in particular to a process for modifying a eukaryotic cell by inducing targeted meiotic recombinations.

TECHNOLOGICAL BACKGROUND OF THE INVENTION

The modification of the genetic material of eukaryotic organisms has developed greatly in the past twenty years, and has found application in the field of plants, human and animal cells as well as microorganisms such as yeast for applications in the fields of agriculture, human health, agri-food and environmental protection.

Yeasts find their application in a wide variety of industrial fields. Because many species are harmless, yeasts are in particular used in the food industry as fermentation agent in baking, brewing, wine-making or distilling, or in the form of extracts as nutritional elements or flavoring agents. They can also find use in the industrial production of bioethanol or molecules of interest such as vitamins, antibiotics, vaccines, enzymes, or steroid hormones, or in processes for degrading cellulosic materials. Similarly, plants are used in many industrial fields, whether in the agri-food, cosmetic or pharmaceutical industries.

The diversity of industrial applications of yeast and plants implies that there is a constant demand for yeast strains and plant varieties with improved traits or, at least, adapted to a new use or new culture conditions. In order to obtain a eukaryotic cell or organism with a particular trait, the person skilled in the art can use sexual reproduction and select a hybrid cell or organism providing the desired combination of parental traits. This method is however random and the selection step can lead to significant delays, in particular in the case of yeasts and plants.

Alternatively, the skilled person can also modify the genetic heritage of a cell or an organism by a recombinant DNA technique. This modification can nevertheless constitute an impediment to its exploitation, whether for regulatory, sanitary or environmental reasons, in particular in the case of plants considered as genetically modified organisms (GMO).

A third alternative consists in causing a reassortment of alleles of paternal and maternal origin in the genome, during meiotic recombination. Meiotic recombination is an exchange of DNA between homologous chromosomes during meiosis. After DNA replication, recombination is initiated by the formation of double-strand breaks in one (or the other) of the chromatids of the homologous chromosomes, followed by the repair of these breaks, using a chromatid of the homologous chromosome as a template. However, meiotic recombinations have the disadvantage of being non-uniform. Indeed, the double-strand break sites at the origin of these recombinations are not distributed homogeneously in the genome. A distinction can thus be made between so-called 'hot' chromosomal regions where the frequency of recombination is high, and so-called 'cold' chromosomal regions where the frequency of recombination can be up to 100 times lower.

Spo11 is the protein that catalyzes double-strand breaks during meiosis. It acts in dimer form in cooperation with other partner proteins. At present, the factors determining the choice of double-strand break sites by Spo11 and its partners remain poorly understood.

The control of double-strand break formation and, hence, of meiotic recombinations, is crucial for the development of genetic engineering techniques. In particular, it has been shown that it is possible to modify the double-strand break formation sites by fusing Spo11 with the DNA-binding domain of the transcriptional activator Gal4 (Pecina et al., 2002 Cell, 111, pp. 173-184). The Gal4BD-Spo11 and Gal4-Spo11 fusion proteins allow the introduction of double-strand breaks in so-called 'cold' chromosomal regions, at the level of Gal4 DNA binding sites. However, according to the Spo11-Gal4 system, the introduction of targeted double-strand breaks is conditioned by the presence of Gal4 binding sites, making it impossible to induce targeted meiotic recombination phenomena independently of specific binding sites. Local stimulation of meiotic recombination at a number of chromosomal sites has also been reported using a fusion protein comprising a Spo11 domain and a Cas9 domain and in which the nuclease activity is carried by either of these domains (international patent application WO 2016/120480).

Thus, there remains a need to provide methods that allow easy and specific induction of meiotic recombination of genomic regions inaccessible to prior art techniques and that can be applied to a wide range of eukaryotic cells.

SUMMARY OF THE INVENTION

The objective of the present invention is to propose a fusion protein as well as a process for inducing targeted meiotic recombinations in eukaryotic cells, preferably yeast or plant cells, in any region of the genome, preferably several different regions of the genome, independently of any known binding site, and in particular in so-called 'cold' chromosomal regions.

Thus, according to a first aspect, the present invention relates to a fusion protein comprising (i) a variant of a nuclease associated with a CRISPR system, preferably a class 2 CRISPR system, and (ii) a variant of a Spo11 protein, wherein the variants of the nuclease associated with the CRISPR system and of the Spo11 protein have a deficient nuclease activity.

In particular, the nuclease associated with a CRISPR system is a nuclease of class II and type II, V or VI, preferably type II. Preferably, the nuclease is a CRISPR system-associated nuclease selected from the group consisting of Cas1, Cas2, Cas9, Csn2, Cas13, C13a (C2c2), C13b, C13c, Cas12, C12a (Cpf1), C2c1 and C2c3.

Said fusion protein may comprise in particular a variant of a Spo11 protein devoid of nuclease activity and/or a variant of a Cas9 nuclease devoid of nuclease activity. Preferably, the fusion protein comprises a variant of a Spo11 protein devoid of nuclease activity and a variant of a Cas9 nuclease devoid of nuclease activity.

The variant of a nuclease associated with a CRISPR system preferably has at least 80%, 85%, 90%, 95%, 96%, 97%, 98%, or 99% identity with said nuclease. The variant preferably also exhibits reduced nuclease activity, preferably reduced by at least 50%, relative to the nuclease activity of the wild-type protein, and preferably is devoid of nuclease activity, and is capable of interacting with a guide RNA.

In particular, the variant of a nuclease associated with a CRISPR system may be a variant of a Cas9 nuclease comprising a sequence having at least 80, 85, 90, 95, 96, 97, 98, or 99% identity with said Cas9 protein and in which the residue corresponding to the aspartate at position 10 of SEQ ID NO: 38 and/or the residue corresponding to the histidine at position 840 of SEQ ID NO: 38 have been substituted, preferably by alanines. More particularly this variant may be a variant of a Cas9 protein comprising a sequence having at least 80, 85, 90, 95, 96, 97, 98, or 99% identity with one of the sequences SEQ ID NO: 38 to 43, and in which the residue corresponding to the aspartate at position 10 of SEQ ID NO: 38 and/or the residue corresponding to the histidine at position 840 of SEQ ID NO: 38 have been substituted, preferably by alanines.

The variant of a Spo11 protein preferably has at least 80%, 85%, 90%, 95%, 96%, 97%, 98%, or 99% identity with said protein.

The variant of a Spo11 protein preferably exhibits reduced nuclease activity, reduced by at least 50% relative to the nuclease activity of the wild-type protein, and preferably is devoid of nuclease activity.

In particular, the variant of a Spo11 protein may be a variant of a Spo11 protein having at least 80%, 85%, 90%, 95%, 96%, 97%, 98%, or 99% identity with said Spo11 protein and in which the residue corresponding to the tyrosine at position 135 of SEQ ID NO: 1 is substituted, preferably by a phenylalanine. More particularly this variant may be a variant of a Spo11 protein comprising a sequence having at least 80, 85, 90, 95, 96, 97, 98, or 99% identity with one of the sequences SEQ ID NO: 1 and 10 to 21 and 46-48, and in which the residue corresponding to the tyrosine at position 135 of SEQ ID NO: 1 is substituted, preferably by a phenylalanine.

According to a second aspect, the present invention relates to a nucleic acid encoding the fusion protein defined above.

According to a third aspect, the present invention also relates to an expression cassette or vector comprising a nucleic acid as defined above.

According to a fourth aspect, the present invention also relates to a host cell, preferably non-human, comprising a fusion protein, a nucleic acid, a cassette or a vector as defined above.

Preferably, the host cell is a eukaryotic cell, even more preferably a yeast, plant, fungus or animal cell, and most preferably, the host cell is a plant cell or a yeast cell. In particular, the host cell is a plant cell, the plant preferably being of agronomic, horticultural, pharmaceutical or cosmetic interest, in particular vegetables, fruits, herbs, flowers, trees and shrubs.

The plant cell is preferably selected from monocotyledonous plants and dicotyledonous plants, more particularly preferably selected from the group consisting of rice, wheat, soybean, corn, tomato, onion, cucumber, lettuce, asparagus, carrot, turnip, *Arabidopsis thaliana*, barley, rapeseed, cotton, grapevine, sugar cane, beet, cotton, sunflower, oil palm, coffee, tea, cocoa, chicory, bell pepper, chili, lemon, orange, nectarine, mango, apple, banana, peach, apricot, sweet potato, yam, almond, hazelnut, strawberry, melon, watermelon, olive tree, potato, zucchini, eggplant, avocado, cabbage, plum, cherry, pineapple, spinach, apple, mandarin, grapefruit, pear, grape, clove, cashew nut, coconut, sesame, rye, hemp, tobacco, berries such as raspberry or blackcurrant, peanut, castor, vanilla, poplar, eucalyptus, green foxtail, casava, and horticultural plants such as, for example, roses, tulips, orchids and geraniums. In particular, the plant cell may be selected from the group consisting of rice, wheat, soybean, corn, tomato, onion, cucumber, lettuce, asparagus, carrot, turnip, *Arabidopsis thaliana*, barley, rapeseed, cotton, grapevine, sugar cane, beet, cotton, sunflower, palm olive tree, coffee, tea, cocoa, chicory, bell pepper, chili, lemon, orange, nectarine, mango, apple, banana, peach, apricot, sweet potato, yam, almond, hazelnut, strawberry, melon, watermelon, olive tree, and horticultural plants such as roses, tulips, orchids and geraniums. Preferably, the plant cell is selected from the group consisting of rice, wheat, soybean, and corn.

According to a fifth aspect, the invention relates to a process for inducing targeted meiotic recombinations in a eukaryotic cell, preferably non-human, comprising introduction into said cell of:

a) a fusion protein, a nucleic acid, an expression cassette, or a vector as described above; and b) one or more guide RNAs or one or more nucleic acids encoding said guide RNAs, said guide RNAs comprising a nuclease binding RNA structure associated with a CRISPR system of the fusion protein and a sequence complementary to the targeted chromosomal region; and induction of entry into prophase I of meiosis of said cell.

The present invention further relates, in a sixth aspect, to a process for generating variants of a eukaryotic organism, preferably non-human, comprising:

introduction into a cell of said organism of:

a) a fusion protein, a nucleic acid, an expression cassette, or a vector as described above; and b) one or more guide RNAs or one or more nucleic acids encoding said guide RNAs, said guide RNAs comprising a nuclease binding RNA structure associated with a CRISPR system of the fusion protein and a sequence complementary to the targeted chromosomal region; and induction of entry into prophase I of meiosis of said cell;

obtaining cell(s) with the desired recombination(s) in the targeted chromosomal region(s); and genesis of a variant of the organism from said recombinant cell.

In a seventh aspect, the present invention also relates to a process for identifying or locating genetic information encoding a trait of interest in a eukaryotic cell genome, preferably non-human, comprising:

introduction into the eukaryotic cell of:

a) a fusion protein, a nucleic acid, an expression cassette, or a vector as described above; and b) one or more guide RNAs or one or more nucleic acids encoding said guide RNAs, said guide RNAs comprising a nuclease binding RNA structure associated with a CRISPR system of the fusion protein and a sequence complementary to the targeted chromosomal region; and induction of entry into prophase I of meiosis of said cell;

obtaining cell(s) with the desired recombination(s) in the targeted chromosomal region(s); and analysis of the genotypes and phenotypes of the recombinant cells in order to identify or locate the genetic information encoding the trait of interest.

Preferably, the trait of interest is a quantitative trait of interest (QTL).

In an eighth aspect, the present invention finally relates to the use of a fusion protein, a nucleic acid, an expression cassette or a vector to (i) induce targeted meiotic recombinations in a eukaryotic cell, preferably non-human, (ii) generate variants of a eukaryotic organism, preferably non-human, and/or (iii) identify or locate genetic information encoding a trait of interest in a eukaryotic cell genome, preferably non-human.

Preferably, in the processes or uses according to the invention, the eukaryotic cell is a yeast cell, a plant cell, a fungal cell or an animal cell, preferably a yeast cell, a plant cell or a fungal cell.

BRIEF DESCRIPTION OF THE DRAWINGS

FIG. 1 illustrates the formation of recombinant molecules in the GAL2 locus region induced by the dCas9-Spo11$^{Y133F}$ fusion protein.

DETAILED DESCRIPTION OF THE INVENTION

The clustered regularly interspaced short palindromic repeats (CRISPR) system is a defense system demonstrated in bacteria and archaea against foreign DNA. These short fragments corresponding to the infectious agent are inserted into a series of CRISPR repeats and are used as CRISPR guide RNA (crRNA) to target the infectious agent in subsequent infections. This system is essentially based on the association of a CRISPR-associated (Cas) endonuclease protein and a 'guide' RNA (gRNA or sgRNA) responsible for the specificity of the cleavage site. It allows DNA double-strand breaks (DSBs) to be made at the sites targeted by the CRISPR system.

There are five main types of CRISPR systems that differ in the repertoires of CRISPR-associated genes, the organization of Cas operons and the structure of repeats within CRISPR arrays. These five types of systems have been divided into two classes: class I comprising types I, III and IV that use a multimeric crRNA effector module and class II comprising types II, V and VI that use a monomeric crRNA effector module.

Class II and type II CRISPR systems, predominantly represented by the Cas9 and Csn2 nucleases, comprise a small trans-acting crRNA (tracrRNA) that pairs with each pre-CRISPR RNA (crRNA) repeat to form a double-stranded RNA [tracrRNA:crRNA] cleaved by RNase III in the presence of the endonuclease.

Class II and type VI CRISPR systems are represented by the C13a (previously known as C2c2), C13b, and C13c proteins. The CRISPR-C13 system was discovered in the bacterium *Leptotrichia shahii* (Abudayyeh et al., *Science* 2016; 353(6299): aaf5573) and is analogous to the CRISPR-Cas9 system. However, unlike Cas9, which targets DNA, the C13 proteins target and cleave single-stranded RNA.

Class II and type V CRISPR-Cas systems are, among others, represented by the nuclease Cpf1 (also called Cas12a) recently discovered in the bacterium *Francisella novicida* (Zetsche B, Cell 2015, 163: pp. 759-771), and the nucleases C2c1 (also called Cas12b) and C2c3 identified in *Alicyclobacillus acidoterrestris* (Shmakov et al., 2015 Molecular Cell, 60, pp. 385-397). Cpf1 contains a mixed alpha/beta domain, a RuvC-I domain followed by a helical region, a RuvC-II domain and a zinc-finger domain. A functional CRISPR-Cpf1 system does not require a tracrRNA but only a crRNA. In particular, a 42-44 nucleotide crRNA with a direct repeat sequence of about 19 nucleotides followed by a 23-25 nucleotide protospacer sequence is sufficient to guide the Cpf1 endonuclease to the target nucleic acid.

The Cpf1-crRNA complex cleaves target DNA or RNA by identifying a 5'-YTN-3' or 5'-TTTN-3' PAM motif adjacent to the proto-spacer (where 'Y' is a pyrimidine and 'N' is any nucleobase), as opposed to the guanine-rich PAM motif (5'-NGG-3') targeted by Cas9. Recognition of a thymidine-rich PAM extends the number of sites targeted by the CRISPR technique to A-T rich regions devoid of PAM motifs and allows its use in cells with a G-rich genome, thus limiting the occurrence of a specific targeting or 'off-targets'.

The inventors have demonstrated that it is possible to modify the CRISPR system in order to induce targeted meiotic recombinations in a eukaryotic cell, and in particular in a yeast or a plant cell, even though the fusion protein comprises two domains deficient in nuclease activity. They have indeed shown that the combined expression of a fusion protein comprising a CRISPR/Cas domain and a Spo11 domain and a guide RNA allowed, surprisingly, the induction of targeted meiotic recombination through double-strand breaks during prophase I of meiosis and the repair of these breaks, even though both domains of the fusion protein are deficient in nuclease activity. This system has never been used to target meiotic recombination sites in any organism.

Thus, according to a first aspect the present invention relates to a fusion protein comprising (i) a nuclease associated with a CRISPR system, preferably a class II CRISPR system, preferably a class II and type II CRISPR system, and (ii) a Spo11 protein, wherein the nuclease associated with the CRISPR system and the Spo11 protein have deficient nuclease activity. The fusion protein according to the invention comprises (i) a domain comprising a Spo11 protein (Spo11 domain) having deficient nuclease activity and (ii) a domain comprising a nuclease associated with a CRISPR system (CRISPR domain) having deficient nuclease activity.

Preferably, the fusion protein of the present invention comprises a CRISPR domain comprising a variant of a CRISPR system-associated nuclease exhibiting deficient nuclease activity, and a Spo11 domain comprising a variant of a Spo11 protein having deficient nuclease activity.

As used herein, the term 'nuclease activity' refers to the enzymatic activity of an endonuclease that has an active site for creating breaks or cuts within DNA or RNA chains, preferably DNA double-strand breaks. 'Deficient nuclease activity' of a protein means in particular a reduced, diminished or non-existent nuclease activity, in particular relative to the nuclease activity of the wild-type protein from which the variant is derived. Preferably, the nuclease activity of the protein is reduced by at least 50, 55, 60, 65, 70, 75, 80, 85, 90, 95 or 100%, relative to the nuclease activity of the wild-type protein. With particular preference the Spo11 domain and the CRISPR domain are devoid of nuclease activity, in particular of endonuclease DNA activity. They are therefore incapable of generating double-strand breaks. The ability of a protein to induce breaks within DNA chains (endonuclease DNA activity), in particular double-strand breaks, may easily be tested by the person skilled in the art by way of conventional techniques, for example by Southern blot or by sequencing of the oligonucleotides associated with Spo11.

As used herein, the term 'fusion protein' refers to a chimeric protein comprising at least two domains derived from the combination of different proteins or protein fragments. The nucleic acid encoding this protein is obtained by juxtaposing the regions encoding the proteins or protein fragments in such a way that they are in phase and transcribed on the same mRNA. The different domains of the fusion protein can be directly adjacent or separated by linker sequences that introduce a certain structural flexibility into the construct. The fusion protein according to the present invention comprises a first domain which is a variant of a nuclease associated with a CRISPR system and a second domain which is a variant of a Spo11 protein, said variants having nuclease activity that is deficient relative to the parent protein, preferably being devoid of nuclease activity, in particular endonuclease DNA activity. Preferably, the variants have at least 80%, 85%, 90%, 95%, 96%, 97%, 98%, or 99% identity with the parent nuclease.

Spo11 is a protein related to the catalytic subunit A of a type II topoisomerase found in archaea (Bergerat et al., Nature, 386, pp. 414-7). It catalyzes DNA double-strand breaks that initiate meiotic recombination. It is a highly evolutionarily conserved protein for which homologues exist in all eukaryotes. Spo11 is active as a dimer formed by two subunits, each of which cleaves a strand of DNA. Although essential, Spo11 does not act alone to generate double-strand breaks during meiosis. In the yeast *S. cerevisiae*, for example, it cooperates with the proteins, Rec102, MTOPVIB/TOPOVIB, Rec103/Sk18, Rec104, Rec114, Mer1, Mer2/Rec107, Mei4, Mre2/Nan8, Mre11, Rad50, Xrs2/Nbs1, Hop1, Red1, Mek1, Set1, and Spp1 as described in the papers by Keeney et al. (2001 Curr. Top. Dev. Biol, 52, pp. 1-53), Smith et al. (Curr. Opin. Genet. Dev, 1998, 8, pp. 200-211) and Acquaviva et al. (2013 Science, 339, pp. 215-218). It has been shown that targeting Spo11 to a given site is sufficient to trigger the meiotic recombination process (Pecina et al., 2002 Cell, 111, pp. 173-184). It should be noted that multiple Spo11 protein homologues can co-exist in the same cell, in particular in plants. Preferably, when several fusion proteins are introduced into the eukaryotic cell, the different domains of Spo11 or Spo11 homologues introduced into the eukaryotic cell are all deficient in nuclease activity.

The Spo11 protein, fragment or domain thereof as used in the present invention, can be obtained from any known Spo11 protein such as the *Saccharomyces cerevisiae* Spo11 protein (Gene ID: 856364, NCBI accession number: NP_011841 (SEQ ID NO: 1), Esposito and Esposito, Genetics, 1969, 61, pp. 79-89), the *Arabidopsis thaliana* AtSpo11-1 and AtSpo11-2 protein (Grelon M. et al., 2001, Embo J., 20, pp. 589-600), the murine mSpo11 protein (Baudat F et al., 2000 Molecular Cell, 6, pp. 989-998), the *C. elegans* Spo11 protein or the *Drosophila* Spo11 protein meiW68 (McKim et al., 1998, Genes Dev, 12, pp. 2932-2942), subject to modification to render Spo11 nuclease activity deficient. Of course, these examples are not limiting and any known Spo11 protein with deficient nuclease activity can be used in the fusion protein according to the invention. Preferably, the Spo11 protein is obtained from one of the Spo11 proteins of the eukaryotic cell of interest. In particular, a Spo11 domain having deficient nuclease activity is a Spo11 domain incapable of generating double-strand breaks.

According to a particular embodiment, the Spo11 domain comprises, or consists of, a variant of a Spo11 protein, preferably a wild-type Spo11 protein, in particular a Spo11 protein of the eukaryotic cell of interest, said variant comprising a sequence having at least 80%, 85%, 90%, 95%, 96%, 97%, 98%, or 99% identity with said Spo11 protein and having deficient nuclease activity.

According to a preferred embodiment, the Spo11 domain comprises, or consists of, a variant of a Spo11 protein, preferably of a *Saccharomyces cerevisiae* Spo11 protein, such as, for example, the protein of sequence NP_011841 (SEQ ID NO: 1), comprising a sequence having at least 80, 85, 90, 95, 96, 97, 98, or 99% identity with a Spo11 protein, preferably with a *Saccharomyces cerevisiae* Spo11 protein, in particular the protein of sequence SEQ ID NO: 1, and having deficient nuclease activity.

According to a particular embodiment, multiple fusion proteins according to the invention comprising different Spo11 domains may be introduced into the same cell. In particular, when multiple Spo11 homologues exist in the eukaryotic cell of interest, the different fusion proteins may comprise different Spo11 homologues. By way of example, two fusion proteins according to the invention comprising *Arabidopsis thaliana* Spo11-1 and Spo11-2 domains, respectively, and modified to render their nuclease activity deficient may be introduced into the same cell, preferably into the same *Arabidopsis thaliana* cell. Also by way of example, one or more fusion proteins according to the invention comprising rice Spo11-1, Spo11-2, Spo11-3 and/or Spo11-4 domains modified to render their nuclease activity deficient, can be introduced into the same cell, preferably into the same rice cell. Numerous Spo11 homologues have been identified in different species, in particular in plant species (Sprink T and Hartung F, Frontiers in Plant Science, 2014, Vol. 5, Article 214, doi: 10.3389/fpls.2014.00214; Shingu Y et al., BMC Mol Biol, 2012, doi: 10.1186/1471-2199-13-1). The person skilled in the art can easily identify Spo11 homologues in a given species, in particular by means of well-known bioinformatics techniques.

According to a preferred embodiment, the Spo11 domain comprises, or consists of, a variant of a plant Spo11 protein, in particular selected from: *Arabidopsis thaliana* Spo11 proteins, for example as described under UniProt entry Q9M4A2-1 (SEQ ID NO: 10), *Oryza sativa* (rice) Spo11 proteins, for example as described by Fayos I. et al., 2019 Plant Biotechnol J. November; 17(11):2062-2077 and under UniProt entries Q2QM00 (SEQ ID NO: 11), Q7Y021 (SEQ ID NO: 12), Q5ZPV8 (SEQ ID NO: 13), A2XFC1 (SEQ ID NO: 14), and UniProt entry, Q6ZD95 (SEQ ID NO: 46), *Brassica campestris* (mustard) Spo11 proteins, for example as described under UniProt entries A0A024AGF2 (SEQ ID NO: 15) and A0A024AHI2 (SEQ ID NO: 16), *Zea mays* (corn) Spo11 proteins, for example as described under UniProt entries B6UAQ8 (SEQ ID NO: 17) and B6TWI5 (SEQ ID NO: 18), A0A1P8W169-1 (SEQ ID NO: 47) and A0A1P8W163 (SEQ ID NO: 48), *Capsicum baccatum* (pepper tree) Spo11 proteins, for example as described under entries A0A2G2WFG5 (SEQ ID NO: 19) and A0A2G2WFH4 (SEQ ID NO: 20), *Carica papaya* (papaya) Spo11 protein, for example as described under UniProt entry A0A024AG98 (SEQ ID NO: 21), said variant comprising a sequence having at least 80, 85, 90, 95, 96, 97, 98, or 99% identity with one of these Spo11 proteins, and having deficient nuclease activity.

In particular, the Spo11 domain may comprise, or consist of, a variant of a Spo11 protein selected from any of the above-mentioned Spo11 proteins, preferably from the sequences SEQ ID NO: 1 and 10 to 21 and 46-48, said variant comprising a sequence having at least 80, 85, 90, 95, 96, 97, 98, or 99% identity with one of these sequences and a deficient nuclease activity.

A variant of a Spo11 protein that has deficient nuclease activity is further also called 'dead Spo11' or 'dSpo11'. According to a particular embodiment, the DNA or RNA cleavage capacity and/or hydrolase activity of the Spo11 nuclease, preferably endonuclease DNA activity, is reduced or diminished, in particular relative to the nuclease activity of the wild-type Spo11 protein from which the variant is derived. Preferably, the nuclease activity of the Spo11 variant comprised in the Spo11 domain is reduced by at least 50, 55, 60, 65, 70, 75, 80, 85, 90, 95 or 100%, relative to the nuclease activity of wild-type Spo11. Most preferably, the Spo11 variant is devoid of nuclease activity, in particular endonuclease DNA activity. It is therefore incapable of generating double-strand breaks.

In particular, the Spo11 domain having deficient nuclease activity may comprise a mutated catalytic site which induces deficient nuclease activity, the mutation negatively impacting the nuclease or hydrolytic capacity of the Spo11 domain. Preferably, the Spo11 domain may comprise, or consist of, a variant of a Spo11 protein in which the residue corresponding to tyrosine at position 135 of SEQ ID NO: 1 is substituted, preferably with a phenylalanine, in particular as presented in SEQ ID NO: 2. A variant with such a substitution is unable to induce DNA double-strand breaks (Bergerat et al., Nature, vol. 386, pp. 414-7). The residue corresponding to tyrosine at position 135 of SEQ ID NO: 1 in the sequence of a Spo11 protein may easily be identified by conventional techniques of sequence alignment.

Accordingly, the Spo11 domain may be a variant of a Spo11 protein, preferably of a wild-type Spo11 protein, in particular of the eukaryotic cell of interest, having at least 80%, 85%, 90%, 95%, 96%, 97%, 98%, or 99% identity with said Spo11 protein and in which the residue corresponding to the tyrosine at position 135 of SEQ ID NO: 1 is substituted, preferably by a phenylalanine. In particular, the Spo11 domain may be a variant of the sequences SEQ ID NO: 1 and 10 to 21 and 46-48, having at least 80, 85, 90, 95, 96, 97, 98, or 99% identity with one of these sequences and in which the residue corresponding to the tyrosine at position 135 of SEQ ID NO: 1 is substituted, preferably by a phenylalanine. More particularly, the Spo11 domain may be a variant of a Spo11 protein, said variant comprising a sequence having at least 80%, 85%, 90%, 95%, 96%, 97%, 98%, or 99% identity with one of the sequences of SEQ ID NO: 10 to 21 and 46 to 48 and in which the residue corresponding to the tyrosine at position 135 of SEQ ID NO: 1 is substituted, preferably by a phenylalanine.

Preferably, the Spo11 domain having deficient nuclease activity is still capable of recruiting, directly or indirectly, one or more of the partners of Spo11, in particular one or more of the partners described below. Thus, although the nuclease activity of the Spo11 domain may be impaired, its ability to interact with Spo11 partners is preferably retained. The ability of one protein to recruit another, for example of a variant of a Spo11 protein to recruit a partner of Spo11, may easily be tested by the person skilled in the art by way of conventional techniques, such as the double hydride technique or the ChIP technique (chromatin immunoprecipitation). In particular, the partner can be selected from the proteins cited in the papers by Keeney et al. (2001 Curr. Top. Dev. Biol, 52, pp. 1-53), Smith et al. (Curr. Opin. Genet. Dev, 1998, 8, pp. 200-211), Acquaviva et al. (2013 Science, 339, pp. 215-8), Roberts et al. (Science 2016: Vol. 351, pp. 943-949) and Frank R. Blattner (Plant Systematics and Evolution volume 302, pp. 239-244 (2016). Preferably, the fusion protein according to the invention is still capable of recruiting one or more partners of Spo11 selected from Rec102, MTOPOVIB/TOPOVIBL, Rec103/Ski8, Rec104, Rec114, TOPOVIB, Mer1, Mer2/Rec107, Mei4, Mre2/Nam8, Mre11, Rad50, Xrs2/Nbs1, Hop1, Red1, Mek1, Set1, and Spp1, and orthologues thereof.

The fusion protein according to the present invention also comprises a nuclease associated with a CRISPR system having deficient nuclease activity (CRISPR domain). The CRISPR domain is the domain of the fusion protein that is capable of interacting with the guide RNA or RNAs and of targeting the activity of the fusion protein to a given chromosomal region. The variant of the nuclease associated with a CRISPR system is therefore deficient in nuclease activity, and preferably is devoid of endonuclease DNA activity, and is capable of interacting with the guide RNA or RNAs.

The CRISPR domain may be a variant of a nuclease associated with a CRISPR system, preferably of a wild-type nuclease, having at least 80%, 85%, 90%, 95%, 96%, 97%, 98%, or at least 99% identity with said nuclease and a deficient nuclease activity.

According to an embodiment, the fusion protein according to the invention comprises a variant of a nuclease associated with a class II CRISPR system, preferably type II, V or VI, preferentially type II, having a deficient nuclease activity. Type II includes types II-A, II-B, II-C, II-C, type V includes types V-A, V-B, V-C, V-D, V-E, V-U1, V-U2, V-U3, V-U4, V-U5 and type VI includes types VI-A, VI-B1, VI-B2, VI-C, VI-D.

According to an embodiment, the fusion protein according to the invention comprises a variant of a CRISPR system-associated nuclease selected from the group consisting of Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, their homologues, orthologues, variants or modified versions, said variant having deficient nuclease activity. In particular, the CRISPR domain of the fusion protein according to the invention may comprise a variant of a CRISPR system-associated nuclease selected from the group consisting of Cas1, Cas1B, Cas2, Cas3, Cas4, Cas5, Cas6, Cas7, Cas8, Cas9, Cas10, Cas11, Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1 and Csx15, and orthologues thereof, said variant having at least 80%, 85%, 90%, 95%, 96%, 97%, 98%, or at least 99% identity with one of these nucleases and deficient nuclease activity.

According to an embodiment, the fusion protein according to the invention comprises a variant of a nuclease associated with a CRISPR system selected from the group consisting of Cas1, Cas2, Cas9, Csn2, Cas13, C13a (C2c2), C13b, C13c, Cas12, C12a (Cpf1), C2c1 and C2c3, and having a deficient nuclease activity. Preferably, said variant has at least 80%, 85%, 90%, 95%, 96%, 97%, 98%, or at least 99% identity with one of these nucleases.

In particular, the CRISPR domain according to the invention may comprise a variant of a nuclease associated with a CRISPR system, preferably selected from the group consisting of Cas1, Cas2, Cas9, Csn2, Cas13, C13a (C2c2), C13b, C13c, Cas12, C12a (Cpf1), C2c1, and C2c3, said variant exhibiting a nuclease activity that is deficient relative to the wild-type protein. Preferably, said variant has at least 80%, 85%, 90%, 95%, 96%, 97%, 98%, or at least 99% identity with one of these nucleases.

According to an embodiment, the CRISPR domain of the fusion protein according to the invention is a variant of a nuclease associated with a class II and type II CRISPR system, for example Cas9 or Cns2, in particular the Cns2 nuclease of *Streptococcus thermophilus*, for example as described under GenBank accession number: AEM62890.1 (SEQ ID NO: 49), *Streptococcus pyogenes*, for example as described under GenBank accession number: ANC25453.1 (SEQ ID NO: 50), or *Streptococcus canis* for example as described under GenBank accession number: VTR80107.1 (SEQ ID NO: 51).

In particular, the variant of a nuclease associated with a CRISPR system, preferably class II and type II, having deficient nuclease activity, may comprise a mutated catalytic site, the mutation negatively impacting the nuclease or hydrolytic capacity of the protein but not impacting its ability to interact with the guide RNA and recognize the targeted region of the nucleic acid.

According to a particular embodiment, the variant of the nuclease associated with a CRISPR system deficient in nuclease activity may comprise, or consist of, a variant of a Cas9 protein deficient in nuclease activity (Cas9 domain).

The Cas9 domain may consist of a variant of a Cas9 protein (also called Csn1 or Csx12) or a fragment of this protein capable of interacting with guide RNAs but deficient in nuclease activity. The Cas9 protein can also be truncated to remove domains of the protein that are not essential to the functions of the fusion protein, particularly those domains of the Cas9 protein that are not required for interaction with the guide RNAs.

Generally, Cas9 proteins comprise two nuclease domains: a domain related to a RuvC domain and a domain related to a HNH domain. These two domains cooperate to create DNA double-strand breaks (Jinek et al., Science, 337: 816-821). Each of these nuclease domains can be inactivated by deletion, insertion, or substitution using techniques well known to the skilled person such as directed mutagenesis, PCR mutagenesis, or total gene synthesis. For example, the RuvC domain can be inactivated for example by the D10A substitution and the HNH domain can be inactivated for example by the H840A substitution (Jinek et al., 2012 Science, 337 pp. 816-821), the indicated positions being those of SEQ ID NO: 38. Thus, a variant of a Cas9 protein deficient in nuclease activity can be obtained by inactivating one or both nuclease domains of a Cas9 protein, for example by introducing a point mutation substituting the residue corresponding to aspartate at position 10 of SEQ ID NO: 38, preferably with an alanine, and/or a point mutation substituting the residue corresponding to histidine 840 of SEQ ID NO: 38, preferably with an alanine, preferably by introducing two point mutations substituting the residue corresponding to aspartate at position 10 of SEQ ID NO: 38 and the residue corresponding to histidine 840 of SEQ ID NO: 38, preferably with alanines. The residue corresponding to aspartate at position 10 of SEQ ID NO: 38 and the residue corresponding to histidine 840 of SEQ ID NO: 38, in the sequence of a Cas9 protein may be easily identified by conventional sequence alignment techniques.

According to an embodiment, the Cas9 domain is deficient in at least one nuclease activity. This domain can be obtained by inactivating at least one of the nuclease domains of the Cas9 protein as described above.

According to a particular embodiment, the Cas9 domain comprises, or consists of, a variant of a Cas9 protein or a Cas9 protein fragment, devoid of nuclease activity (also called Cas9* or dCas9).

The Cas9 domain as used in the present invention can be obtained from any Cas9 protein (Makarova et al., 2008, Nat. Rev. Microbiol., 9, pp. 466-477) which is known and which has been in particular modified to reduce or inactivate nuclease activity. Accordingly, the CRISPR domain may comprise, or consist of, a variant of a Cas9 protein, preferably a wild-type Cas9 protein, comprising a sequence having at least 80, 85, 90, 95, 96, 97, 98, or at least 99% identity with said Cas9 protein and in which the residue corresponding to the aspartate at position 10 of SEQ ID NO: 38 and/or the residue corresponding to the histidine at position 840 of SEQ ID NO: 38 have been substituted, preferably by alanines, and more particularly preferably in which the residue corresponding to the aspartate at position 10 of SEQ ID NO: 38 and the residue corresponding to the histidine at position 840 of SEQ ID NO: 38 have been substituted, preferably by alanines.

Examples of Cas9 proteins from which the Cas9 domain comprised in the fusion protein according to the present invention may be derived include, but are not limited to, the Cas9 proteins of *Streptococcus pyogenes*, *Streptococcus thermophilus*, *Streptococcus* sp., *Nocardiopsis dassonvillei*, *Streptomyces pristinaespiralis*, *Streptomyces viridochromogenes*, *Streptosporangium roseum*, *Alicyclobacillus acidocaldarius*, *Bacillus pseudomycoides*, *Bacillus selenitireducens*, *Exiguobacterium sibiricum*, *Lactobacillus delbrueckii*, *Lactobacillus salivarius*, *Microscilla marina*, *Burkholderiales bacterium*, *Polaromonas naphthalenivorans*, *Polaromonas* sp., *Crocosphaera watsonii*, *Cyanothece* sp., *Microcystis aeruginosa*, *Synechococcus* sp., *Acetohalobium arabaticum*, *Ammonifex degensii*, *Caldicelulosiruptor becscii*, *Candidatus Desulforudis*, *Clostridium botulinum*, *Clostridium difficile*, *Finegoldia magna*, *Natranaerobius thermophilus*, *Pelotomaculum thermopropionicum*, *Acidithiobacillus caldus*, *Acidithiobacillus ferrooxidans*, *Allochromatium vinosum*, *Marinobacter* sp., *Nitrosococcus halophilus*, *Nitrosococcus watsoni*, *Pseudoalteromonas haloplanktis*, *Ktedonobacter racemifer*, *Methanohalobium evestigatum*, *Anabaena variabilis*, *Nodularia spumigena*, *Nostoc* sp., *Arthrospira maxima*, *Arthrospira platensis*, *Arthrospira* sp., *Lyngbya* sp., *Microcoleus chthonoplastes*, *Oscillatoria* sp., *Petrotoga mobilis*, *Thermosipho africanus*, or *Acaryochloris marina*. Other Cas9 proteins that can be used in the present invention are also described in the paper by Makarova et al. (Makarova et al., 2008, Nat. Rev. Microbiol, 9, pp. 466-477) and have been widely described in the literature such as the Cas9 proteins of *Streptococcus pyogenes* (SpCas9, in particular as described under UniProt entry G3ECR1 or according to SEQ ID NO: 38), *Streptococcus thermophiles* (St1Cas9, St3Cas9, in particular as described under UniProt entry J7RUA5 or according to SEQ ID NO: 39), *Staphylococcus aureus* (SaCas9, in particular as described under SEQ ID NO: 40), *Campylobacter jejuni* (CjCas9, in particular as described under UniProt entry Q0P897 or according to SEQ ID NO: 41), *Francisella novicida* (FnCas9, particularly as described under UniProt entry A0Q5Y3 or according to SEQ ID NO: 42) and *Neisseria meningitides* (NmCas9, particularly as described under UniProt entry X5EPV9 or according to SEQ ID NO: 43). In particular, the Cas9 domain may comprise a variant of a Cas9 protein comprising a sequence having at least 80, 85, 90, 95, 96, 97, 98, or at least 99% identity with one of these sequences, preferably with one of the sequences SEQ ID NO: 38 to 43, and in which the residue corresponding to the aspartate at position 10 of SEQ ID NO: 38 and/or the residue corresponding to the histidine at position 840 of SEQ ID NO: 38 have been substituted, preferably with alanines, preferably wherein the residue corresponding to the aspartate at position 10 of SEQ ID NO: 38 and the residue corresponding to the histidine at position 840 of SEQ ID NO: 38 have been substituted, preferably with alanines.

According to a particular embodiment, the Cas9 domain is a variant of an entire Cas9 protein, preferably a variant of the Cas9 protein of *Streptococcus pyogenes* (spCas9).

Preferably, the Cas9 domain comprises, or consists of, a sequence having at least 80, 85, 90, 95, 96, 97, 98, or at least 99% identity with the Cas9 protein of *Streptococcus pyogenes* (NCBI accession number: WP_010922251.1, SEQ ID NO: 38), said variant being deficient in nuclease activity, and preferably wherein the residue corresponding to aspartate at position 10 of SEQ ID NO: 38 and/or the residue corresponding to histidine at position 840 of SEQ ID NO: 38 have been substituted, preferably with alanines, preferably wherein the residue corresponding to aspartate at position 10 of SEQ ID NO: 38 and the residue corresponding to histidine at position 840 of SEQ ID NO: 38 have been substituted, preferably with alanines. Preferably, the Cas9 domain comprises, or consists of, a sequence comprising SEQ ID NO: 38 in which the aspartate at position 10 and/or the histidine at position 840 have been substituted, preferably with alanines, wherein the aspartate at position 10 and the histidine at position 840 have been substituted, preferably with alanines.

According to another embodiment, the fusion protein according to the invention comprises a variant of a nuclease associated with a class II and type V CRISPR system, preferably Cpf1 (also called Cas12a), C2c1 (also called Cas12b) or C2c3, preferentially Cpf1 and having a deficient nuclease activity. In particular, the variant of the nuclease associated with a class II and type V CRISPR system having deficient nuclease activity may be a variant of a nuclease associated with a class II and type V CRISPR system comprising a mutated catalytic site, the mutation negatively impacting the nuclease or hydrolytic capacity of the protein but not impacting its ability to interact with the guide RNA and recognize the targeted region of the nucleic acid. Preferably, the fusion protein comprises a variant of a Cpf1 nuclease (Cpf1 domain), said variant having a deficient nuclease activity.

The Cpf1 domain can be derived from Cpf1 proteins of bacteria of the genera *Prevotella, Moraxella, Leptospira, Lachnospiraceae, Francissela, Candidatus, Eubacterium, Parcubacteria, Peregrinibacteria, Acidmicococcus* and *Prophyromonas*. In particular, the Cpf1 domain can be obtained from the Cpf1 proteins of *Parcubacteria bacterium* GWC2011_GWC2_44_17 (PbCpf1, for example as described under GenBank accession number KKT48220.1, SEQ ID NO: 22), *Peregrinibacteria bacterium* GW2011_GWA_33_10 (PeCpf1, for example as described under GenBank accession number KKP36646.1, SEQ ID NO: 23), *Acidaminococcus* sp. BVBLG (AsCpf1, for example as described under GenBank accession number WP_021736722.1, SEQ ID NO: 24), *Prophyromonas macacae* (PmCpf1, for example as described under GenBank accession number WP_018359861.1, SEQ ID NO: 25), *Prophyromonas crevioricanis* (PcCpf1, for example as described under GenBank accession number WP_036890108.1, SEQ ID NO: 26), *Francisella tularensis*

(UniProtKB: A0Q7Q2, SEQ ID NO: 27) *Acidaminococcus* sp. (UniProtKB: U2UMQ6, SEQ ID NO: 28), *Prevotella disiens* (PdCpF1, for example as described under GenBank accession number WP_004356401.1, SEQ ID NO: 29), *Moraxella bovoculi* 237 (MbCpf1, for example as described under GenBank accession number KDN25524.1, SEQ ID NO: 30), *Leptospira inadai* (LiCpf1, for example as described under GenBank accession number WP_020988726.1, SEQ ID NO: 31), Lachnospiraceae bacterium MA2020 (LbCpf1, for example as described under GenBank accession number WP_044919442.1, SEQ ID NO: 32), *Francisella novicida* U112 (FnCpf1, for example as described under GenBank accession number WP_003040289.1, SEQ ID NO: 33). Of course, these examples are not limiting and any known Cpf1 protein can be used to obtain the Cpf1 domain of the fusion protein according to the invention. According to a particular embodiment, the Cpf1 domain comprises, or consists of, a variant of a protein comprising a sequence selected from among the sequences described above, in particular selected from among the sequences SEQ ID NO: 22 to 33, said variant comprising a sequence having at least 80, 85, 90, 95, 96, 97, 98, or at least 99% identity with one of these sequences, said variant being deficient in nuclease activity relative to a wild-type Cpf1 protein, preferably relative to the Cpf1 protein from which it is derived.

This type of variant may comprise mutations in the RuvC nuclease domain of Cpf1.

To facilitate targeting to different regions of the genome, the Cpf1 domain may also comprise mutations that alter PAM recognition as described in Gao et al., Nat Biotechnol. 2017 August; 35(8): 789-792. The Cpf1 protein may also be truncated to remove domains of the protein that are non-essential to the functions of the fusion protein, in particular domains of the Cpf1 protein that are not required for interaction with the guide RNA. According to a particular embodiment, the Cpf1 domain comprises, or consists of, a sequence variant of FnCpf1 (SEQ ID NO: 3) or LbCp (SEQ ID NO: 4) comprising a sequence having at least 80, 85, 90, 95, 96, 97, 98, or at least 99% identity with the sequence of SEQ ID NO: 3 or 4, and wherein the nuclease activity is reduced relative to the nuclease activity of SEQ ID NO: 3 or 4, preferably said variant being devoid of nuclease activity.

Preferably, the variant of a nuclease associated with a CRISPR system deficient in nuclease activity may comprise, or consist of, a mutant Cpf1 protein for example as described in Zhang et al., Cell Discov. 2018; 4: 36, having the mutation D832A (position corresponding to SEQ ID NO: 4). A Cpf1 protein with such a substitution is unable to induce DNA double-strand breaks, and may in particular be referred to as 'dead Cpf1' or 'dCpf1'. Thus, the CRISPR domain may comprise, or consist of, a variant of a Cpf1 protein, preferably a wild-type Cpf1 protein, comprising a sequence having at least 80, 85, 90, 95, 96, 97, 98, or at least 99% identity with said Cpf1 protein and wherein the residue corresponding to aspartate at position 832 of SEQ ID NO: 4 is substituted, preferably with an alanine. In particular, the Cpf1 domain can be a variant of the sequences SEQ ID NO: 3, 4 and 22 to 33 having at least 80, 85, 90, 95, 96, 97, 98, or at least 99% identity with one of these sequences and wherein the residue corresponding to aspartate at position 832 of SEQ ID NO: 4 is substituted, preferably with an alanine. Preferably, the dCpf1 domain may comprise or consist of the sequence SEQ ID NO: 5 or SEQ ID NO: 6. The residue corresponding to aspartate at position 832 of SEQ ID NO: 4 in the sequence of a Cpf1 protein may be easily identified by conventional sequence alignment techniques.

According to another embodiment, the fusion protein according to the invention comprises a variant of a nuclease associated with a class II and type VI CRISPR system, preferably of Cas13a (C2c2), Cas13b or Cas13c, for example the Cas13a nuclease of *Herbinix hemicellulosilytica*, in particular as described under GenBank accession number: WP_103203632.1 (SEQ ID NO: 52), the Cas13a nuclease of Lachnospiraceae bacterium, in particular as described under GenBank accession number: WP_022785443.1 (SEQ ID NO: 53), or the Cas13a nuclease of *Leptotrichia wadei*, in particular as described under GenBank accession number: WP_021746003.1 (SEQ ID NO: 54), and having a deficient nuclease activity. In particular, the fusion protein may comprise a Cas13 variant, in particular a variant of the Cas13 proteins described above and having a deficient nuclease activity, in particular an abolished or reduced nuclease activity. Such a variant may comprise, in particular, mutations in the RuvC nuclease domain of Cas13. In particular, the nuclease associated with a class II and type VI CRISPR system having deficient nuclease activity may comprise a mutated catalytic site, the mutation negatively impacting the nuclease or hydrolytic capacity of the protein but not impacting its ability to interact with the guide RNA and to recognize the targeted region of the nucleic acid.

According to one particular embodiment, the fusion protein according to the convention comprises a variant of a Cas9 protein, preferably a wild-type Cas9 protein, comprising a sequence having at least 80, 85, 90, 95, 96, 97, 98, or at least 99% identity with said Cas9 protein and in which the residue corresponding to the aspartate at position 10 of SEQ ID NO: 38 and/or the residue corresponding to the histidine at position 840 of SEQ ID NO: 38 have been substituted, preferably by alanines, preferably in which the residue corresponding to the aspartate at position 10 of SEQ ID NO: 38 and the residue corresponding to the histidine at position 840 of SEQ ID NO: 38 have been substituted, preferably by alanines, and a variant of a Spo11 protein, preferably of a wild-type Spo11 protein, having at least 80%, 85%, 90%, 95%, 96%, 97%, 98%, or at least 99% identity with said Spo11 protein and in which the residue corresponding to tyrosine at position 135 of SEQ ID NO: 1 is substituted, preferably by a phenylalanine.

According to an embodiment, the Spo11 domain is on the N-terminal side and the CRISPR domain on the C-terminal side of the fusion protein. According to another embodiment, the Spo11 domain is on the C-terminal side and the CRISPR domain on the N-terminal side of the fusion protein.

The fusion protein may also comprise a nuclear localization signal (NLS) sequence. NLS sequences are well known to the skilled person and generally comprise a short sequence of basic amino acids. By way of example, the NLS sequence may comprise the sequence PKKKRKV (SEQ ID NO: 7). The NLS sequence may be present at the N-terminus, the C-terminus or in an internal region of the fusion protein.

The fusion protein may also comprise an additional cell-penetration domain, i.e. a domain facilitating the entry of the fusion protein into the cell. This type of domain is well known to the skilled person and may comprise, for example, a penetration peptide sequence derived from the HIV-1 TAT protein such as GRKKRRQRRRPPQPKKKRKV (SEQ ID NO: 8), derived from the TLM sequence of the human hepatitis B virus such as PLSSIFSRIGDPPKKKRKV (SEQ ID NO: 9), or a polyarginine peptide sequence. This cell-penetration domain may be present at the N-terminus, C-terminus, or within the fusion protein.

The fusion protein may further comprise one or more linkage sequences (linkers) between the CRISPR domains and Spo11, and optionally between these domains and other domains of the protein such as the nuclear localization signal sequence or the cell-penetration domain. The length of these linkers is easily adjustable by the skilled person. In general, these sequences comprise between 10 and 20 amino acids, preferably about 15 amino acids and even more preferably 12 amino acids. The linkers between the different domains can be of identical or different lengths.

According to a particular embodiment, the fusion protein comprises, or consists of, successively, from the N-terminus to the C-terminus: a nuclear localization signal, a first linker (linker1), a CRISPR domain, a second linker (linker2) and a Spo11 domain.

According to another particular embodiment, the fusion protein comprises, or consists of, successively, from the N-terminus to the C-terminus: a nuclear localization signal, a first linker (linker1), a Spo11 domain, a second linker (linker2) and a CRISPR domain, preferably a Cas9 domain.

The fusion protein may further comprise a label (or tag) that is a defined sequence of amino acids. This tag can in particular be used to detect the expression of the fusion protein, to identify proteins interacting with the fusion protein or to characterize the binding sites of the fusion protein in the genome. The detection of the tag attached to the fusion protein can be performed with an antibody specific for said tag or any other technique well known to the skilled person. Identification of the proteins interacting with the fusion protein can be carried out, for example, by co-immunoprecipitation techniques. The characterization of the binding sites of the fusion protein in the genome can be carried out, for example, by immunoprecipitation, chromatin immunoprecipitation coupled with real-time quantitative PCR (ChIP-qPCR), chromatin immunoprecipitation coupled with sequencing (ChIP-Seq), oligonucleotide mapping or any other technique well known to the skilled person.

This tag may be present at the N-terminus of the fusion protein, at the C-terminus of the fusion protein, or at a non-terminal position in the fusion protein. Preferably, the tag is present at the C-terminus of the fusion protein. The fusion protein may comprise one or more tags, identical or different and in any combination of localization, in particular at the N-terminus, C-terminus, N- and C-termini or at positions internal to the fusion protein.

The tags, as used in the present invention, may be selected from the many tags well known to the skilled person. In particular, the tags used in the present invention may be peptide tags and/or protein tags. Preferably, the tags used in the present invention are peptide tags. Examples of peptide tags that can be used in the present invention include, but are not limited to, tags formed from repeats of at least six histidines (His), in particular tags formed from six or eight histidines, as well as the Flag, polyglutamate, hemagglutinin (HA), calmodulin, Strep, myc, V5, Xpress, VSV, S-tag, Avi, SBP, Softag 1, Softag 2, Softag 3, isopetag, SpyTag, and tetracysteine tags, and combinations thereof. Examples of protein tags that can be used in the present invention include, but are not limited to, Glutathione-S-Transferase (GST), *Staphylococcus aureus* protein A, Nus A, chitin binding protein (CBP), thioredoxin, maltose binding protein (MBP), biotin carboxyl carrier protein (BCCP), immunoglobulin constant fragment (Fc), tags comprising a fluorescent protein such as GFP (Green Fluorescent Protein), RFP (Red Fluorescent Protein), CFP (Cyan Fluorescent Protein) or YFP (Yellow Fluorescent Protein), and combinations thereof.

According to a preferred embodiment, the fusion protein comprises a tag formed by six histidines and/or one or more Flag motifs, preferably three Flag motifs. According to an embodiment, the fusion protein comprises a tag formed by three Flag motifs followed by 6 histidines at the C-terminus of the fusion protein. Additionally or alternatively, the fusion protein comprises a V5 motif, preferably on the N-terminal side of the fusion protein. The V5 tag is derived from a small epitope (Pk) found on the P and V proteins of simian virus family 5 (SV5) paramyxovirus. The V5 tag is generally used with 14 amino acids (GKPIPNPLLGLDST, SEQ ID NO: 44) or 9 amino acids shorter (IPNPLLGLD, SEQ ID NO: 45). According to a particular embodiment, the fusion protein comprises a tag formed by six histidines and three Flag motifs, preferably C-terminal, and an N-terminal V5 motif.

The fusion protein as described above can be introduced into the cell in a protein form, in particular in its mature form or in the form of a precursor, preferably in its mature form, or in the form of a nucleic acid encoding said protein.

When the fusion protein is introduced into the cell in a protein form, protecting groups can be added to the C- and/or N-termini to improve the resistance of the fusion protein to peptidases. For example, the protective group at the N-terminus may be acylation or acetylation and the protective group at the C-terminus may be amidation or esterification. The action of proteases can also be counteracted by the use of D-configuration amino acids, cyclization of the protein by formation of disulphide bridges, lactam rings or linkages between the N- and C-termini. The fusion protein of the invention may also comprise pseudo-peptide bonds replacing the 'classical' CONH peptide bonds and conferring increased resistance to peptidases, such as CHOH—CH2, NHCO, CH2-O, CH2CH2, CO—CH2, N—N, CH=CH, CH2NH, and CH2-S. The fusion protein may also comprise one or more amino acids which are rare amino acids, in particular hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid; or synthetic amino acids, in particular ornithine, norleucine, norvaline, and cyclohexyl-alanine.

The fusion protein according to the invention can be obtained by conventional chemical synthesis (in solid phase or in liquid homogeneous phase) or by enzymatic synthesis (Kullmann W, Enzymatic peptide synthesis, 1987, CRC Press, Florida). It can also be obtained by a method consisting in culturing a host cell expressing a nucleic acid encoding the fusion protein and recovering said protein from these cells or from the culture medium.

The present invention also relates to a nucleic acid encoding the fusion protein according to the invention, in particular a fusion protein comprising a variant of a class II nuclease of the CRISPR system, preferably type II and preferentially Cas9, and a variant of a Spo11 protein, both having a deficient nuclease activity.

For the purposes of the invention, 'nucleic acid' means any DNA- or RNA-based molecule. These molecules may be synthetic or semi-synthetic, recombinant, possibly amplified or cloned into vectors, chemically modified, comprising non-natural bases or modified nucleotides comprising for example a modified bond, a modified purine or pyrimidine base, or a modified sugar. Preferably, the use of codons is optimized according to the nature of the eukaryotic cell of interest.

The nucleic acid according to the invention may be in the form of DNA and/or RNA, single-stranded or double-stranded. According to a preferred embodiment, the nucleic acid is an isolated DNA molecule, synthesized by recombinant techniques well known to the person skilled in the art. The nucleic acid according to the invention can be deduced from the sequence of the fusion protein according to the invention and the use of codons can be adapted according to the host cell in which the nucleic acid is to be transcribed.

The present invention further relates to an expression cassette comprising a nucleic acid according to the invention operably linked to the sequences necessary for its expression. In particular, the nucleic acid may be under the control of a promoter enabling its expression in a eukaryotic host cell. In general, an expression cassette comprises, or consists of, a promoter for initiating transcription, a nucleic acid according to the invention, and a transcription terminator.

The term 'expression cassette' refers to a nucleic acid construct comprising a coding region and a regulatory region, operably linked. The term 'operably linked' indicates that the elements are combined in such a way that the expression of the coding sequence is under the control of the transcriptional promoter. Typically, the promoter sequence is placed upstream of the gene of interest, at a distance from it compatible with control of its expression. Spacer sequences may be present between the regulatory elements and the gene, as long as they do not prevent expression. The expression cassette may also include at least one activating 'enhancer' sequence operably linked to the promoter.

A wide variety of promoters that can be used for the expression of genes of interest in cells or host organisms are available to the skilled person. They include constitutive promoters as well as inducible promoters that are activated or repressed by exogenous physical or chemical stimuli.

Preferably, the nucleic acid according to the invention is placed under the control of a constitutive promoter or a meiosis-specific promoter.

Examples of meiosis-specific promoters that can be used in the present invention include, but are not limited to, endogenous Spo11 promoters, promoters of Spo11 partners for double-strand break formation, the Rec8 promoter (Murakami & Nicolas, 2009, Mol. Cell. Biol, 29, pp. 3500-3516), or the Spo13 promoter (Malkova et al., 1996, Genetics, 143, pp. 741-754), meiotic promoters from *Arabidopsis thaliana* for example as described in Li et al., BMC Plant Biol. 2012; 12: pp. 104, Eid et al., Plant Cell Rep. 2016, 35(7) pp. 1555-1558, Xu et al., Front. Plant Sci., 13 Jul. 2018, Da Ines et al., *PLoS Genet,* 2013, 9, e1003787).

Other inducible promoters can also be used such as the oestradiol promoter (Carlie & Amon, 2008 Cell, 133, 280-91), the methionine promoter (Care et al., 1999, Molecular Microb 34, 792-798), the doxycycline-inducible TetO/TetR system, heat shock-induced promoters, metals, steroids, antibiotics, and alcohol.

Constitutive promoters that can be used in the context of the present invention are, by way of non-limiting examples: cytomegalovirus (CMV) immediate-early gene promoter, simian virus (SV40) promoter, adenovirus major late promoter, Rous sarcoma virus (RSV) promoter, mouse mammary tumor virus (MMTV) promoter, phosphoglycerate kinase (PGK) promoter, ED1-alpha elongation factor promoter, ubiquitin promoters, actin promoters, tubulin promoters, immunoglobulin promoters, alcohol dehydrogenase 1 (ADH1) promoter, RNA polymerase III-dependent promoters such as the U6, U3, H1, 7SL, pRPR1 ('Ribonuclease P RNA 1'), and SNR52 ('small nuclear RNA 52') promoters, or the pZmUbi promoter.

Preferably, the expression cassette and/or the nucleic acid according to the invention is operably linked to a transcriptional promoter allowing expression of the expression cassette and/or the nucleic acid during meiosis. For example, such a promoter may be pREC8.

The transcription terminator can be easily chosen by the skilled person. Preferably, this terminator is RPR1t, the 3' flanking sequence of the SUP4 gene of *Saccharomyces cerevisiae* or the nopaline synthase terminator tNOS.

The present invention further relates to an expression vector comprising a nucleic acid or an expression cassette according to the invention. This expression vector can be used to transform a host cell and allow expression of the nucleic acid according to the invention in said cell. The vectors can be constructed by conventional molecular biology techniques, well known to the skilled person.

Advantageously, the expression vector comprises regulatory elements allowing the expression of the nucleic acid according to the invention. These elements may comprise, for example, transcription promoters, transcription activators, terminator sequences, and initiation and termination codons. Methods for selecting these elements according to the host cell in which expression is desired are well known to the skilled person.

In a particular embodiment, the expression vector comprises a nucleic acid encoding the fusion protein according to the invention, placed under the control of a constitutive promoter, preferably the ADH1 promoter (pADH1). It may also comprise a terminator sequence such as the ADH1 terminator (tADH1).

The expression vector may comprise one or more bacterial or eukaryotic origins of replication. In particular, the expression vector may comprise a bacterial origin of replication functional in *E. coli* such as the ColE1 origin of replication. Alternatively, the vector can comprise a eukaryotic origin of replication, preferably functional in plants and in yeast, in particular in *S. cerevisiae*.

The vector may further comprise elements allowing its selection in a bacterial or eukaryotic host cell such as, for example, an antibiotic resistance gene or a selection gene ensuring the complementation of the respective deleted gene in the host cell genome. Such elements are well known to the skilled person and widely described in the literature.

In a particular embodiment, the expression vector comprises one or more antibiotic resistance genes, preferably an ampicillin, kanamycin, hygromycin, geneticin and/or nourseothricin resistance gene.

The expression vector may also comprise one or more sequences allowing targeted insertion of the vector, expression cassette, or nucleic acid into the genome of a host cell. Preferably, the insertion is performed at a gene whose inactivation allows the selection of host cells that have integrated the vector, cassette, or nucleic acid, such as the TRP1 locus.

The vector can be circular or linear, single- or double-stranded. It is advantageously selected from plasmids, phages, phagemids, viruses, cosmids, and artificial chromosomes. Preferably, the vector is a plasmid.

The present invention relates in particular to a vector, preferably a plasmid, comprising a bacterial origin of replication, preferably the ColE1 origin, a nucleic acid as defined above under the control of a promoter, preferably a constitutive promoter such as the ADH1 promoter, a terminator, preferably the ADH1 terminator, one or more selection markers, preferably resistance markers such as the kanamycin or ampicillin resistance gene, and one or more sequences allowing the targeted insertion of the vector, expression cassette, or nucleic acid into the host cell genome, preferably at the TRP1 locus of the yeast genome.

According to an embodiment, the invention relates in particular to a vector, preferably a plasmid, compatible for agrotransfection, in particular using *Agrobacterium tumefaciens* (Fraley et al. Crit. Rev. Plant. Sci. 1986 4 pp. 1-46; Fromm et al., Biotechnology 1990, 8, pp. 833-844) or *Agrobacterium rhizogenes* (Cho et al. 2000 Planta 210 pp. 195-204) and aimed at plant transformation. An example of a compatible plasmid is the Ti type plasmid, in particular pBIN19 (Lee and Gelvin, 2008 Plant Physiology 146(2): pp. 325-332). In particular, when intended for use in planta, the vector according to the invention comprises a selectable marker. The most commonly used selectable markers for plant transformation include the kanamycin neomycin phosphotransferase II (NPTII) resistance conferring gene, used for selection in a kanamycin-containing culture, the phosphinothricin acetyltransferase (HPH) gene, used for selection in a culture containing hygromycin B.

In a particular embodiment, the nucleic acid according to the invention carried by the vector encodes a fusion protein comprising one or more tags, preferably comprising a tag consisting of six histidines and/or one or more Flag motifs, preferably three Flag motifs. Preferably the tag or tags are C-terminal.

The present invention also relates to the use of a nucleic acid, an expression cassette or an expression vector according to the invention to transform or transfect a cell. The host cell may be transiently or stably transformed/transfected and the nucleic acid, cassette or vector may be contained within the cell as an episome or integrated into the host cell genome.

The present invention thus relates to a host cell comprising a fusion protein, a nucleic acid, a cassette or an expression vector according to the invention.

Preferably, the cell is a eukaryotic cell.

As used herein, the term 'eukaryotic cell' refers to a yeast cell, a plant cell, a fungal cell or an animal cell, in particular a mammalian cell such as a mouse or rat cell, or an insect cell. The eukaryotic cell is preferably non-human and/or non-embryonic. Preferably the eukaryotic cell is not an embryonic stem cell of human and/or animal origin.

Preferably, the eukaryotic cell expresses a Spo11 protein endowed with nuclease activity, i.e. a Spo11 protein capable of inducing double-strand breaks during prophase I of meiosis. This protein can be an endogenous Spo11 protein of the cell or a heterologous Spo11 protein. Preferably, this protein is an endogenous Spo11 protein of the cell.

According to a particular embodiment, the eukaryotic cell is a yeast cell, in particular a yeast of industrial interest. Examples of yeasts of interest include, but are not limited to, yeasts of the genus *Saccharomyces sensu stricto, Schizosaccharomyces, Yarrowia, Hansenula, Kluyveromyces, Pichia* or *Candida*, as well as hybrids obtained from a strain belonging to one of these genera.

Preferably, the yeast of interest belongs to the genus *Saccharomyces*, preferably a yeast selected from the group consisting of *Saccharomyces cerevisiae, Saccharomyces bayanus, Saccharomyces castelli, Saccharomyces eubayanus, Saccharomyces kluyveri, Saccharomyces kudriavzevii, Saccharomyces mikatae, Saccharomyces uvarum, Saccharomyces paradoxus, Saccharomyces pastorianus* (also called *Saccharomyces carlsbergensis*), and hybrids obtained from at least one strain belonging to one of these species such as for example an *S. cerevisiae/S. paradoxus* hybrid or an *S. cerevisiae/S. uvarum* hybrid, more preferably said eukaryotic host cell is *Saccharomyces cerevisiae*.

According to another particular embodiment, the eukaryotic cell is a fungal cell, in particular a fungal cell of industrial interest. Examples of fungi include, but are not limited to, cells of filamentous fungi. Filamentous fungi include fungi belonging to the subdivisions Eumycota and Oomycota. The cells of filamentous fungi may be selected from the group consisting of cells of *Trichoderma, Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Sordaria, Talaromyces, Thermoascus, Thielavia, Tolypocladium* or *Trametes*.

According to yet another particular embodiment, the eukaryotic cell is a plant cell, in particular a plant cell of agronomic, horticultural, pharmaceutical or cosmetic interest, in particular vegetables, fruits, herbs, flowers, trees and shrubs.

The plant cell is preferably selected from monocotyledonous plants and dicotyledonous plants, more particularly preferably selected from the group consisting of rice, wheat, soybean, corn, tomato, onion, cucumber, lettuce, asparagus, carrot, turnip, *Arabidopsis thaliana*, barley, rapeseed, cotton, grapevine, sugar cane, beet, cotton, sunflower, oil palm, coffee, tea, cocoa, chicory, bell pepper, chili, lemon, orange, nectarine, mango, apple, banana, peach, apricot, sweet potato, yam, almond, hazelnut, strawberry, melon, watermelon, olive tree, potato, zucchini, eggplant, avocado, cabbage, plum, cherry, pineapple, spinach, apple, mandarin, grapefruit, pear, grape, clove, cashew nut, coconut, sesame, rye, hemp, tobacco, berries such as raspberry or blackcurrant, peanut, castor, vanilla, poplar, eucalyptus, green foxtail, casava, and horticultural plants such as, for example, roses, tulips, orchids and geraniums. In particular, the plant cell may be selected from the group consisting of rice, wheat, soybean, corn, tomato, onion, cucumber, lettuce, asparagus, carrot, turnip, *Arabidopsis thaliana*, barley, rapeseed, cotton, grapevine, sugar cane, beet, cotton, sunflower, palm olive tree, coffee tea, cocoa, chicory, bell pepper, chili, lemon, orange, nectarine, mango, apple, banana, peach, apricot, sweet potato, yam, almond, hazelnut, strawberry, melon, watermelon, olive tree, and horticultural plants such as roses, tulips, orchids and geraniums.

Each of the different cells described above can in particular be used in the processes according to the invention described below.

Thus, the present invention also relates to the use of the fusion protein, the nucleic acid, the expression cassette or the expression vector according to the invention to (i) induce targeted meiotic recombinations in a eukaryotic cell, (ii) generate variants of a eukaryotic organism, and/or (iii) identify or locate genetic information encoding a trait of interest in a eukaryotic cell genome.

The invention also relates to processes for (i) inducing targeted meiotic recombinations in a eukaryotic cell, (ii) generating variants of a eukaryotic organism, and/or (iii) identifying or locating genetic information encoding a trait of interest in a eukaryotic cell genome as described below.

The processes according to the invention can be in vitro, in vivo or ex vivo processes, preferably in vitro processes.

The invention relates in particular to a process for inducing targeted meiotic recombinations in a eukaryotic cell, preferably non-human, comprising introduction into said cell of:
a) a fusion protein, a nucleic acid, an expression cassette, or a vector as described above; and
b) one or more guide RNAs or one or more nucleic acids encoding said guide RNAs, said guide RNAs comprising a nuclease binding RNA structure associated with a CRISPR system of the fusion protein and a sequence complementary to the targeted chromosomal region; and induction of entry into prophase I of meiosis of said cell.

In particular, the eukaryotic cell is as described above.

As used in the present application, the term 'guide RNA' or 'gRNA' refers to an RNA molecule capable of interacting with the CRISPR domain, preferably with the Cpf1 or Cas9 domain, of the fusion protein in order to guide it to a target chromosomal region.

Each gRNA comprises a region (commonly called the 'SDS' region), at the 5' end of the gRNA, that is complementary to the target chromosomal region and mimics the crRNA of the endogenous CRISPR system.

When the CRISPR system used is a class II and type II CRISPR system, preferably Cas9, each gRNA comprises two regions:
a first region (commonly called the 'SDS' region), at the 5' end of the gRNA, which is complementary to the target chromosomal region and which mimics the crRNA of the endogenous CRISPR system, and
a second region (commonly called the 'handle' region), at the 3' end of the gRNA, which mimics the base-pairing interactions between the trans-activating crRNA (tracrRNA) and the crRNA of the endogenous CRISPR system and has a double-stranded stem-loop structure ending at 3' with an essentially single-stranded sequence. This second region is essential for the binding of the gRNA to the Cas9 domain of the fusion protein.

When the CRISPR system used is a CRISPR system of class II and of type V, preferably Cpf1, the gRNA does not require the second region.

The first region of the gRNA varies according to the targeted chromosomal sequence. On the other hand, the 'handle' regions of the different gRNAs used may be identical or different. According to a particular embodiment, the 'handle' region comprises, or consists of, the 82-nucleotide 3' sequence of sequences SEQ ID NO: 10 to 16.

The 'SDS' region of the gRNA, which is complementary to the target chromosomal region, generally comprises between 10 and 25 nucleotides. Preferably, this region has a length of 19, 20 or 21 nucleotides, and particularly preferably of 20 nucleotides.

The second region of the gRNA has a stem-and-loop (or hairpin) structure. The lengths of the stem and loop can vary. Preferably, the loop has a length of 3 to 10 nucleotides and the stem a length of 6 to 20 nucleotides. The stem may, optionally, have unpaired regions (forming 'bumps') of 1 to 10 nucleotides. Preferably, the overall length of this 'handle' region is 50 to 100 nucleotides, and more particularly preferably 82 nucleotides.

The total length of a gRNA is in general from 30 to 140 nucleotides, preferably from 30 to 125 nucleotides, and more particularly preferably from 40 to 110 nucleotides. In particular, the total length of a gRNA may be from 50 to 140 nucleotides, preferably from 80 to 125 nucleotides, and more particularly preferably from 90 to 110 nucleotides. According to a particular embodiment, a gRNA as used in the present invention has a length of 102 nucleotides.

The person skilled in the art can easily define the sequence and structure of the gRNAs according to the chromosomal region to be targeted using well-known techniques (see for example the paper by Di Carlo et al., 2013 Nucleic Acids Research, pp. 1-8).

In the process according to the invention, one or more gRNAs may be used simultaneously. These gRNAs may be different or identical. These gRNAs may target identical or different, preferably different, chromosomal regions.

The gRNAs can be introduced into the eukaryotic cell in the form of mature gRNA molecules, in the form of precursors or in the form of one or more nucleic acids encoding said gRNAs. When the gRNA(s) are introduced into the cell directly in the form of RNA molecules (mature or precursor), these gRNAs may contain modified nucleotides or chemical modifications allowing them, for example, to increase their resistance to nucleases and thus to increase their life span in the cell. In particular, they may comprise at least one modified or unnatural nucleotide such as, for example, a nucleotide comprising a modified base, such as inosine, methyl-5-deoxycytidine, dimethylamino-5-deoxyuridine, deoxyuridine, diamino-2,6-purine, bromo-5-deoxyuridine or any other modified base allowing hybridization. The gRNAs used according to the invention can also be modified at the internucleotide linkage such as phosphorothioates, H-phosphonates or alkyl phosphonates, or at the backbone such as alpha-oligonucleotides, 2'-O-alkyl ribose or peptide nucleic acids (PNAs) (Egholm et al., 1992 J. Am. Chem. Soc., 114, pp. 1895-1897).

The gRNAs can be natural RNAs, synthetic RNAs, or RNAs produced by recombinant techniques. These gRNAs can be prepared by any methods known to the skilled person such as, for example, chemical synthesis, in vivo transcription, or amplification techniques.

According to an embodiment, the process comprises the introduction into the eukaryotic cell of the fusion protein and one or more gRNAs capable of targeting the action of the fusion protein to a given chromosomal region. The protein and the gRNAs can be introduced into the cytoplasm or nucleus of the eukaryotic cell by any method known to the skilled person, for example by microinjection. In particular, the fusion protein can be introduced into the cell as an element of a protein-RNA complex comprising at least one gRNA.

According to another embodiment, the process comprises the introduction into the eukaryotic cell of the fusion protein and one or more nucleic acids encoding one or more gRNAs.

According to yet another embodiment, the process comprises the introduction into the eukaryotic cell of a nucleic acid encoding the fusion protein and one or more gRNAs.

According to yet another embodiment, the process comprises the introduction into the eukaryotic cell of a nucleic acid encoding the fusion protein and one or more nucleic acids encoding one or more gRNAs.

According to an embodiment, the eukaryotic cell is heterozygous for the gene(s) targeted by the guide RNA(s).

According to another embodiment, the eukaryotic cell is homozygous for the gene(s) targeted by the guide RNA(s).

The fusion protein, or the nucleic acid encoding it, and the gRNA(s), or the nucleic acid(s) encoding them, can be introduced simultaneously or sequentially into the cell.

Plant transformation techniques are well known and described in the technical and scientific literature. These techniques aim at the transformation of plant cells from whole plants, callus, or protoplasts. These techniques include injection or microinjection (Griesbach (1987) Plant Sci. 50 pp. 69-77), DNA electroporation (Fromm et al.

(1985), Natl Acad Sci., USA 82, 5 pp. 824; Wan and Lemaux, Plant Physiol. 104 (1994), 37-48), biolistics (Klein et al. (1987) Nature 327 pp. 773), viral vector transfection (Gelvin, Nature Biotechnology 23, pp. 684-685 (2005)), bombardment (Sood et al., 2011, Biologia Plantarum, 55, 1 pp. -15), cell or protoplast fusion (Willmitzer, L., 1993, Transgenic plants. Biotechnology, vol. 2, pp. 627-659), agrotransfection by T-DNA insertion, in particular using *Agrobacterium tumefaciens* (Fraley et al. Crit. Rev. Plant. Sci. 1986, 4 pp. 1-46; Fromm et al., in Biotechnology (1990) 8, pp. 833-844) or *Agrobacterium rhizogenes* (Cho et al. (2000) Planta 210: pp. 195-204) or other bacterial hosts (Brootghaerts et al. (2005) Nature 433: pp. 629-633) using for example the floral dip technique (Clough and Bent Plant J. 1998 December; 16(6):735-43; Zale et al. Plant Cell Reports volume 28, pp. 903-913(2009)).

Alternatively, and more particularly concerning plant cells, the nucleic acid encoding the fusion protein and the nucleic acid(s) encoding the gRNA(s) can be introduced into a cell by crossing two cells into which the nucleic acid encoding the fusion protein and the nucleic acid(s) encoding the gRNA(s), respectively, have been introduced.

Alternatively, and more particularly concerning plant cells, the nucleic acid encoding the fusion protein and the nucleic acid(s) encoding the gRNA(s) may be introduced into a cell by mitosis of a cell into which the nucleic acid encoding the fusion protein and the nucleic acid(s) encoding the gRNA(s) have previously been introduced.

In embodiments wherein the fusion protein and/or the gRNA(s) are introduced into the eukaryotic cell in the form of a nucleic acid encoding said protein and/or gRNA(s), expression of said nucleic acids produces the fusion protein and/or the gRNA(s) in the cell.

The nucleic acids encoding the fusion protein and those encoding the gRNAs can be placed under the control of identical or different constitutive or inducible promoters, in particular meiosis-specific promoters. According to a preferred embodiment, the nucleic acids are placed under the control of constitutive promoters such as the ADH1 promoter or the RNA polymerase III-dependent pRPR1 and SNR52 promoters, most preferably the pRPR1 promoter.

The nature of the promoter may also depend on the nature of the eukaryotic cell. According to a particular embodiment, the eukaryotic cell is a plant cell, preferably a rice cell, and the nucleic acids are placed under the control of a promoter selected from the pZmUbi promoters (corn ubiquitin promoter) and the U3 and U6 polymerase III promoters. According to a preferred embodiment, the nucleic acid encoding the fusion protein is placed under the control of the pZmUbi promoter and the nucleic acids encoding the gRNAs are placed under the control of the U3 or U6 promoter, preferably the U3 promoter.

According to a particular aspect, gRNA expression is placed under the control of the tetracycline operator. The Tet system comprises two complementary circuits: the tTA dependent circuit (Tet-Off system) and the rtTA dependent circuit (Tet-On system). Preferably, gRNA expression is controlled by a Tet-On system. gRNA expression is thus regulated by the presence or absence of tetracycline or one of its derivatives such as doxycycline.

The nucleic acids encoding the fusion protein and the gRNA(s) may be arranged on the same construct, in particular on the same expression vector, or on separate constructs. Alternatively, the nucleic acids may be inserted into the eukaryotic cell genome at identical or distinct regions. According to a preferred embodiment, the nucleic acids encoding the fusion protein and the gRNA(s) are arranged on the same expression vector.

The nucleic acids as described above can be introduced into the eukaryotic cell by any method known to the skilled person, in particular by microinjection, transfection, agro-infection, electroporation or biolistics.

After introduction into the eukaryotic cell of the fusion protein and one or more gRNAs, or the nucleic acids encoding them, the process according to the invention comprises the induction of the entry into prophase I of meiosis of said cell.

This induction can be done according to different methods, well known to the skilled person.

By way of example, when the eukaryotic cell is a mouse cell, the entry of cells into prophase I of meiosis can be induced by the addition of retinoic acid (Bowles J et al., 2006, Science, 312(5773), pp. 596-600).

When the eukaryotic cell is a plant cell, the induction of meiosis occurs according to a natural process. According to a particular embodiment, after transformation of a callus comprising one or more plant cells, a plant is regenerated and placed in conditions favoring the induction of a reproductive phase and thus of the meiosis process. These conditions are well known to the skilled person.

When the eukaryotic cell is yeast, this induction can be achieved by transferring the yeast into a sporulation medium, in particular from a rich medium to a sporulation medium, said sporulation medium preferably lacking a fermentable carbon or nitrogen source, and incubating the yeast in the sporulation medium for a time sufficient to induce double-strand breaks. Initiation of the meiotic cycle depends on several signals: the presence of the two sex-type alleles MATa and MATα, the absence of a source of nitrogen and fermentable carbon.

As used in this document, the term 'rich medium' refers to a culture medium comprising a source of fermentable carbon and a source of nitrogen, as well as all the nutrients necessary for yeast to multiply by mitotic division. This medium can be easily chosen by the skilled person and can, for example, be selected from the group consisting of YPD medium (1% yeast extract, 2% bactopeptone, and 2% glucose), YPG medium (1% yeast extract, 2% bactopeptone, and 3% glycerol) and a synthetic complete (SC) medium (Treco and Lundblad, 2001, Curr. Protocol. Mol. Biol., Chapter 13, Unit 13.1).

As used herein, the term 'sporulation medium' refers to any medium that induces the entry into meiosis prophase of yeast cells without vegetative growth, in particular to a culture medium that does not include a fermentable carbon source or a nitrogen source but does include a source of carbon that can be metabolized by respiration such as acetate. This medium can be easily selected by the skilled person and can, for example, be selected from the group consisting of KAc 1% medium (Wu and Lichten, 1994, Science, 263, pp. 515-518), SPM medium (Kassir and Simchen, 1991, Meth. Enzymol., 194, pp. 94-110) and the sporulation media described in the paper by Sherman (Sherman, Meth. Enzymol., 1991, 194, 3-21).

According to a preferred embodiment, before being incubated in the sporulation medium, the cells are grown for a few division cycles in a pre-sporulation medium so as to obtain efficient and synchronous sporulation. The pre-sporulation medium can be easily chosen by the person skilled in the art. This medium can be, for example, the SPS medium (Wu and Lichten, 1994, Science, 263, pp. 515-518).

The choice of media (rich medium, pre-sporulation medium, sporulation medium) depends on the physiological and genetic traits of the yeast strain, particularly if the strain is auxotrophic for one or more compounds.

Once the cell has entered prophase I of meiosis, the meiotic process can continue until four daughter cells with the desired recombinations are produced.

Alternatively, when the eukaryotic cell is a yeast, and in particular a yeast of the genus *Saccharomyces*, the cells can be returned to growth conditions to resume a mitotic process. This phenomenon, called 'return-to-growth' or 'RTG', has been previously described in patent application WO 2014/083142 and occurs when cells that entered meiosis in response to nutritional deficiency are returned to the presence of a carbon and nitrogen source after the formation of Spo11-dependent double-strand breaks but before the first division of meiosis (Honigberg and Esposito, Proc. Nat. Acad. Sci USA, 1994, 91, pp. 6559-6563). Under these conditions, they interrupt their progression through the stages of meiotic differentiation to resume a mitotic growth mode while inducing the recombinations sought during the repair of double-strand breaks (Sherman and Roman, Genetics, 1963, 48, 255-261; Esposito and Esposito, Proc. Nat. Acad. Sci, 1974, 71, pp. 3172-3176; Zenvirth et al., 1997 Genes to Cells, 2, pp. 487-498).

The process may further comprise obtaining the cell(s) having the desired recombination(s). When the cell is a yeast cell, the process may further comprise a step of culturing and/or multiplying the cell or cells having the desired recombination(s). When the cell is a plant cell, the process may further comprise a somatic embryogenesis step, i.e., the regeneration of a plant embryo from a callus comprising the cells having the desired recombination(s).

The process according to the invention can be used in all applications where it is desirable to improve and control meiotic recombination phenomena. In particular, the invention makes it possible to associate, in a preferential manner, genetic traits of interest. This preferential association makes it possible, on the one hand, to reduce the time required for their selection, and on the other hand, to generate possible but unlikely natural combinations. Finally, according to the chosen embodiment, the organisms obtained by this process can be considered as non-genetically modified (non-GMO) organisms.

According to another aspect, the present invention relates to a process for generating variants of a eukaryotic organism, with the exception of humans, preferably a yeast or a plant, even more preferably a yeast, in particular a yeast strain of industrial interest, comprising introduction into a cell of said organism of:
  a) a fusion protein, a nucleic acid, an expression cassette, or a vector as described above; and
  b) one or more guide RNAs or one or more nucleic acids encoding said guide RNAs, said guide RNAs comprising a nuclease binding RNA structure associated with a CRISPR system of the fusion protein and a sequence complementary to the targeted chromosomal region; and
  induction of entry into prophase I of meiosis of said cell;
  obtaining cell(s) with the desired recombination(s) in the targeted chromosomal region(s); and
  genesis of a variant of the organism from said recombinant cell.

In this process, the term 'variant' is to be understood broadly to mean an organism with at least one genotypic or phenotypic difference from the parent organisms.

Recombinant cells can be obtained by allowing meiosis to continue until spores are obtained, or, in the case of yeast, by returning the cells to growth conditions after the induction of double-strand breaks in order to resume a mitotic process.

When the eukaryotic cell is a plant cell, a plant variant can be generated by fusion of plant gametes, at least one of the gametes being a cell recombined by the method according to the invention.

The present invention also relates to a process for identifying or locating genetic information encoding a trait of interest in a eukaryotic cell genome, preferably a yeast or plant, comprising:

introduction into the eukaryotic cell of:

a) a fusion protein, a nucleic acid, an expression cassette, or a vector as described above; and b) one or more guide RNAs or one or more nucleic acids encoding said guide RNAs, said guide RNAs comprising a nuclease binding RNA structure associated with a CRISPR system of the fusion protein and a sequence complementary to the targeted chromosomal region; and induction of entry into prophase I of meiosis of said cell;

obtaining cell(s) with the desired recombination(s) in the targeted chromosomal region(s); and analysis of the genotypes and phenotypes of the recombinant cells in order to identify or locate the genetic information encoding the trait of interest.

Preferably, the trait of interest is a quantitative trait of interest (QTL). A quantitative trait locus (QTL) is a variably sized region of DNA that is closely associated with a quantitative trait, i.e., a chromosomal region where one or more genes responsible for the trait in question are located. These quantitative traits usually relate to a phenotypic trait. QTL analysis allows the link between a genetic variation and a phenotypic variation to be assessed.

The present invention finally relates to a kit comprising a fusion protein, a nucleic acid, an expression cassette, or an expression vector according to the invention, or a host cell transformed or transfected with a nucleic acid, an expression cassette, or an expression vector according to the invention. It also relates to the use of said kit to implement a process according to the invention, in particular to (i) induce targeted meiotic recombinations in a eukaryotic cell, (ii) generate variants of a eukaryotic organism, and/or (iii) identify or locate genetic information encoding a trait of interest in a eukaryotic cell genome.

In the peptide sequences described in this document, the amino acids are represented by their one-letter code according to the following nomenclature: C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan and Y: tyrosine.

In certain embodiments, all the identity percentages mentioned in this application may be fixed at at least 90%, at least 95%, at least 96%, at least 97%, at least 98% or at least 99%, identity. In particular, the embodiments in which all the percentages of sequence identity are at least 90%, at least 95%, at least 96%, at least 97%, at least 98% or at least 99%, sequence identity are considered as being described.

The following examples are presented for illustrative and non-limiting purposes and serve to illustrate the invention.

EXAMPLES

Materials and Methods

Construction of the $P_{ADH1}$-NLS-SpdCAS9-SPO11$^{Y135F}$-6× His-3×Flag-T$_{ADH1}$ Cassette The SPO11-Y135F mutation (Bergerat, et al. 1997 Nature, 386, 4 pp. 14-417, SEQ ID NO: 2) was introduced by site-directed mutagenesis into the SPO11 gene sequence contained in the $P_{ADH1}$-NLS-SpdCAS9-SPO11-6×His-3× Flag-TADH1 fragment of the plasmid pAS504 (Sarno, et al. 2017 Nucleic acids research, 45, e164), creating the plasmid pAS533. The sequence of the protein SpdCAS9 corresponds to SEQ ID NO: 38 with two point mutations: D10A and H840A.

Construction of the sgRNA Expression Plasmid for dCas9

The sgRNA expression plasmid (pAS507) directing the SpdCas9 protein to the Gal4$_{UAS-D/E}$ target sequence located in the GAL2 gene promoter was described in the publication (Sarno, et al. 2017 Nucleic acids research, 45, e164).

Construction of *Saccharomyces cerevisiae* Yeast Strains.

Genotype of the *Saccharomyces cerevisiae* Strains Used:

AND3482: MATa/α trp1/trp1::hisG pGAL2_AB²CD₂E/ pGAL2_ab₂cD₂E tGAL2::HphMX/-pEMP46:: NatMX/-his4/"leu2/"ura3/"

AND2549: MATa/α trp1/trp1::hisG tGAL2::HphMX/- pEMP46::NatMX/-his4/"leu2/"ura3/"

AND3596: MATa/α trp1::pAS533(dCAS9-SPO11$^{Y135F}$- 6×His-Flag-TRP1-KanMX)/trp1::hisG tGAL2:: HphMX/-pEMP46::NatMX/-his4/"leu2/"ura3/"

ANT3029: MATa/α trp1::pAS533(dCAS9-SPO11$^{Y135F}$- 6×His-Flag-TRP1-KanMX)/trp1::hisG tGAL2:: HphMX/-pEMP46::NatMX/-his4/"leu2/"ura3/"+plasmid pAS507-sgRNA$_{UAS-D/E}$::LEU2.

The introduction of $P_{ADH1}$-SpdCAS9-SPO11$^{Y135F}$-6× His-Flag-T$_{ADH1}$-TRP1-KanMX cassettes into the yeast *S. cerevisiae* genome was performed as described by (Sarno, et al. 2017 Nucleic acids research, 45, e164). Plasmids pAS533 and pAS628 carrying the $P_{ADH1}$-SpdCAS9-SPO11$^{Y135F}$-6× His-Flag-T$_{ADH1}$-TRP1-KanMX cassettes were linearized by the XbaI restriction enzyme and integrated at the TRP1 locus by cell electroporation.

The sgRNA and crRNA expression plasmids carrying the LEU2 selection marker were introduced into *S. cerevisiae* AND3535, AND3538, AND3596 cells auxotrophic for leucine (leu2⁻) by electroporation and the transformants selected on plates containing synthetic complete medium lacking leucine. Integration junctions of SpdCAS9-SPO11$^{Y135F}$ expression cassettes at the TRP1 locus were verified by PCR.

Recombination frequency around the GAL2 gene (chromosome XII) is measured between the NatMX cassette integrated into the EMP46 gene promoter (pEMP46) (position 287 725) and the HphMX cassette integrated at position 292 068 into the GAL2 gene terminator (tGAL2).

Induction of Meiosis and Sporulation

First, diploid cells are inoculated in a rich liquid medium (YPD) or in a synthetic complete medium lacking leucine (SC-Leu) in order to maintain the plasmids carrying the LEU2 selection marker. Cells are grown under shaking at 30° C. for 24 hours ('Mitotic' point). Then the saturated SC-Leu liquid cultures are diluted in SPS pre-sporulation medium (2-16×10⁵ cells/ml) and cultured under shaking at 30° C. for ~15 hours. Cultures having reached an OD₆₀₀ between 2 and 4 are centrifuged, washed twice with water, and transferred to sporulation medium (KAc 1%) with a final OD₆₀₀ of 1. This is point T₀ of meiotic progression. To induce expression of crRNAs doxycycline hyclate is added to a final concentration of 10 μg/ml in the sporulation medium at time T₀.

Growth and Sporulation Media

YPD, SPS pre-sporulation, and KAc 1% sporulation media are described in the reference Murakami et al., 2009 Methods Mol Biol, 557, pp. 117-142. YPD medium consists of yeast extract (1%), peptone (2%), and glucose (2%). Synthetic complete medium without leucine is composed of yeast nitrogen base (0.17%), ammonium sulphate (0.5%), synthetic drop-out mix without leucine (0.16%), and glucose (2%).

Southern Blot and Quantifications of DSBs and Recombinant Molecules

Genomic DNA extraction as well as detection of DSBs and recombinant molecules by Southern blot were performed as described in the references Murakami et al., 2009 Methods Mol Biol, 557, pp. 117-142, and Sarno et al., 2017 Nucleic acids research, 45, e164.

Genetic Analysis of Tetrads.

Four-spore tetrads were dissected on YPD plates after 48 hours of incubation in sporulation medium. Segregation of NatMX and HygMX markers is visualized by replicating colonies on YPD plates containing nourseothricin (100 mg/l) or hygromycin (300 mg/l), respectively.

Results

The dCas9-Spo11$^{Y135F}$ fusion stimulates the formation of recombinant molecules in the GAL2 locus region (FIG. 1).

Recombination analysis by Southern blot was performed as indicated in the legend for FIG. 1. The dCas9 sgRNA target region is located in the GAL2 gene promoter at the Gal4$_{UASD/E}$ binding sites.

The genotype of the wild-type strain (AND2549) is MATa/α trp1/trp1::hisG tGAL2::HphMX/-pEMP46::NatMX/-his4/"leu2/"ura3/"

The genotype of the dCAS9-SPO11$^{Y135F}$ strain (ANT3029) is MATa/α trp1::pAS33(dCAS9-SPO11$^{Y135F}$-6×His-Flag-TRP1-KanMX)/trp1::hisG tGAL2::HphMX/-pEMP46::NatMX/-his4/"leu2/"ura3/" and contains the plasmid pAS507-sgRNA$_{UAS-D/E}$::LEU2.

---

The invention claimed is:

1. A fusion protein, or a nucleic acid encoding the fusion protein, wherein the fusion protein comprises:
   (i) a class II type II CRISPR nuclease that has deficient nuclease activity as compared to a wild-type class II type II nuclease; and
   (ii) a Spo11 protein that has deficient nuclease activity as compared to a wild-type Spo11 protein.

2. The fusion protein of claim 1, wherein the class II type II nuclease is a Cas9 nuclease.

3. The fusion protein of claim 1, wherein the class II type II nuclease comprises a polypeptide sequence having at least 80% identity to a sequence selected from the group consisting of SEQ ID NO: 38, SEQ ID NO: 39, SEQ ID NO: 40, SEQ ID NO: 41, SEQ ID NO: 42, and SEQ ID NO: 43.

4. The fusion protein of claim 3, wherein the polypeptide sequence comprises an amino acid substitution at a position corresponding to D10 in SEQ ID NO: 38 and/or an amino acid substitution at a position corresponding to H840 in SEQ ID NO: 38.

5. The fusion protein of claim 4, wherein the amino acid substitution at the position corresponding to D10 in SEQ ID NO: 38 comprises an alanine substitution, and wherein the amino acid substitution at the position corresponding to H840 in SEQ ID NO: 48 comprises an alanine substitution.

6. The fusion protein of claim 1, wherein the class II type II CRISPR nuclease has no nuclease activity and is capable of interacting with a guide RNA.

7. The fusion protein of claim 1, wherein the Spo11 protein comprises a polypeptide sequence having at least 80% identity to a sequence selected from the group consisting of SEQ ID NO: 1, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 20, SEQ ID NO: 21, SEQ ID NO: 46, SEQ ID NO: 47, and SEQ ID NO: 48.

8. The fusion protein of claim 7, wherein the polypeptide sequence comprises an amino acid substitution at a position corresponding to Y135 in SEQ ID NO: 1.

9. The fusion protein of claim 8, wherein the amino acid substitution at the position corresponding to Y135 in SEQ ID NO: 1 comprises a phenylalanine substitution.

10. The fusion protein of claim 1, wherein the Spo11 protein has no nuclease activity.

11. The fusion protein of claim 1, wherein the Spo11 protein is from *Capsicum baccatum*.

12. A nucleic acid encoding the fusion protein of claim 1.

13. An expression cassette or vector comprising the nucleic acid of claim 12 operably linked to a transcriptional promoter allowing expression of the fusion protein.

14. The expression cassette or vector of claim 13, wherein the fusion protein is expressed during meiosis.

15. A non-human host cell comprising the fusion protein of claim 1 or a nucleic acid encoding the fusion protein.

16. The non-human host cell of claim 15, wherein the host cell is a plant cell, a yeast cell or a fungal cell.

17. A process for inducing targeted meiotic recombination(s) in a eukaryotic cell, comprising:
   expressing in the eukaryotic cell:
   a) the fusion protein of claim 1; and
   b) one or more guide RNAs or one or more nucleic acids encoding the guide RNAs, wherein each of the one or more guide RNAs comprises (i) a nuclease binding RNA structure associated with a class II type II CRISPR system, and (ii) a sequence complementary to a targeted chromosomal region.

18. The process of claim 17, wherein the eukaryotic cell is a yeast cell.

19. The process of claim 17, wherein the eukaryotic cell is a plant cell.

20. The process of claim 17, wherein the class II type II CRISPR nuclease of the fusion protein is a Cas9 nuclease.

21. The process of claim 17, wherein the class II type II CRISPR nuclease of the fusion protein comprises a polypeptide sequence having at least 80% identity to a sequence selected from the group consisting of SEQ ID NO: 38, SEQ ID NO: 39, SEQ ID NO: 40, SEQ ID NO: 41, SEQ ID NO: 42, and SEQ ID NO: 43.

22. The process of claim 21, wherein the polypeptide sequence comprises an amino acid substitution at a position corresponding to D10 in SEQ ID NO: 38 and/or an amino acid substitution at a position corresponding to H840 in SEQ ID NO: 38.

23. The process of claim 22, wherein the amino acid substitution at the position corresponding to D10 in SEQ ID NO: 38 comprises an alanine substitution, and wherein the amino acid substitution at the position corresponding to H840 in SEQ ID NO: 48 comprises an alanine substitution.

24. The process of claim 17, wherein the Spo11 protein of the fusion protein comprises a polypeptide sequence having at least 80% identity to a sequence selected from the group consisting of SEQ ID NO: 1, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 20, SEQ ID NO: 21, SEQ ID NO: 46, SEQ ID NO: 47, and SEQ ID NO: 48.

25. The process of claim 24, wherein the polypeptide sequence comprises an amino acid substitution at a position corresponding to Y135 in SEQ ID NO: 1.

26. The process of claim 25, wherein the amino acid substitution at the position corresponding to Y135 in SEQ ID NO: 1 comprises a phenylalanine substitution.

27. The process of claim 17, wherein the Spo11 protein is from *Capsicum baccatum*.

28. A process for generating variants of a eukaryotic organism, comprising:

expressing in a cell of the eukaryotic organism:

a) the fusion protein of claim 1; and b) one or more guide RNAs or one or more nucleic acids encoding the guide RNAs, wherein each of the one or more guide RNAs comprises (i) a nuclease binding RNA structure associated with a class II type II CRISPR system, and (ii) a sequence complementary to a targeted chromosomal region;

obtaining cell(s) having the desired recombination(s) in the targeted chromosomal region(s); and generating a variant of the organism from the recombinant cell(s).

29. A process for identifying or locating genetic information encoding a trait of interest in a eukaryotic cell genome, comprising:

expressing in the eukaryotic cell:

a) the fusion protein of claim 1; and b) one or more guide RNAs or one or more nucleic acids encoding the guide RNAs, wherein each of the one or more guide RNAs comprises (i) a nuclease binding RNA structure associated with a class II type II CRISPR system, and (ii) a sequence complementary to a targeted chromosomal region;

obtaining cell(s) having the desired recombination(s) in the targeted chromosomal region(s); and analysis of the genotypes and phenotypes of the recombinant cell(s) in order to identify or locate the genetic information encoding a trait of interest.

30. The process of claim 29, wherein the trait of interest is a quantitative trait of interest (QTL).

\* \* \* \* \*

SEQUENCE LISTING

<160> NUMBER OF SEQ ID NOS: 54

<210> SEQ ID NO 1
<211> LENGTH: 398
<212> TYPE: PRT
<213> ORGANISM: Saccharomyces cerevisiae

<400> SEQUENCE: 1

```
Met Ala Leu Glu Gly Leu Arg Lys Lys Tyr Lys Thr Arg Gln Glu Leu
1               5                   10                  15

Val Lys Ala Leu Thr Pro Lys Arg Arg Ser Ile His Leu Asn Ser Asn
            20                  25                  30

Gly His Ser Asn Gly Thr Pro Cys Ser Asn Ala Asp Val Leu Ala His
        35                  40                  45

Ile Lys His Phe Leu Ser Leu Ala Ala Asn Ser Leu Glu Gln His Gln
    50                  55                  60

Gln Pro Ile Ser Ile Val Phe Gln Asn Lys Lys Lys Lys Gly Asp Thr
65                  70                  75                  80

Ser Ser Pro Asp Ile His Thr Thr Leu Asp Phe Pro Leu Asn Gly Pro
            85                  90                  95

His Leu Cys Thr His Gln Phe Lys Leu Lys Arg Cys Ala Ile Leu Leu
            100                 105                 110

Asn Leu Leu Lys Val Val Met Glu Lys Leu Pro Leu Gly Lys Asn Thr
            115                 120                 125

Thr Val Arg Asp Ile Phe Tyr Ser Asn Val Glu Leu Phe Gln Arg Gln
    130                 135                 140

Ala Asn Val Val Gln Trp Leu Asp Val Ile Arg Phe Asn Phe Lys Leu
145                 150                 155                 160

Ser Pro Arg Lys Ser Leu Asn Ile Ile Pro Ala Gln Lys Gly Leu Val
                165                 170                 175

Tyr Ser Pro Phe Pro Ile Asp Ile Tyr Asp Asn Ile Leu Thr Cys Glu
            180                 185                 190

Asn Glu Pro Lys Met Gln Lys Gln Thr Ile Phe Pro Gly Lys Pro Cys
            195                 200                 205

Leu Ile Pro Phe Phe Gln Asp Asp Ala Val Ile Lys Leu Gly Thr Thr
    210                 215                 220

Ser Met Cys Asn Ile Val Ile Val Glu Lys Glu Ala Val Phe Thr Lys
225                 230                 235                 240

Leu Val Asn Asn Tyr His Lys Leu Ser Thr Asn Thr Met Leu Ile Thr
                245                 250                 255
```

```
Gly Lys Gly Phe Pro Asp Phe Leu Thr Arg Leu Phe Leu Lys Lys Leu
            260             265             270

Glu Gln Tyr Cys Ser Lys Leu Ile Ser Asp Cys Ser Ile Phe Thr Asp
            275             280             285

Ala Asp Pro Tyr Gly Ile Ser Ile Ala Leu Asn Tyr Thr His Ser Asn
            290             295             300

Glu Arg Asn Ala Tyr Ile Cys Thr Met Ala Asn Tyr Lys Gly Ile Arg
305             310             315             320

Ile Thr Gln Val Leu Ala Gln Asn Asn Glu Val His Asn Lys Ser Ile
            325             330             335

Gln Leu Leu Ser Leu Asn Gln Arg Asp Tyr Ser Leu Ala Lys Asn Leu
            340             345             350

Ile Ala Ser Leu Thr Ala Asn Ser Trp Asp Ile Ala Thr Ser Pro Leu
            355             360             365

Lys Asn Val Ile Ile Glu Cys Gln Arg Glu Ile Phe Phe Gln Lys Lys
            370             375             380

Ala Glu Met Asn Glu Ile Asp Ala Arg Ile Phe Glu Tyr Lys
385             390             395

<210> SEQ ID NO 2
<211> LENGTH: 398
<212> TYPE: PRT
<213> ORGANISM: artificial
<220> FEATURE:
<223> OTHER INFORMATION: Spo11-Y135F Saccharomyces cerevisiae

<400> SEQUENCE: 2

Met Ala Leu Glu Gly Leu Arg Lys Lys Tyr Lys Thr Arg Gln Glu Leu
1               5               10              15

Val Lys Ala Leu Thr Pro Lys Arg Arg Ser Ile His Leu Asn Ser Asn
            20              25              30

Gly His Ser Asn Gly Thr Pro Cys Ser Asn Ala Asp Val Leu Ala His
            35              40              45

Ile Lys His Phe Leu Ser Leu Ala Ala Asn Ser Leu Glu Gln His Gln
            50              55              60

Gln Pro Ile Ser Ile Val Phe Gln Asn Lys Lys Lys Gly Asp Thr
65              70              75              80

Ser Ser Pro Asp Ile His Thr Thr Leu Asp Phe Pro Leu Asn Gly Pro
            85              90              95

His Leu Cys Thr His Gln Phe Lys Leu Lys Arg Cys Ala Ile Leu Leu
            100             105             110

Asn Leu Leu Lys Val Val Met Glu Lys Leu Pro Leu Gly Lys Asn Thr
            115             120             125

Thr Val Arg Asp Ile Phe Phe Ser Asn Val Glu Leu Phe Gln Arg Gln
            130             135             140

Ala Asn Val Val Gln Trp Leu Asp Val Ile Arg Phe Asn Phe Lys Leu
145             150             155             160

Ser Pro Arg Lys Ser Leu Asn Ile Ile Pro Ala Gln Lys Gly Leu Val
            165             170             175

Tyr Ser Pro Phe Pro Ile Asp Ile Tyr Asp Asn Ile Leu Thr Cys Glu
            180             185             190

Asn Glu Pro Lys Met Gln Lys Gln Thr Ile Phe Pro Gly Lys Pro Cys
            195             200             205

Leu Ile Pro Phe Phe Gln Asp Asp Ala Val Ile Lys Leu Gly Thr Thr
            210             215             220
```

```
Ser Met Cys Asn Ile Val Ile Val Glu Lys Glu Ala Val Phe Thr Lys
225                 230                 235                 240

Leu Val Asn Asn Tyr His Lys Leu Ser Thr Asn Thr Met Leu Ile Thr
                245                 250                 255

Gly Lys Gly Phe Pro Asp Phe Leu Thr Arg Leu Phe Leu Lys Lys Leu
                260                 265                 270

Glu Gln Tyr Cys Ser Lys Leu Ile Ser Asp Cys Ser Ile Phe Thr Asp
                275                 280                 285

Ala Asp Pro Tyr Gly Ile Ser Ile Ala Leu Asn Tyr Thr His Ser Asn
                290                 295                 300

Glu Arg Asn Ala Tyr Ile Cys Thr Met Ala Asn Tyr Lys Gly Ile Arg
305                 310                 315                 320

Ile Thr Gln Val Leu Ala Gln Asn Asn Glu Val His Asn Lys Ser Ile
                325                 330                 335

Gln Leu Leu Ser Leu Asn Gln Arg Asp Tyr Ser Leu Ala Lys Asn Leu
                340                 345                 350

Ile Ala Ser Leu Thr Ala Asn Ser Trp Asp Ile Ala Thr Ser Pro Leu
                355                 360                 365

Lys Asn Val Ile Ile Glu Cys Gln Arg Glu Ile Phe Phe Gln Lys Lys
                370                 375                 380

Ala Glu Met Asn Glu Ile Asp Ala Arg Ile Phe Glu Tyr Lys
385                 390                 395
```

```
<210> SEQ ID NO 3
<211> LENGTH: 1300
<212> TYPE: PRT
<213> ORGANISM: Francisella novicida

<400> SEQUENCE: 3

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
                20                  25                  30

Ala Arg Gly Leu Ile Leu Asp Asp Glu Lys Arg Ala Lys Asp Tyr Lys
                35                  40                  45

Lys Ala Lys Gln Ile Ile Asp Lys Tyr His Gln Phe Phe Ile Glu Glu
                50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
                100                 105                 110

Ile Lys Asp Ser Glu Lys Phe Lys Asn Leu Phe Asn Gln Asn Leu Ile
                115                 120                 125

Asp Ala Lys Lys Gly Gln Glu Ser Asp Leu Ile Leu Trp Leu Lys Gln
                130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
                180                 185                 190

Asn Asp Ile Pro Thr Ser Ile Ile Tyr Arg Ile Val Asp Asp Asn Leu
                195                 200                 205
```

-continued

```
Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
                260                 265                 270

Leu Asn Gln Ser Gly Ile Thr Lys Phe Asn Thr Ile Ile Gly Gly Lys
            275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
                340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
                420                 425                 430

Pro Ser Lys Lys Glu Gln Glu Leu Ile Ala Lys Lys Thr Glu Lys Ala
            435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
            515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
            595                 600                 605

Trp Asp Lys Asn Lys Glu Pro Asp Asn Thr Ala Ile Leu Phe Ile Lys
    610                 615                 620
```

```
Asp Asp Lys Tyr Tyr Leu Gly Val Met Asn Lys Lys Asn Asn Lys Ile
625             630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Ser Pro Gln
            690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
                740                 745                 750

Phe Tyr Arg Glu Val Glu Asn Gln Gly Tyr Lys Leu Thr Phe Glu Asn
            755                 760                 765

Ile Ser Glu Ser Tyr Ile Asp Ser Val Val Asn Gln Gly Lys Leu Tyr
            770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
            835                 840                 845

Ile Ala Asn Lys Asn Lys Asp Asn Pro Lys Lys Glu Ser Val Phe Glu
            850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
            930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn  Ala Ile Val Val Phe  Glu Asp Leu
            995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
```

-continued

```
            1040                1045                1050

Ala Tyr  Gln Leu Thr Ala Pro  Phe Glu Thr Phe Lys  Lys Met Gly
    1055                1060                1065

Lys Gln  Thr Gly Ile Ile Tyr  Tyr Val Pro Ala Gly  Phe Thr Ser
    1070                1075                1080

Lys Ile  Cys Pro Val Thr Gly  Phe Val Asn Gln Leu  Tyr Pro Lys
    1085                1090                1095

Tyr Glu  Ser Val Ser Lys Ser  Gln Glu Phe Phe Ser  Lys Phe Asp
    1100                1105                1110

Lys Ile  Cys Tyr Asn Leu Asp  Lys Gly Tyr Phe Glu  Phe Ser Phe
    1115                1120                1125

Asp Tyr  Lys Asn Phe Gly Asp  Lys Ala Ala Lys Gly  Lys Trp Thr
    1130                1135                1140

Ile Ala  Ser Phe Gly Ser Arg  Leu Ile Asn Phe Arg  Asn Ser Asp
    1145                1150                1155

Lys Asn  His Asn Trp Asp Thr  Arg Glu Val Tyr Pro  Thr Lys Glu
    1160                1165                1170

Leu Glu  Lys Leu Leu Lys Asp  Tyr Ser Ile Glu Tyr  Gly His Gly
    1175                1180                1185

Glu Cys  Ile Lys Ala Ala Ile  Cys Gly Glu Ser Asp  Lys Lys Phe
    1190                1195                1200

Phe Ala  Lys Leu Thr Ser Val  Leu Asn Thr Ile Leu  Gln Met Arg
    1205                1210                1215

Asn Ser  Lys Thr Gly Thr Glu  Leu Asp Tyr Leu Ile  Ser Pro Val
    1220                1225                1230

Ala Asp  Val Asn Gly Asn Phe  Phe Asp Ser Arg Gln  Ala Pro Lys
    1235                1240                1245

Asn Met  Pro Gln Asp Ala Asp  Ala Asn Gly Ala Tyr  His Ile Gly
    1250                1255                1260

Leu Lys  Gly Leu Met Leu Leu  Gly Arg Ile Lys Asn  Asn Gln Glu
    1265                1270                1275

Gly Lys  Lys Leu Asn Leu Val  Ile Lys Asn Glu Glu  Tyr Phe Glu
    1280                1285                1290

Phe Val  Gln Asn Arg Asn Asn
    1295                1300
```

<210> SEQ ID NO 4
<211> LENGTH: 1229
<212> TYPE: PRT
<213> ORGANISM: Lachnospiraceae bacterium

<400> SEQUENCE: 4

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
            85                  90                  95
```

-continued

```
Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
        130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
            195                 200                 205

Ile Leu Asn Ser Asp Tyr Asp Val Glu Asp Phe Phe Glu Gly Glu Phe
        210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
            275                 280                 285

Phe Tyr Gly Glu Gly Tyr Thr Ser Asp Glu Glu Val Leu Glu Val Phe
        290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
            355                 360                 365

Ile His Leu Lys Lys Lys Ala Val Val Thr Glu Lys Tyr Glu Asp Asp
        370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
        450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
```

43

44

-continued

```
            515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
                820                 825                 830

Arg Gly Glu Arg Asn Leu Leu Tyr Ile Val Val Val Asp Gly Lys Gly
            835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
            915                 920                 925

Ser Gly Phe Lys Asn Ser Arg Val Lys Val Glu Lys Gln Val Tyr Gln
    930                 935                 940
```

-continued

```
Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
            995                 1000                1005

Gly Phe Val Asn Leu Leu Lys  Thr Lys Tyr Thr Ser  Ile Ala Asp
    1010                1015                1020

Ser Lys  Lys Phe Ile Ser Ser  Phe Asp Arg Ile Met  Tyr Val Pro
    1025                1030                1035

Glu Glu  Asp Leu Phe Glu Phe  Ala Leu Asp Tyr Lys  Asn Phe Ser
    1040                1045                1050

Arg Thr  Asp Ala Asp Tyr Ile  Lys Lys Trp Lys Leu  Tyr Ser Tyr
    1055                1060                1065

Gly Asn  Arg Ile Arg Ile Phe  Arg Asn Pro Lys Lys  Asn Asn Val
    1070                1075                1080

Phe Asp  Trp Glu Glu Val Cys  Leu Thr Ser Ala Tyr  Lys Glu Leu
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125

Ala Leu  Met Ser Leu Met Leu  Gln Met Arg Asn Ser  Ile Thr Gly
    1130                1135                1140

Arg Thr  Asp Val Asp Phe Leu  Ile Ser Pro Val Lys  Asn Ser Asp
    1145                1150                1155

Gly Ile  Phe Tyr Asp Ser Arg  Asn Tyr Glu Ala Gln  Glu Asn Ala
    1160                1165                1170

Ile Leu  Pro Lys Asn Ala Asp  Ala Asn Gly Ala Tyr  Asn Ile Ala
    1175                1180                1185

Arg Lys  Val Leu Trp Ala Ile  Gly Gln Phe Lys Lys  Ala Glu Asp
    1190                1195                1200

Glu Lys  Leu Asp Lys Val Lys  Ile Ala Ile Ser Asn  Lys Glu Trp
    1205                1210                1215

Leu Glu  Tyr Ala Gln Thr Ser  Val Lys His Lys
    1220                1225

<210> SEQ ID NO 5
<211> LENGTH: 1300
<212> TYPE: PRT
<213> ORGANISM: artificial
<220> FEATURE:
<223> OTHER INFORMATION: dead FnCpf1

<400> SEQUENCE: 5

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60
```

```
Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
            115                 120                 125

Asp Ala Lys Lys Gly Gln Glu Ser Asp Leu Ile Leu Trp Leu Lys Gln
        130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
            195                 200                 205

Pro Lys Phe Leu Glu Asn Lys Ala Lys Tyr Glu Ser Leu Lys Asp Lys
        210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
            275                 280                 285

Phe Val Asn Gly Glu Asn Thr Lys Arg Lys Gly Ile Asn Glu Tyr Ile
        290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Asp Leu Lys Ala Gln
        370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
            405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
        450                 455                 460

Lys His Arg Asp Ile Asp Lys Gln Cys Arg Phe Glu Glu Ile Leu Ala
465                 470                 475                 480
```

-continued

```
Asn Phe Ala Ala Ile Pro Met Ile Phe Asp Glu Ile Ala Gln Asn Lys
                485             490             495

Asp Asn Leu Ala Gln Ile Ser Ile Lys Tyr Gln Asn Gln Gly Lys Lys
            500             505             510

Asp Leu Leu Gln Ala Ser Ala Glu Asp Asp Val Lys Ala Ile Lys Asp
            515             520             525

Leu Leu Asp Gln Thr Asn Asn Leu Leu His Lys Leu Lys Ile Phe His
        530             535             540

Ile Ser Gln Ser Glu Asp Lys Ala Asn Ile Leu Asp Lys Asp Glu His
545             550             555             560

Phe Tyr Leu Val Phe Glu Glu Cys Tyr Phe Glu Leu Ala Asn Ile Val
                565             570             575

Pro Leu Tyr Asn Lys Ile Arg Asn Tyr Ile Thr Gln Lys Pro Tyr Ser
            580             585             590

Asp Glu Lys Phe Lys Leu Asn Phe Glu Asn Ser Thr Leu Ala Asn Gly
            595             600             605

Trp Asp Lys Asn Lys Glu Pro Asp Asn Thr Ala Ile Leu Phe Ile Lys
        610             615             620

Asp Asp Lys Tyr Tyr Leu Gly Val Met Asn Lys Lys Asn Asn Lys Ile
625             630             635             640

Phe Asp Asp Lys Ala Ile Lys Glu Asn Lys Gly Glu Gly Tyr Lys Lys
            645             650             655

Ile Val Tyr Lys Leu Leu Pro Gly Ala Asn Lys Met Leu Pro Lys Val
            660             665             670

Phe Phe Ser Ala Lys Ser Ile Lys Phe Tyr Asn Pro Ser Glu Asp Ile
            675             680             685

Leu Arg Ile Arg Asn His Ser Thr His Thr Lys Asn Gly Ser Pro Gln
        690             695             700

Lys Gly Tyr Glu Lys Phe Glu Phe Asn Ile Glu Asp Cys Arg Lys Phe
705             710             715             720

Ile Asp Phe Tyr Lys Gln Ser Ile Ser Lys His Pro Glu Trp Lys Asp
            725             730             735

Phe Gly Phe Arg Phe Ser Asp Thr Gln Arg Tyr Asn Ser Ile Asp Glu
            740             745             750

Phe Tyr Arg Glu Val Glu Asn Gln Gly Tyr Lys Leu Thr Phe Glu Asn
            755             760             765

Ile Ser Glu Ser Tyr Ile Asp Ser Val Val Asn Gln Gly Lys Leu Tyr
        770             775             780

Leu Phe Gln Ile Tyr Asn Lys Asp Phe Ser Ala Tyr Ser Lys Gly Arg
785             790             795             800

Pro Asn Leu His Thr Leu Tyr Trp Lys Ala Leu Phe Asp Glu Arg Asn
            805             810             815

Leu Gln Asp Val Val Tyr Lys Leu Asn Gly Glu Ala Glu Leu Phe Tyr
            820             825             830

Arg Lys Gln Ser Ile Pro Lys Lys Ile Thr His Pro Ala Lys Glu Ala
            835             840             845

Ile Ala Asn Lys Asn Lys Asp Asn Pro Lys Lys Glu Ser Val Phe Glu
        850             855             860

Tyr Asp Leu Ile Lys Asp Lys Arg Phe Thr Glu Asp Lys Phe Phe Phe
865             870             875             880

His Cys Pro Ile Thr Ile Asn Phe Lys Ser Ser Gly Ala Asn Lys Phe
            885             890             895

Asn Asp Glu Ile Asn Leu Leu Leu Lys Glu Lys Ala Asn Asp Val His
```

-continued

```
              900            905             910
Ile Leu Ser Ile Ala Arg Gly Glu Arg His Leu Ala Tyr Tyr Thr Leu
        915                 920              925

Val Asp Gly Lys Gly Asn Ile Ile Lys Gln Asp Thr Phe Asn Ile Ile
    930                 935              940

Gly Asn Asp Arg Met Lys Thr Asn Tyr His Asp Lys Leu Ala Ala Ile
945                 950              955                 960

Glu Lys Asp Arg Asp Ser Ala Arg Lys Asp Trp Lys Lys Ile Asn Asn
            965                 970                 975

Ile Lys Glu Met Lys Glu Gly Tyr Leu Ser Gln Val Val His Glu Ile
            980                 985              990

Ala Lys Leu Val Ile Glu Tyr Asn  Ala Ile Val Val Phe  Glu Asp Leu
            995                 1000               1005

Asn Phe  Gly Phe Lys Arg Gly  Arg Phe Lys Val Glu  Lys Gln Val
    1010                 1015              1020

Tyr Gln  Lys Leu Glu Lys Met  Leu Ile Glu Lys Leu  Asn Tyr Leu
    1025                 1030              1035

Val Phe  Lys Asp Asn Glu Phe  Asp Lys Thr Gly Gly  Val Leu Arg
    1040                 1045              1050

Ala Tyr  Gln Leu Thr Ala Pro  Phe Glu Thr Phe Lys  Lys Met Gly
    1055                 1060              1065

Lys Gln  Thr Gly Ile Ile Tyr  Tyr Val Pro Ala Gly  Phe Thr Ser
    1070                 1075              1080

Lys Ile  Cys Pro Val Thr Gly  Phe Val Asn Gln Leu  Tyr Pro Lys
    1085                 1090              1095

Tyr Glu  Ser Val Ser Lys Ser  Gln Glu Phe Phe Ser  Lys Phe Asp
    1100                 1105              1110

Lys Ile  Cys Tyr Asn Leu Asp  Lys Gly Tyr Phe Glu  Phe Ser Phe
    1115                 1120              1125

Asp Tyr  Lys Asn Phe Gly Asp  Lys Ala Ala Lys Gly  Lys Trp Thr
    1130                 1135              1140

Ile Ala  Ser Phe Gly Ser Arg  Leu Ile Asn Phe Arg  Asn Ser Asp
    1145                 1150              1155

Lys Asn  His Asn Trp Asp Thr  Arg Glu Val Tyr Pro  Thr Lys Glu
    1160                 1165              1170

Leu Glu  Lys Leu Leu Lys Asp  Tyr Ser Ile Glu Tyr  Gly His Gly
    1175                 1180              1185

Glu Cys  Ile Lys Ala Ala Ile  Cys Gly Glu Ser Asp  Lys Lys Phe
    1190                 1195              1200

Phe Ala  Lys Leu Thr Ser Val  Leu Asn Thr Ile Leu  Gln Met Arg
    1205                 1210              1215

Asn Ser  Lys Thr Gly Thr Glu  Leu Asp Tyr Leu Ile  Ser Pro Val
    1220                 1225              1230

Ala Asp  Val Asn Gly Asn Phe  Phe Asp Ser Arg Gln  Ala Pro Lys
    1235                 1240              1245

Asn Met  Pro Gln Asp Ala Asp  Ala Asn Gly Ala Tyr  His Ile Gly
    1250                 1255              1260

Leu Lys  Gly Leu Met Leu Leu  Gly Arg Ile Lys Asn  Asn Gln Glu
    1265                 1270              1275

Gly Lys  Lys Leu Asn Leu Val  Ile Lys Asn Glu Glu  Tyr Phe Glu
    1280                 1285              1290

Phe Val  Gln Asn Arg Asn Asn
    1295                 1300
```

```
<210> SEQ ID NO 6
<211> LENGTH: 1229
<212> TYPE: PRT
<213> ORGANISM: artificial
<220> FEATURE:
<223> OTHER INFORMATION: dead LbCpf1

<400> SEQUENCE: 6

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
                20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
                100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
        130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
                180                 185                 190

Val Asp Ala Ile Phe Asp Lys His Glu Val Gln Glu Ile Lys Glu Lys
            195                 200                 205

Ile Leu Asn Ser Asp Tyr Asp Val Glu Asp Phe Phe Glu Gly Glu Phe
        210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
                260                 265                 270

Phe Lys Pro Leu Tyr Lys Gln Val Leu Ser Asp Arg Glu Ser Leu Ser
            275                 280                 285

Phe Tyr Gly Glu Gly Tyr Thr Ser Asp Glu Glu Val Leu Glu Val Phe
        290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
            355                 360                 365
```

-continued

```
Ile His Leu Lys Lys Lys Ala Val Val Thr Glu Lys Tyr Glu Asp Asp
    370             375             380

Arg Arg Lys Ser Phe Lys Lys Ile Gly Ser Phe Ser Leu Glu Gln Leu
385             390             395             400

Gln Glu Tyr Ala Asp Ala Asp Leu Ser Val Val Glu Lys Leu Lys Glu
            405             410             415

Ile Ile Ile Gln Lys Val Asp Glu Ile Tyr Lys Val Tyr Gly Ser Ser
            420             425             430

Glu Lys Leu Phe Asp Ala Asp Phe Val Leu Glu Lys Ser Leu Lys Lys
        435             440             445

Asn Asp Ala Val Val Ala Ile Met Lys Asp Leu Leu Asp Ser Val Lys
    450             455             460

Ser Phe Glu Asn Tyr Ile Lys Ala Phe Phe Gly Glu Gly Lys Glu Thr
465             470             475             480

Asn Arg Asp Glu Ser Phe Tyr Gly Asp Phe Val Leu Ala Tyr Asp Ile
            485             490             495

Leu Leu Lys Val Asp His Ile Tyr Asp Ala Ile Arg Asn Tyr Val Thr
            500             505             510

Gln Lys Pro Tyr Ser Lys Asp Lys Phe Lys Leu Tyr Phe Gln Asn Pro
        515             520             525

Gln Phe Met Gly Gly Trp Asp Lys Asp Lys Glu Thr Asp Tyr Arg Ala
    530             535             540

Thr Ile Leu Arg Tyr Gly Ser Lys Tyr Tyr Leu Ala Ile Met Asp Lys
545             550             555             560

Lys Tyr Ala Lys Cys Leu Gln Lys Ile Asp Lys Asp Asp Val Asn Gly
            565             570             575

Asn Tyr Glu Lys Ile Asn Tyr Lys Leu Leu Pro Gly Pro Asn Lys Met
            580             585             590

Leu Pro Lys Val Phe Phe Ser Lys Lys Trp Met Ala Tyr Tyr Asn Pro
        595             600             605

Ser Glu Asp Ile Gln Lys Ile Tyr Lys Asn Gly Thr Phe Lys Lys Gly
    610             615             620

Asp Met Phe Asn Leu Asn Asp Cys His Lys Leu Ile Asp Phe Phe Lys
625             630             635             640

Asp Ser Ile Ser Arg Tyr Pro Lys Trp Ser Asn Ala Tyr Asp Phe Asn
            645             650             655

Phe Ser Glu Thr Glu Lys Tyr Lys Asp Ile Ala Gly Phe Tyr Arg Glu
            660             665             670

Val Glu Glu Gln Gly Tyr Lys Val Ser Phe Glu Ser Ala Ser Lys Lys
        675             680             685

Glu Val Asp Lys Leu Val Glu Glu Gly Lys Leu Tyr Met Phe Gln Ile
    690             695             700

Tyr Asn Lys Asp Phe Ser Asp Lys Ser His Gly Thr Pro Asn Leu His
705             710             715             720

Thr Met Tyr Phe Lys Leu Leu Phe Asp Glu Asn Asn His Gly Gln Ile
            725             730             735

Arg Leu Ser Gly Gly Ala Glu Leu Phe Met Arg Arg Ala Ser Leu Lys
            740             745             750

Lys Glu Glu Leu Val Val His Pro Ala Asn Ser Pro Ile Ala Asn Lys
        755             760             765

Asn Pro Asp Asn Pro Lys Lys Thr Thr Thr Leu Ser Tyr Asp Val Tyr
    770             775             780
```

-continued

```
Lys Asp Lys Arg Phe Ser Glu Asp Gln Tyr Glu Leu His Ile Pro Ile
785             790             795             800

Ala Ile Asn Lys Cys Pro Lys Asn Ile Phe Lys Ile Asn Thr Glu Val
            805             810             815

Arg Val Leu Leu Lys His Asp Asp Asn Pro Tyr Val Ile Gly Ile Ala
            820             825             830

Arg Gly Glu Arg Asn Leu Leu Tyr Ile Val Val Asp Gly Lys Gly
        835             840             845

Asn Ile Val Glu Gln Tyr Ser Leu Asn Glu Ile Ile Asn Asn Phe Asn
    850             855             860

Gly Ile Arg Ile Lys Thr Asp Tyr His Ser Leu Leu Asp Lys Lys Glu
865             870             875             880

Lys Glu Arg Phe Glu Ala Arg Gln Asn Trp Thr Ser Ile Glu Asn Ile
            885             890             895

Lys Glu Leu Lys Ala Gly Tyr Ile Ser Gln Val Val His Lys Ile Cys
        900             905             910

Glu Leu Val Glu Lys Tyr Asp Ala Val Ile Ala Leu Glu Asp Leu Asn
        915             920             925

Ser Gly Phe Lys Asn Ser Arg Val Lys Val Glu Lys Gln Val Tyr Gln
    930             935             940

Lys Phe Glu Lys Met Leu Ile Asp Lys Leu Asn Tyr Met Val Asp Lys
945             950             955             960

Lys Ser Asn Pro Cys Ala Thr Gly Gly Ala Leu Lys Gly Tyr Gln Ile
            965             970             975

Thr Asn Lys Phe Glu Ser Phe Lys Ser Met Ser Thr Gln Asn Gly Phe
        980             985             990

Ile Phe Tyr Ile Pro Ala Trp Leu  Thr Ser Lys Ile Asp  Pro Ser Thr
        995             1000            1005

Gly Phe  Val Asn Leu Leu Lys  Thr Lys Tyr Thr Ser  Ile Ala Asp
    1010            1015            1020

Ser Lys  Lys Phe Ile Ser Ser  Phe Asp Arg Ile Met  Tyr Val Pro
    1025            1030            1035

Glu Glu  Asp Leu Phe Glu Phe  Ala Leu Asp Tyr Lys  Asn Phe Ser
    1040            1045            1050

Arg Thr  Asp Ala Asp Tyr Ile  Lys Lys Trp Lys Leu  Tyr Ser Tyr
    1055            1060            1065

Gly Asn  Arg Ile Arg Ile Phe  Arg Asn Pro Lys Lys  Asn Asn Val
    1070            1075            1080

Phe Asp  Trp Glu Glu Val Cys  Leu Thr Ser Ala Tyr  Lys Glu Leu
    1085            1090            1095

Phe Asn  Lys Tyr Gly Ile Asn  Tyr Gln Gln Gly Asp  Ile Arg Ala
    1100            1105            1110

Leu Leu  Cys Glu Gln Ser Asp  Lys Ala Phe Tyr Ser  Ser Phe Met
    1115            1120            1125

Ala Leu  Met Ser Leu Met Leu  Gln Met Arg Asn Ser  Ile Thr Gly
    1130            1135            1140

Arg Thr  Asp Val Asp Phe Leu  Ile Ser Pro Val Lys  Asn Ser Asp
    1145            1150            1155

Gly Ile  Phe Tyr Asp Ser Arg  Asn Tyr Glu Ala Gln  Glu Asn Ala
    1160            1165            1170

Ile Leu  Pro Lys Asn Ala Asp  Ala Asn Gly Ala Tyr  Asn Ile Ala
    1175            1180            1185

Arg Lys  Val Leu Trp Ala Ile  Gly Gln Phe Lys Lys  Ala Glu Asp
```

-continued

```
      1190                1195                1200

Glu Lys  Leu Asp Lys Val Lys  Ile Ala Ile Ser Asn  Lys Glu Trp
      1205                1210                1215

Leu Glu  Tyr Ala Gln Thr Ser  Val Lys His Lys
      1220                1225

<210> SEQ ID NO 7
<211> LENGTH: 7
<212> TYPE: PRT
<213> ORGANISM: artificial
<220> FEATURE:
<223> OTHER INFORMATION: nuclear localization signal (NLS)

<400> SEQUENCE: 7

Pro Lys Lys Lys Arg Lys Val
1               5

<210> SEQ ID NO 8
<211> LENGTH: 20
<212> TYPE: PRT
<213> ORGANISM: artificial
<220> FEATURE:
<223> OTHER INFORMATION: Cell penetrating peptide sequence derived from
      the TAT protein of HIV-1

<400> SEQUENCE: 8

Gly Arg Lys Lys Arg Arg Gln Arg Arg Arg Pro Pro Gln Pro Lys Lys
1               5                   10                  15

Lys Arg Lys Val
          20

<210> SEQ ID NO 9
<211> LENGTH: 19
<212> TYPE: PRT
<213> ORGANISM: artificial
<220> FEATURE:
<223> OTHER INFORMATION: Peptide sequence derived from the TLM sequence
      of the human hepatitis B virus

<400> SEQUENCE: 9

Pro Leu Ser Ser Ile Phe Ser Arg Ile Gly Asp Pro Pro Lys Lys Lys
1               5                   10                  15

Arg Lys Val

<210> SEQ ID NO 10
<211> LENGTH: 362
<212> TYPE: PRT
<213> ORGANISM: Arabidopsis thaliana

<400> SEQUENCE: 10

Met Glu Gly Lys Phe Ala Ile Ser Glu Ser Thr Asn Leu Leu Gln Arg
1               5                   10                  15

Ile Lys Asp Phe Thr Gln Ser Val Val Val Asp Leu Ala Glu Gly Arg
            20                  25                  30

Ser Pro Lys Ile Ser Ile Asn Gln Phe Arg Asn Tyr Cys Met Asn Pro
        35                  40                  45

Glu Ala Asp Cys Leu Cys Ser Ser Asp Lys Pro Lys Gly Gln Glu Ile
    50                  55                  60

Phe Thr Leu Lys Lys Glu Pro Gln Thr Tyr Arg Ile Asp Met Leu Leu
65                  70                  75                  80

Arg Val Leu Leu Ile Val Gln Gln Leu Leu Gln Glu Asn Arg His Ala
                85                  90                  95
```

```
Ser Lys Arg Asp Ile Tyr Tyr Met His Pro Ser Ala Phe Lys Ala Gln
            100                 105                 110

Ser Ile Val Asp Arg Ala Ile Gly Asp Ile Cys Ile Leu Phe Gln Cys
            115                 120                 125

Ser Arg Tyr Asn Leu Asn Val Val Ser Val Gly Asn Gly Leu Val Met
            130                 135                 140

Gly Trp Leu Lys Phe Arg Glu Ala Gly Arg Lys Phe Asp Cys Leu Asn
145                 150                 155                 160

Ser Leu Asn Thr Ala Tyr Pro Val Pro Val Leu Val Glu Glu Val Glu
                165                 170                 175

Asp Ile Val Ser Leu Ala Glu Tyr Ile Leu Val Val Glu Lys Glu Thr
                180                 185                 190

Val Phe Gln Arg Leu Ala Asn Asp Met Phe Cys Lys Thr Asn Arg Cys
                195                 200                 205

Ile Val Ile Thr Gly Arg Gly Tyr Pro Asp Val Ser Thr Arg Arg Phe
            210                 215                 220

Leu Arg Leu Leu Met Glu Lys Leu His Leu Pro Val His Cys Leu Val
225                 230                 235                 240

Asp Cys Asp Pro Tyr Gly Phe Glu Ile Leu Ala Thr Tyr Arg Phe Gly
                245                 250                 255

Ser Met Gln Met Ala Tyr Asp Ile Glu Ser Leu Arg Ala Pro Asp Met
                260                 265                 270

Lys Trp Leu Gly Ala Phe Pro Ser Asp Ser Glu Val Tyr Ser Val Pro
            275                 280                 285

Lys Gln Cys Leu Leu Pro Leu Thr Glu Glu Asp Lys Lys Arg Thr Glu
            290                 295                 300

Ala Met Leu Leu Arg Cys Tyr Leu Lys Arg Glu Met Pro Gln Trp Arg
305                 310                 315                 320

Leu Glu Leu Glu Thr Met Leu Lys Arg Gly Val Lys Phe Glu Ile Glu
                325                 330                 335

Ala Leu Ser Val His Ser Leu Ser Phe Leu Ser Glu Val Tyr Ile Pro
                340                 345                 350

Ser Lys Ile Arg Arg Glu Val Ser Ser Pro
            355                 360
```

```
<210> SEQ ID NO 11
<211> LENGTH: 487
<212> TYPE: PRT
<213> ORGANISM: Oryza sativa japonica

<400> SEQUENCE: 11
```

```
Met Asp Asp Ser Thr Asp Asp Asp Ser Tyr His Pro Arg Lys His Tyr
1               5                   10                  15

Ala Tyr Asp Arg Gln Val Ser Ser Ser Arg Trp Arg Thr Ser Arg Glu
                20                  25                  30

Tyr Ile Arg Gly Pro Gly Pro Glu Thr His Thr Thr Glu Ser Ala Gln
            35                  40                  45

Asp Gly Gln Asp Pro Pro Ala Gly Val Tyr Ser Tyr Gly Tyr Phe Ser
        50                  55                  60

Gly Ser Gly Asn Asp Pro Gln Val Gln Gly His Phe Val Pro Glu Ile
65                  70                  75                  80

Gln Lys Tyr Asn Pro Tyr Val Ile Phe Lys Gly Glu Gln Leu Pro Val
                85                  90                  95

Pro Ile Trp Glu Leu Pro Glu Glu Lys Val Gln Asp Phe His Asp Arg
```

-continued

```
                 100                 105                 110

Tyr Phe Ile Ala Lys Asp Lys Ser Arg Val Glu Ala Arg Lys Thr Leu
            115                 120                 125

Asn Arg Leu Leu Glu Gly Asn Ile Asn Thr Ile Glu Arg Gly His Gly
    130                 135                 140

Tyr Lys Phe Asn Ile Pro Lys Tyr Thr Asp Asn Met Glu Phe Asn Glu
145                 150                 155                 160

Glu Val Lys Val Ser Leu Ala Lys Ala Gly Lys Thr Ile Ser Arg Ser
                165                 170                 175

Phe Cys Asn Ala Asn Gln Arg Glu Val Ala Ser Arg Thr Gly Tyr Thr
            180                 185                 190

Ile Asp Leu Ile Glu Arg Thr Leu Gly Ala Gly Leu Asn Ile Ser Lys
            195                 200                 205

Arg Thr Val Leu Tyr Thr Asn Lys Asp Leu Phe Gly Asp Gln Ser Lys
    210                 215                 220

Ser Asp Gln Ala Ile Asn Asp Ile Cys Ala Leu Thr Asn Ile Arg Arg
225                 230                 235                 240

Gly Ser Leu Gly Ile Ile Ala Ala Glu Lys Gly Ile Val Val Gly Asn
            245                 250                 255

Ile Phe Leu Glu Leu Thr Asn Gly Lys Ser Ile Ser Cys Ser Ile Gly
            260                 265                 270

Val Gln Ile Pro His Arg Leu Asp Gln Ile Lys Asp Val Cys Val Glu
            275                 280                 285

Ile Gly Ser Arg Asn Ile Glu Tyr Ile Leu Val Val Glu Lys His Thr
    290                 295                 300

Met Leu Asn Tyr Leu Leu Glu Met Asp Tyr His Thr Asn Asn Asn Cys
305                 310                 315                 320

Ile Ile Leu Thr Gly Cys Gly Met Pro Thr Leu Gln Thr Arg Asp Phe
            325                 330                 335

Leu Arg Phe Leu Lys Gln Arg Thr Gly Leu Pro Val Phe Gly Leu Cys
            340                 345                 350

Asp Pro Asp Pro Glu Gly Ile Ser Ile Leu Ala Thr Tyr Ala Arg Gly
            355                 360                 365

Ser Cys Asn Ser Ala Tyr Asp Asn Phe Asn Ile Ser Val Pro Ser Ile
    370                 375                 380

Cys Trp Val Gly Leu Ser Ser Ser Asp Met Ile Lys Leu Asn Leu Ser
385                 390                 395                 400

Glu Thr Asn Tyr Ser Arg Leu Ser Arg Glu Asp Lys Thr Met Leu Lys
                405                 410                 415

Asn Leu Trp Gln Asp Asp Leu Ser Asp Val Trp Lys Arg Arg Ile Glu
            420                 425                 430

Glu Met Ile Ser Phe Asp Lys Lys Ala Ser Phe Glu Ala Ile His Ser
            435                 440                 445

Leu Gly Phe Asp Tyr Phe Ala Thr Asn Leu Leu Pro Asp Met Ile Asn
    450                 455                 460

Lys Val Arg Glu Gly Tyr Val Gln Val Gln Glu Lys Lys Glu Pro Gln
465                 470                 475                 480

Asp Thr Glu Ala Ser Glu Asp
                485
```

<210> SEQ ID NO 12
<211> LENGTH: 381
<212> TYPE: PRT
<213> ORGANISM: Oryza sativa japonica

<400> SEQUENCE: 12

```
Met Ala Gly Arg Glu Lys Arg Arg Arg Val Ala Ala Leu Asp Gly Glu
1               5                   10                  15

Glu Arg Arg Arg Arg Gln Glu Glu Ala Ala Thr Leu Leu His Arg Ile
            20                  25                  30

Arg Gly Leu Val Arg Trp Val Val Ala Glu Val Ala Ala Gly Arg Ser
        35                  40                  45

Pro Thr Val Ala Leu His Arg Tyr Gln Asn Tyr Cys Ser Ser Ala Ser
    50                  55                  60

Ala Ala Ala Ala Ser Pro Cys Ala Cys Ser Tyr Asp Val Pro Val Gly
65                  70                  75                  80

Thr Asp Val Leu Ser Leu Leu His Arg Gly Ser His Ala Ser Arg Leu
                85                  90                  95

Asn Val Leu Leu Arg Val Leu Leu Val Val Gln Gln Leu Leu Gln Gln
            100                 105                 110

Asn Lys His Cys Ser Lys Arg Asp Ile Tyr Tyr Met Tyr Pro Ser Ile
            115                 120                 125

Phe Gln Glu Gln Ala Val Val Asp Arg Ala Ile Asn Asp Ile Cys Val
    130                 135                 140

Leu Phe Lys Cys Ser Arg His Asn Leu Asn Val Val Pro Val Ala Lys
145                 150                 155                 160

Gly Leu Val Met Gly Trp Ile Arg Phe Leu Glu Gly Glu Lys Glu Val
                165                 170                 175

Tyr Cys Val Thr Asn Val Asn Ala Ala Phe Ser Ile Pro Val Ser Ile
            180                 185                 190

Glu Ala Ile Lys Asp Val Val Ser Val Ala Asp Tyr Ile Leu Ile Val
            195                 200                 205

Glu Lys Glu Thr Val Phe Gln Arg Leu Ala Asn Asp Lys Phe Cys Glu
    210                 215                 220

Arg Asn Arg Cys Ile Val Ile Thr Gly Arg Gly Tyr Pro Asp Ile Pro
225                 230                 235                 240

Thr Arg Arg Phe Leu Arg Tyr Leu Val Glu Gln Leu His Leu Pro Val
            245                 250                 255

Tyr Cys Leu Val Asp Ala Asp Pro Tyr Gly Phe Asp Ile Leu Ala Thr
            260                 265                 270

Tyr Lys Phe Gly Ser Leu Gln Leu Ala Tyr Asp Ala Asn Phe Leu Arg
            275                 280                 285

Val Pro Asp Ile Arg Trp Leu Gly Val Phe Thr Ser Asp Phe Glu Asp
    290                 295                 300

Tyr Arg Leu Pro Asp Cys Cys Leu Leu His Leu Ser Ser Glu Asp Arg
305                 310                 315                 320

Arg Lys Ala Glu Gly Ile Leu Ser Arg Cys Tyr Leu His Arg Glu Ala
            325                 330                 335

Pro Gln Trp Arg Leu Glu Leu Glu Ala Met Leu Gln Lys Gly Val Lys
            340                 345                 350

Phe Glu Ile Glu Ala Leu Ser Ala Cys Ser Ile Ser Phe Leu Ser Glu
            355                 360                 365

Glu Tyr Ile Pro Lys Lys Ile Lys Gln Gly Arg His Ile
    370                 375                 380
```

<210> SEQ ID NO 13
<211> LENGTH: 381
<212> TYPE: PRT

<213> ORGANISM: Oryza sativa indica

<400> SEQUENCE: 13

```
Met Ala Gly Arg Glu Lys Arg Arg Arg Val Ala Ala Leu Asp Gly Glu
1               5                   10                  15

Glu Arg Arg Arg Arg Gln Glu Glu Ala Ala Thr Leu Leu His Arg Ile
            20                  25                  30

Arg Gly Leu Val Arg Trp Val Val Ala Glu Val Ala Ala Gly Arg Ser
        35                  40                  45

Pro Thr Val Ala Leu His Arg Tyr Gln Asn Tyr Cys Ser Ser Ala Ser
    50                  55                  60

Ala Ala Ala Ala Ser Pro Cys Ala Cys Ser Tyr Asp Val Pro Val Gly
65                  70                  75                  80

Thr Asp Val Leu Ser Leu Leu His Arg Gly Ser His Ala Ser Arg Leu
                85                  90                  95

Asn Val Leu Leu Arg Val Leu Leu Val Gln Gln Leu Leu Gln Gln
            100                 105                 110

Asn Lys His Cys Ser Lys Arg Asp Ile Tyr Tyr Met Tyr Pro Ser Ile
        115                 120                 125

Phe Gln Glu Gln Ala Val Val Asp Arg Ala Ile Asn Asp Ile Cys Val
    130                 135                 140

Leu Phe Lys Cys Ser Arg His Asn Leu Asn Val Val Pro Val Ala Lys
145                 150                 155                 160

Gly Leu Val Met Gly Trp Ile Arg Phe Leu Glu Gly Glu Lys Glu Val
                165                 170                 175

Tyr Cys Val Thr Asn Val Asn Ala Ala Phe Ser Ile Pro Val Ser Ile
            180                 185                 190

Glu Ala Ile Lys Asp Val Val Ser Val Ala Asp Tyr Ile Leu Ile Val
        195                 200                 205

Glu Lys Glu Thr Val Phe Gln Arg Leu Ala Asn Asp Lys Phe Cys Glu
    210                 215                 220

Arg Asn Arg Cys Ile Val Ile Thr Gly Arg Gly Tyr Pro Asp Ile Pro
225                 230                 235                 240

Thr Arg Arg Phe Leu Arg Tyr Leu Val Glu Gln Leu His Leu Pro Val
                245                 250                 255

Tyr Cys Leu Val Asp Ala Asp Pro Tyr Gly Phe Asp Ile Leu Ala Thr
            260                 265                 270

Tyr Lys Phe Gly Ser Leu Gln Leu Ala Tyr Asp Ala Asn Phe Leu Arg
        275                 280                 285

Val Pro Asp Ile Arg Trp Leu Gly Val Phe Thr Ser Asp Phe Glu Asp
    290                 295                 300

Tyr Arg Leu Pro Asp Cys Cys Leu Leu His Leu Ser Ser Glu Asp Arg
305                 310                 315                 320

Arg Lys Ala Glu Gly Ile Leu Ser Arg Cys Tyr Leu His Arg Glu Ala
                325                 330                 335

Pro Gln Trp Arg Leu Glu Leu Glu Ala Met Leu Gln Lys Gly Val Lys
                340                 345                 350

Phe Glu Ile Glu Ala Leu Ser Ala Cys Ser Ile Ser Phe Leu Ser Glu
        355                 360                 365

Glu Tyr Ile Pro Lys Lys Ile Lys Gln Gly Arg His Ile
    370                 375                 380
```

<210> SEQ ID NO 14
<211> LENGTH: 442

<212> TYPE: PRT
<213> ORGANISM: Brassica campestris

<400> SEQUENCE: 14

```
Met Ser Glu Lys Lys Arg Arg Gly Gly Ala Gly Ala Gly Ala Ala Ser
1               5                   10                  15

Gly Ser Ala Ser Lys Lys Pro Arg Val Ser Thr Ala Ala Ser Tyr Ala
            20                  25                  30

Glu Ser Leu Arg Ser Lys Leu Arg Pro Asp Ala Ser Ile Leu Ala Thr
        35                  40                  45

Leu Arg Ser Leu Ala Ser Ala Cys Ser Lys Ser Lys Pro Ala Gly Ser
    50                  55                  60

Ser Ser Ser Ser Ser Ser Ala Ser Lys Ala Leu Ala Ala Glu Asp Asp
65                  70                  75                  80

Pro Ala Ala Ser Tyr Ile Val Val Ala Asp Gln Asp Ser Ala Ser Val
                85                  90                  95

Thr Ser Arg Ile Asn Arg Leu Val Leu Ala Ala Ala Arg Ser Ile Leu
            100                 105                 110

Ser Gly Arg Gly Phe Ser Phe Ala Val Pro Ser Arg Ala Ala Ser Asn
        115                 120                 125

Gln Val Tyr Leu Pro Asp Leu Asp Arg Ile Val Leu Val Arg Arg Glu
    130                 135                 140

Ser Ala Arg Pro Phe Ala Asn Val Ala Thr Ala Arg Lys Ala Thr Ile
145                 150                 155                 160

Thr Ala Arg Val Leu Ser Leu Val His Ala Val Leu Arg Arg Gly Ile
                165                 170                 175

His Val Thr Lys Arg Asp Leu Phe Tyr Thr Asp Val Lys Leu Phe Gly
            180                 185                 190

Asp Gln Ala Gln Ser Asp Ala Val Leu Asp Asp Val Ser Cys Met Leu
        195                 200                 205

Gly Cys Thr Arg Ser Ser Leu His Val Val Ala Ser Glu Lys Gly Val
    210                 215                 220

Val Val Gly Arg Leu Thr Phe Ala Asp Asp Gly Asp Arg Ile Asp Cys
225                 230                 235                 240

Thr Arg Met Gly Val Gly Gly Lys Ala Ile Pro Pro Asn Ile Asp Arg
                245                 250                 255

Val Ser Gly Ile Glu Ser Asp Ala Leu Phe Ile Leu Leu Val Glu Lys
            260                 265                 270

Asp Ala Ala Phe Met Arg Leu Ala Glu Asp Arg Phe Tyr Asn Arg Phe
        275                 280                 285

Pro Cys Ile Ile Leu Thr Ala Lys Gly Gln Pro Asp Val Ala Thr Arg
    290                 295                 300

Leu Phe Leu Arg Arg Leu Lys Val Glu Leu Lys Leu Pro Val Leu Ala
305                 310                 315                 320

Leu Val Asp Ser Asp Pro Tyr Gly Leu Lys Ile Leu Ser Val Tyr Met
                325                 330                 335

Cys Gly Ser Lys Asn Met Ser Tyr Asp Ser Ala Asn Leu Thr Thr Pro
            340                 345                 350

Asp Ile Lys Trp Leu Gly Val Arg Pro Ser Asp Leu Asp Lys Tyr Arg
        355                 360                 365

Val Pro Glu Gln Cys Arg Leu Pro Met Thr Asp His Asp Ile Lys Val
    370                 375                 380

Gly Lys Glu Leu Leu Glu Glu Asp Phe Val Lys Gln Asn Glu Gly Trp
385                 390                 395                 400
```

-continued

```
Val Lys Glu Leu Glu Thr Met Leu Arg Thr Arg Gln Lys Ala Glu Ile
            405                 410                 415

Gln Ala Leu Ser Ser Phe Gly Phe Gln Tyr Leu Thr Glu Val Tyr Leu
            420                 425                 430

Pro Leu Lys Leu Gln Gln Gln Asp Trp Ile
        435                 440

<210> SEQ ID NO 15
<211> LENGTH: 362
<212> TYPE: PRT
<213> ORGANISM: Brassica campestris

<400> SEQUENCE: 15

Met Glu Gly Asn Phe Gln Ile Ser Glu Thr Thr Asn Leu Leu Arg Lys
1               5                   10                  15

Ile Lys Glu Phe Thr Arg Ser Ile Val Glu Asp Leu Ala Glu Gly Lys
            20                  25                  30

Ser Pro Glu Ile Ser Ile Asn Arg Phe Arg Asn Tyr Cys Asn Asp Pro
        35                  40                  45

Glu Ala Asp Cys Phe Cys Ser Ser Asp Glu Pro Lys Gly Arg Glu Ile
        50                  55                  60

Leu Thr Leu Arg Lys Arg Ser Gln Thr Tyr Arg Ile Asp Met Leu Leu
65                  70                  75                  80

Arg Val Leu Leu Ile Val Gln Gln Leu Leu Gln Glu Asn Arg His Gly
                85                  90                  95

Ser Lys Arg Asp Ile Tyr Tyr Met His Pro Ser Ala Phe Lys Ala Gln
            100                 105                 110

Ser Val Val Asp Arg Ala Ile Ala Asp Ile Cys Ile Leu Phe Gln Cys
            115                 120                 125

Ser Arg Tyr Asn Leu Asn Val Val Ser Val Gly Asn Gly Leu Val Met
        130                 135                 140

Gly Trp Leu Lys Phe Arg Glu Ala Gly Arg Lys Phe Asp Cys Leu Ser
145                 150                 155                 160

Ser Leu Asn Thr Ala Phe Pro Val Pro Val Leu Val Glu Glu Val Glu
                165                 170                 175

Asp Ile Val Ser Leu Ala Glu Tyr Ile Leu Val Val Glu Lys Glu Thr
            180                 185                 190

Val Phe Gln Arg Leu Ala Asn Asp Met Phe Cys Lys Thr Asn Arg Cys
            195                 200                 205

Ile Val Val Thr Gly Arg Gly Tyr Pro Asp Val Ser Thr Arg Arg Phe
        210                 215                 220

Leu Arg Leu Leu Met Glu Lys Leu Gln Leu Pro Val His Cys Leu Val
225                 230                 235                 240

Asp Cys Asp Pro Tyr Gly Phe Glu Ile Leu Ala Thr Tyr Arg Phe Gly
                245                 250                 255

Ser Met Gln Met Ala Tyr Asp Ile Glu Ser Leu Arg Ala Pro Glu Met
            260                 265                 270

Lys Trp Leu Gly Ala Phe Pro Ser Asp Ser Asp Ile Tyr Gly Val Pro
            275                 280                 285

His Gln Cys Leu Leu Pro Leu Thr Glu Glu Asp Lys Lys Arg Thr Glu
        290                 295                 300

Ala Met Leu Leu Arg Cys Tyr Leu Lys Arg Glu Met Pro Gln Trp Arg
305                 310                 315                 320

Leu Glu Leu Glu Thr Met Leu Lys Arg Gly Val Lys Phe Glu Ile Glu
```

-continued

```
                   325              330              335

Ala Leu Ser Val His Ser Leu Ser Phe Leu Ser Glu Val Tyr Ile Pro
            340              345              350

Ser Lys Ile Arg Ser Glu Gly Ser Phe His
        355              360

<210> SEQ ID NO 16
<211> LENGTH: 380
<212> TYPE: PRT
<213> ORGANISM: Brassica campestris

<400> SEQUENCE: 16

Met Glu Glu Asp Ala Ser Met Lys Phe Phe Ser Asp Gln Asn Thr Ser
1               5                  10                  15

Tyr Ala Asp Ile Leu Pro Pro Arg Glu Val Arg Ala Arg Ile Glu Val
            20                  25                  30

Ser Val Leu Asn Leu Leu Arg Val Leu Asn Ser Pro Asp Pro Ala Ile
        35                  40                  45

Ser Asp Leu Ser Leu Ile Asn Arg Lys Arg Ser Asn Ser Cys Ile Asn
    50                  55                  60

Gln Gly Ile Leu Thr Asp Val Ser Tyr Ile Phe Leu Ser Thr Ser Phe
65                  70                  75                  80

Thr Lys Ser Ser Leu Thr Asn Ala Lys Thr Ala Lys Ala Phe Val Arg
            85                  90                  95

Val Trp Lys Val Met Glu Met Cys Phe Gln Ile Leu Leu Gln Glu Lys
            100                 105                 110

Arg Val Thr Gln Arg Glu Leu Phe Tyr Lys Leu Leu Cys Asp Ser Pro
            115                 120                 125

Asp Leu Phe Ser Ser Gln Ile Glu Val Asn Arg Ser Val Gln Asp Val
    130                 135                 140

Val Ala Leu Leu Arg Cys Ser Arg Phe Ser Leu Gly Ile Met Ala Ser
145                 150                 155                 160

Thr Arg Gly Leu Val Ala Gly Arg Leu Tyr Leu Gln Glu Pro Gly Lys
            165                 170                 175

Glu Pro Val Asp Cys Ser Ala Cys Gly Ala Ser Gly Phe Pro Ile Ser
            180                 185                 190

Gly Asp Leu Asn Leu Leu Asp Asn Thr Val Met Thr Ser Asp Ala Arg
            195                 200                 205

Tyr Ile Ile Leu Val Glu Lys His Ala Ile Phe His Arg Leu Val Glu
    210                 215                 220

Asp Arg Val Phe Asn His Ile Pro Cys Val Phe Ile Thr Ala Lys Gly
225                 230                 235                 240

Tyr Pro Asp Ile Ala Thr Arg Phe Phe Leu His Arg Met Ser Ile Thr
            245                 250                 255

Phe Pro His Leu Pro Ile Leu Ala Leu Val Asp Trp Asn Pro Ala Gly
            260                 265                 270

Leu Ala Ile Leu Cys Thr Phe Lys Phe Gly Ser Ile Gly Met Gly Leu
            275                 280                 285

Glu Ala Tyr Arg Tyr Ala Cys Asn Val Lys Trp Ile Gly Leu Arg Gly
    290                 295                 300

Asp Asp Leu Asn Leu Ile Pro Glu Glu Ser Leu Val Pro Leu Lys Ala
305                 310                 315                 320

Lys Asp Ser Gln Ile Ala Lys Ser Leu Leu Ser Ser Lys Ile Leu Gln
            325                 330                 335
```

```
Glu Asn Tyr Arg Glu Glu Leu Ser Leu Met Ile Glu Thr Gly Lys Arg
            340                 345                 350

Ala Glu Ile Glu Ala Leu Tyr Cys His Gly Tyr Ser Tyr Leu Gly Lys
        355                 360                 365

Tyr Ile Ala Thr Lys Ile Val Gln Gly Lys Tyr Ile
    370                 375                 380

<210> SEQ ID NO 17
<211> LENGTH: 382
<212> TYPE: PRT
<213> ORGANISM: Zea mays

<400> SEQUENCE: 17

Met Ala Glu Ala Asn Val Ala Ala Ala Ser Leu Phe Gly Ala Asp Gly
1               5                   10                  15

Arg Leu Cys Ser Ala Asp Ile Leu Ala Pro Pro Glu Val Arg Ala Arg
            20                  25                  30

Ile Glu Val Ala Val Leu Asn Phe Leu Ala Ala Leu Ala Ser Pro Ser
        35                  40                  45

Ser Pro Ala Ile Ser Val Leu Pro Leu Ile Ser Arg Ser Ser Ala Asn
    50                  55                  60

Cys Ser Leu Arg Ser Gly Leu Leu Asn Asp Val Ser Ser Val Tyr Leu
65                  70                  75                  80

Ser Tyr Thr Phe Cys Lys Arg Ser Leu Thr His Asn Pro Lys Ala Phe
                85                  90                  95

Val Arg Val Trp Lys Val Met Glu Met Cys Tyr Lys Ile Leu Gly Glu
            100                 105                 110

Gly Lys Leu Val Gln Gln Arg Glu Leu Phe Tyr Lys Leu Leu Ser Asp
        115                 120                 125

Ser Pro Lys Tyr Phe Ser Cys Gln Arg His Val Asn Gln Ala Ile Gln
    130                 135                 140

Asp Val Val Ser Leu Leu Arg Cys Thr Arg Gln Ser Leu Gly Val Met
145                 150                 155                 160

Ala Ser Ser Arg Gly Ala Leu Ile Gly Arg Leu Val Leu His Glu Pro
                165                 170                 175

Asp Gly Glu Gln Ile Asp Cys Ser Ile Leu Gly Ala Ser Gly His Ala
            180                 185                 190

Ile Thr Gly Asp Leu Asn Leu Leu Ser Lys Leu Asn Leu Ser Ser Gly
        195                 200                 205

Ser Arg Tyr Ile Ile Val Val Glu Lys Asp Ala Val Phe Gln Arg Leu
    210                 215                 220

Ala Glu Asp Arg Leu Tyr Asn Gln Leu Pro Cys Ile Leu Ile Thr Ala
225                 230                 235                 240

Lys Gly Tyr Pro Asp Ile Ala Thr Arg Phe Ile Leu His Arg Leu Ser
                245                 250                 255

Gln Thr Phe Pro Asn Met Pro Ile Phe Ala Leu Val Asp Trp Asn Pro
            260                 265                 270

Ala Gly Leu Ala Ile Leu Cys Thr Tyr Lys Tyr Gly Ser Ile Ser Met
        275                 280                 285

Gly Leu Glu Ser Tyr Arg Tyr Ala Cys Asn Val Lys Trp Leu Gly Val
    290                 295                 300

Arg Gly Gly Asp Leu His Leu Ile Pro Glu Asp Ala Phe Gln Glu Leu
305                 310                 315                 320

Lys Pro Arg Asp Leu Gln Ile Ala Lys Ser Leu Met Ser Ser Lys Phe
                325                 330                 335
```

```
Leu Gln Glu Ser His Arg Ala Glu Leu Ala Leu Met Val Glu Arg Gly
        340                 345                 350

Lys Arg Ala Asp Ile Glu Ala Leu Tyr Ser His Gly Phe Asp Phe Leu
        355                 360                 365

Gly Lys Tyr Ile Ala Arg Lys Ile Val Gln Gly Asp Tyr Ile
        370                 375                 380

<210> SEQ ID NO 18
<211> LENGTH: 383
<212> TYPE: PRT
<213> ORGANISM: Zea mays

<400> SEQUENCE: 18

Met Ala Gly Arg Asp Lys Arg Arg Ala Ala Pro Leu Glu Gly Asp
1               5                   10                  15

Glu Gln Gln Leu Arg Arg Arg Leu Glu Glu Ala Ala Leu Leu Leu Arg
                20                  25                  30

Arg Ile Lys Gly Leu Val Arg Trp Ile Val Glu Glu Val Ala Ala Gly
        35                  40                  45

Arg Ser Pro Ser Ile Val Leu His Arg Tyr Arg Asn Tyr Cys Ser Ser
        50                  55                  60

Ala Asp Ser Ala Ser Pro Ser Pro Cys Ala Cys Ser Tyr Asp Ile Pro
65                  70                  75                  80

Val Gly Thr Asp Val Leu Ser Leu Leu His Lys Asp Tyr His Thr Ser
                85                  90                  95

Arg Leu Asn Val Leu Leu Arg Val Leu Phe Val Val Gln His Leu Leu
                100                 105                 110

Gln Gln Asn Lys His Cys Ser Lys Arg Asp Ile Tyr Tyr Met Tyr Pro
        115                 120                 125

Ser Ile Phe Val Glu Val Ala Val Val Asp Arg Ala Ile Asn Asp Ile
        130                 135                 140

Cys Ile Leu Phe Lys Cys Ser Arg His Asn Leu Asn Val Val Pro Val
145                 150                 155                 160

Val Lys Gly Leu Val Met Gly Trp Ile Arg Phe Met Glu Gly Glu Lys
                165                 170                 175

Lys Val Tyr Cys Ile Thr Ser Val Asn Ala Ala Phe Ser Ile Pro Val
                180                 185                 190

Asp Ile Glu Ala Ile Lys Asp Val Val Ser Val Ala His Tyr Ile Leu
        195                 200                 205

Val Val Glu Lys Glu Thr Val Phe Gln Arg Leu Ala Asn Asp Lys Phe
        210                 215                 220

Cys Glu Arg Asn Arg Cys Ile Val Ile Thr Gly Arg Gly Tyr Pro Asp
225                 230                 235                 240

Ile Pro Thr Arg Arg Phe Leu Arg Tyr Leu Val Glu Leu Leu His Leu
                245                 250                 255

Pro Ala Tyr Cys Leu Val Asp Ser Asp Pro Tyr Gly Phe Asp Ile Leu
                260                 265                 270

Ala Thr Tyr Lys Phe Gly Ser Leu Gln Leu Ala His Asp Ala Asn Leu
        275                 280                 285

Leu Arg Val Pro Asp Ile Arg Trp Leu Gly Val Phe Thr Ser Asp Phe
        290                 295                 300

Glu Glu Tyr Cys Leu Pro Asp Cys Cys Leu Leu Arg Leu Ser Pro Glu
305                 310                 315                 320

Asp Arg Arg Lys Ala Glu Gly Ile Leu Ala Arg Cys Tyr Leu His Arg
```

```
                    325                 330                 335
Glu Ala Pro Glu Trp Arg Ser Glu Leu Glu Ala Met Leu Gln Lys Gly
                340                 345                 350

Val Lys Phe Glu Ile Glu Ala Leu Ser Ala Asn Ser Ile Ser Phe Leu
                355                 360                 365

Ser His Glu Tyr Ile Pro Gln Lys Ile Lys Gln Gly Met His Leu
        370                 375                 380
```

<210> SEQ ID NO 19
<211> LENGTH: 218
<212> TYPE: PRT
<213> ORGANISM: Capsicum baccatum

<400> SEQUENCE: 19

```
Met Gly Trp Leu Arg Tyr Ala Glu Ser Gly Arg Lys Ile Asp Cys Ile
1               5                   10                  15

Ser Asn Pro Asn Thr Ala Tyr Pro Ile Pro Val His Val Glu Glu Val
                20                  25                  30

Asn Asp Ile Leu Ser Val Ala Gln Tyr Val Leu Val Val Glu Lys Glu
            35                  40                  45

Ser Val Phe Gln Arg Leu Ala Asn Asp Gln Phe Cys Lys Arg Asn Arg
        50                  55                  60

Cys Val Val Ile Thr Gly Arg Gly Tyr Pro Asp Val Pro Thr Arg Arg
65                  70                  75                  80

Phe Leu Arg Leu Leu Ile Asp Lys Leu His Leu Pro Val Tyr Cys Leu
                85                  90                  95

Val Asp Cys Asp Pro Tyr Gly Phe Asp Ile Leu Thr Thr Tyr Lys Phe
                100                 105                 110

Gly Ser Leu Gln Met Ala Tyr Asp Ala Thr Phe Leu Gln Val Ser Glu
            115                 120                 125

Ile Gln Trp Leu Gly Val Phe Val Gln Asp Ser Asp Asn Tyr Ser Ile
        130                 135                 140

Pro Gln Gln Cys Leu Leu Pro Leu Thr Val Glu Asp Lys Arg Lys Val
145                 150                 155                 160

Lys Ala Met Leu His Arg Cys Tyr Leu Gln Arg Glu Val Pro Lys Trp
                165                 170                 175

Arg Phe Glu Leu Glu Leu Leu Leu Tyr Lys Gly Val Lys Phe Glu Ile
            180                 185                 190

Glu Ala Leu Ser Val His Ser Leu Thr Phe Leu Ser His Glu Tyr Leu
            195                 200                 205

Pro Ser Lys Ile Asn Asn Gly Gly Tyr Ile
        210                 215
```

<210> SEQ ID NO 20
<211> LENGTH: 209
<212> TYPE: PRT
<213> ORGANISM: Capsicum baccatum

<400> SEQUENCE: 20

```
Met Arg Asn Ala Ser Glu Gly Gln Glu Gly Phe Thr Arg Ser Ile Val
1               5                   10                  15

Glu Asp Leu Ala Arg Gly Asn Ala Pro Leu Ile Tyr Ile Asp Arg Phe
                20                  25                  30

Arg Asn Tyr Cys Thr Gly Thr Ser Gly Asn Cys Ser Cys Ser Ser Gly
            35                  40                  45

Leu Pro Thr Gly Lys Glu Ala Ile Ser Leu Lys Arg Glu Cys His Val
```

-continued

```
       50                  55                  60

Arg Arg Leu Asp Ile Leu Leu Arg Val Leu Leu Ile Val Gln Gln Leu
65                  70                  75                  80

Leu Gln Glu Asn Arg His Gly Ser Lys Arg Asp Ile Tyr Tyr Met His
                85                  90                  95

Pro Thr Val Phe Lys Glu Gln Ser Val Val Asp Arg Ala Ile Asn Asp
               100                 105                 110

Ile Cys Ile Leu Leu Gln Cys Ser Arg His Asn Leu Asn Val Leu His
               115                 120                 125

Val Leu Phe Thr Val Lys Asp Ser Lys Ile Leu His Ile His Ala Phe
       130                 135                 140

Asp Met Gly Asn Gly Ser Ser Gln Val Ser Glu Arg Pro Arg Glu Pro
145                 150                 155                 160

His Lys Phe Leu Ala Leu Gly Gly Glu Phe Cys Leu Ile Phe Leu Leu
               165                 170                 175

His Asp Leu Ser Phe Ser Ile Ala Trp Gly Val Arg Cys Leu Leu Glu
               180                 185                 190

Met Gly Ala Tyr Leu Tyr Thr Val His Ile Ser Leu Gln Glu Cys Ala
               195                 200                 205

Ser
```

```
<210> SEQ ID NO 21
<211> LENGTH: 382
<212> TYPE: PRT
<213> ORGANISM: Carica papaya

<400> SEQUENCE: 21

Met Glu Asp Leu Gly Arg Ser Ser Met Arg Phe Phe Ser Asp Gln Arg
1                   5                  10                  15

Ile Cys Tyr Ala Asp Ile Leu Pro Pro Asn Glu Ala Arg Ala Arg Ile
                20                  25                  30

Glu Val Ala Val Leu Asn Phe Leu Arg Ile Leu Asn Ser Arg Asp Pro
        35                  40                  45

Ala Ile Ser Ser Leu Pro Leu Val Asn Arg Lys Trp Ser Asn Ser Arg
        50                  55                  60

Val Ser Lys Gly Leu Leu Thr Asp Val Ser Arg Ile Phe Leu Cys Arg
65                  70                  75                  80

Ser Phe Cys Ile Arg Ser Leu Met Arg Val Lys Ala Thr Lys Ala Phe
                85                  90                  95

Val Arg Val Trp Lys Val Met Glu Met Cys Phe Arg Ile Leu Ile Gln
               100                 105                 110

Glu Lys Arg Val Thr Gln Arg Glu Leu Phe Tyr Leu Leu Ile Cys Asp
               115                 120                 125

Ser Pro Glu Tyr Phe Ser Ser Gln Leu Glu Val Asn Arg Thr Ile Gln
       130                 135                 140

Asp Val Val Ala Leu Leu Gln Cys Ser Arg Tyr Ser Leu Gly Ile Met
145                 150                 155                 160

Ala Ser Ser Arg Gly Ile Val Ala Gly Arg Leu Leu Leu Gln Glu Pro
               165                 170                 175

Asn Gln Glu Val Val Asp Cys Ser Ala Cys Gly Ser Ser Gly Tyr Thr
               180                 185                 190

Ile Ser Gly Asp Leu Asn Leu Ile Gln Thr Leu Ile Leu Lys Thr Asp
               195                 200                 205

Ala Arg Tyr Ile Ile Val Val Glu Lys His Ala Ile Phe Gln Arg Leu
```

-continued

```
            210              215              220
Leu Glu Asp Gly Ile Ser Asn His Ile Pro Ser Ile Ile Ile Thr Ala
225                 230              235                 240

Lys Gly Tyr Pro Asp Ile Ala Thr Arg Phe Leu Leu His Arg Met Ser
                245              250              255

Ser Lys Phe Pro Gly Met Pro Ile Leu Ala Leu Val Asp Trp Asn Pro
                260              265              270

Ala Gly Leu Ala Ile Leu Cys Thr Phe Lys Tyr Gly Ser Ile Gly Met
                275              280              285

Gly Leu Glu Ala Tyr Arg Tyr Ala Cys Asn Val Lys Trp Val Gly Leu
                290              295              300

Arg Arg Asp Asp Leu His Leu Val Pro Glu Gln Ala Leu Ile Pro Leu
305                 310              315                 320

Lys Pro Arg Asp Leu Gln Ile Ala Lys Ser Leu Met Ser Ser Glu Val
                325              330              335

Leu Gln Asp Glu Tyr Arg Glu Glu Leu Ala Ser Met Ile Glu Ser Gly
                340              345              350

Gln Arg Ala Glu Ile Glu Ala Leu Phe Phe His Gly Tyr Asp Tyr Leu
                355              360              365

Gly Lys Tyr Ile Ala Lys Lys Val Val Gln Ala Asn Tyr Ile
                370              375              380

<210> SEQ ID NO 22
<211> LENGTH: 1352
<212> TYPE: PRT
<213> ORGANISM: Parcubacteria

<400> SEQUENCE: 22

Met Glu Asn Ile Phe Asp Gln Phe Ile Gly Lys Tyr Ser Leu Ser Lys
1               5               10              15

Thr Leu Arg Phe Glu Leu Lys Pro Val Gly Lys Thr Glu Asp Phe Leu
                20              25              30

Lys Ile Asn Lys Val Phe Glu Lys Asp Gln Thr Ile Asp Asp Ser Tyr
                35              40              45

Asn Gln Ala Lys Phe Tyr Phe Asp Ser Leu His Gln Lys Phe Ile Asp
        50              55              60

Ala Ala Leu Ala Ser Asp Lys Thr Ser Glu Leu Ser Phe Gln Asn Phe
65                  70              75                  80

Ala Asp Val Leu Glu Lys Gln Asn Lys Ile Ile Leu Asp Lys Lys Arg
                85              90              95

Glu Met Gly Ala Leu Arg Lys Arg Asp Lys Asn Ala Val Gly Ile Asp
                100             105             110

Arg Leu Gln Lys Glu Ile Asn Asp Ala Glu Asp Ile Ile Gln Lys Glu
        115             120             125

Lys Glu Lys Ile Tyr Lys Asp Val Arg Thr Leu Phe Asp Asn Glu Ala
        130             135             140

Glu Ser Trp Lys Thr Tyr Tyr Gln Glu Arg Glu Val Asp Gly Lys Lys
145             150             155             160

Ile Thr Phe Ser Lys Ala Asp Leu Lys Gln Lys Gly Ala Asp Phe Leu
                165             170             175

Thr Ala Ala Gly Ile Leu Lys Val Leu Lys Tyr Glu Phe Pro Glu Glu
                180             185             190

Lys Glu Lys Glu Phe Gln Ala Lys Asn Gln Pro Ser Leu Phe Val Glu
        195             200             205
```

```
Glu Lys Glu Asn Pro Gly Gln Lys Arg Tyr Ile Phe Asp Ser Phe Asp
    210             215                 220

Lys Phe Ala Gly Tyr Leu Thr Lys Phe Gln Gln Thr Lys Lys Asn Leu
225             230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
            260                 265                 270

Lys Asn Asn His Thr Asp Leu Gly Phe Asp Glu Glu Asn Ile Phe Glu
        275                 280                 285

Ile Glu Arg Tyr Lys Asn Cys Leu Leu Gln Arg Glu Ile Glu His Ile
    290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
    370                 375                 380

Glu Arg Phe Thr Ala Ala Lys Lys Leu Met Asn Ala Phe Cys Asn Gly
385                 390                 395                 400

Glu Phe Glu Ser Glu Tyr Glu Gly Ile Tyr Leu Lys Asn Lys Ala Ile
                405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
    450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
                500                 505                 510

Lys Leu Leu Gly Tyr Asp Ser Cys Leu Lys Ile Ala Lys Gln Leu Gly
            515                 520                 525

Ile Phe Pro Gln Glu Lys Glu Ala Arg Glu Lys Ala Thr Ala Val Ile
        530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
        595                 600                 605

Asp Glu Asp Lys Ile Lys Leu Asn Phe Glu Asn Gly Ala Leu Leu Lys
    610                 615                 620

Gly Trp Asp Glu Asn Lys Glu Tyr Asp Phe Met Gly Val Ile Leu Lys
```

```
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
                660                 665                 670

Gln Lys Met Ile Tyr Lys Gln Ile Ala Asp Ala Ser Lys Asp Val Pro
                675                 680                 685

Arg Leu Leu Leu Thr Ser Lys Lys Ala Met Glu Lys Phe Lys Pro Ser
    690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
                725                 730                 735

Asn Cys Ile Pro Gln Tyr Ser Asn Trp Ser Phe Tyr Asp Phe Gln Phe
                740                 745                 750

Gln Asp Thr Gly Lys Tyr Gln Asn Ile Lys Glu Phe Thr Asp Asp Val
                755                 760                 765

Gln Lys Tyr Gly Tyr Lys Ile Ser Phe Arg Asp Ile Asp Asp Glu Tyr
    770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
                805                 810                 815

Leu Tyr Phe Glu His Ile Leu Ser Ala Glu Asn Leu Asn Asp Pro Val
                820                 825                 830

Phe Lys Leu Ser Gly Met Ala Glu Ile Phe Gln Arg Gln Pro Ser Val
                835                 840                 845

Asn Glu Arg Glu Lys Ile Thr Thr Gln Lys Asn Gln Cys Ile Leu Asp
    850                 855                 860

Lys Gly Asp Arg Ala Tyr Lys Tyr Arg Arg Tyr Thr Glu Lys Lys Ile
865                 870                 875                 880

Met Phe His Met Ser Leu Val Leu Asn Thr Gly Lys Gly Glu Ile Lys
                885                 890                 895

Gln Val Gln Phe Asn Lys Ile Ile Asn Gln Arg Ile Ser Ser Ser Asp
                900                 905                 910

Asn Glu Met Arg Val Asn Val Ile Gly Ile Asp Arg Gly Glu Lys Asn
                915                 920                 925

Leu Leu Tyr Tyr Ser Val Val Lys Gln Asn Gly Glu Ile Ile Glu Gln
    930                 935                 940

Ala Ser Leu Asn Glu Ile Asn Gly Val Asn Tyr Arg Asp Lys Leu Ile
945                 950                 955                 960

Glu Arg Glu Lys Glu Arg Leu Lys Asn Arg Gln Ser Trp Lys Pro Val
                965                 970                 975

Val Lys Ile Lys Asp Leu Lys Lys Gly Tyr Ile Ser His Val Ile His
                980                 985                 990

Lys Ile Cys Gln Leu Ile Glu Lys  Tyr Ser Ala Ile Val  Val Leu Glu
        995                 1000                1005

Asp Leu  Asn Met Arg Phe Lys  Gln Ile Arg Gly Gly  Ile Glu Arg
    1010                1015                1020

Ser Val  Tyr Gln Gln Phe Glu  Lys Ala Leu Ile Asp  Lys Leu Gly
    1025                1030                1035

Tyr Leu  Val Phe Lys Asp Asn  Arg Asp Leu Arg Ala  Pro Gly Gly
    1040                1045                1050
```

-continued

```
Val Leu  Asn Gly Tyr Gln Leu  Ser Ala Pro Phe Val  Ser Phe Glu
    1055             1060             1065

Lys Met  Arg Lys Gln Thr Gly  Ile Leu Phe Tyr Thr  Gln Ala Glu
    1070             1075             1080

Tyr Thr  Ser Lys Thr Asp Pro  Ile Thr Gly Phe Arg  Lys Asn Val
    1085             1090             1095

Tyr Ile  Ser Asn Ser Ala Ser  Leu Asp Lys Ile Lys  Glu Ala Val
    1100             1105             1110

Lys Lys  Phe Asp Ala Ile Gly  Trp Asp Gly Lys Glu  Gln Ser Tyr
    1115             1120             1125

Phe Phe  Lys Tyr Asn Pro Tyr  Asn Leu Ala Asp Glu  Lys Tyr Lys
    1130             1135             1140

Asn Ser  Thr Val Ser Lys Glu  Trp Ala Ile Phe Ala  Ser Ala Pro
    1145             1150             1155

Arg Ile  Arg Arg Gln Lys Gly  Glu Asp Gly Tyr Trp  Lys Tyr Asp
    1160             1165             1170

Arg Val  Lys Val Asn Glu Glu  Phe Glu Lys Leu Leu  Lys Val Trp
    1175             1180             1185

Asn Phe  Val Asn Pro Lys Ala  Thr Asp Ile Lys Gln  Glu Ile Ile
    1190             1195             1200

Lys Lys  Glu Lys Ala Gly Asp  Leu Gln Gly Glu Lys  Glu Leu Asp
    1205             1210             1215

Gly Arg  Leu Arg Asn Phe Trp  His Ser Phe Ile Tyr  Leu Phe Asn
    1220             1225             1230

Leu Val  Leu Glu Leu Arg Asn  Ser Phe Ser Leu Gln  Ile Lys Ile
    1235             1240             1245

Lys Ala  Gly Glu Val Ile Ala  Val Asp Glu Gly Val  Asp Phe Ile
    1250             1255             1260

Ala Ser  Pro Val Lys Pro Phe  Phe Thr Thr Pro Asn  Pro Tyr Ile
    1265             1270             1275

Pro Ser  Asn Leu Cys Trp Leu  Ala Val Glu Asn Ala  Asp Ala Asn
    1280             1285             1290

Gly Ala  Tyr Asn Ile Ala Arg  Lys Gly Val Met Ile  Leu Lys Lys
    1295             1300             1305

Ile Arg  Glu His Ala Lys Lys  Asp Pro Glu Phe Lys  Lys Leu Pro
    1310             1315             1320

Asn Leu  Phe Ile Ser Asn Ala  Glu Trp Asp Glu Ala  Ala Arg Asp
    1325             1330             1335

Trp Gly  Lys Tyr Ala Gly Thr  Thr Ala Leu Asn Leu  Asp His
    1340             1345             1350
```

<210> SEQ ID NO 23
<211> LENGTH: 1477
<212> TYPE: PRT
<213> ORGANISM: Candidatus Peregrinibacteria

<400> SEQUENCE: 23

```
Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
            20                  25                  30

Lys Asp His Leu Glu Tyr Asp Glu Lys Leu Gln Thr Phe Leu Lys Asp
        35                  40                  45

Gln Asn Ile Asp Asp Ala Tyr Gln Ala Leu Lys Pro Gln Phe Asp Glu
```

```
          50                    55                    60

Ile His Glu Glu Phe Ile Thr Asp Ser Leu Glu Ser Lys Lys Ala Lys
65                    70                    75                    80

Glu Ile Asp Phe Ser Glu Tyr Leu Asp Leu Phe Gln Glu Lys Lys Glu
                 85                    90                    95

Leu Asn Asp Ser Glu Lys Lys Leu Arg Asn Lys Ile Gly Glu Thr Phe
                 100                   105                   110

Asn Lys Ala Gly Glu Lys Trp Lys Lys Glu Lys Tyr Pro Gln Tyr Glu
             115                   120                   125

Trp Lys Lys Gly Ser Lys Ile Ala Asn Gly Ala Asp Ile Leu Ser Cys
         130                   135                   140

Gln Asp Met Leu Gln Phe Ile Lys Tyr Lys Asn Pro Glu Asp Glu Lys
145                   150                   155                   160

Ile Lys Asn Tyr Ile Asp Asp Thr Leu Lys Gly Phe Phe Thr Tyr Phe
                 165                   170                   175

Gly Gly Phe Asn Gln Asn Arg Ala Asn Tyr Tyr Glu Thr Lys Lys Glu
             180                   185                   190

Ala Ser Thr Ala Val Ala Thr Arg Ile Val His Glu Asn Leu Pro Lys
         195                   200                   205

Phe Cys Asp Asn Val Ile Gln Phe Lys His Ile Ile Lys Arg Lys Lys
         210                   215                   220

Asp Gly Thr Val Glu Lys Thr Glu Arg Lys Thr Glu Tyr Leu Asn Ala
225                   230                   235                   240

Tyr Gln Tyr Leu Lys Asn Asn Asn Lys Ile Thr Gln Ile Lys Asp Ala
             245                   250                   255

Glu Thr Glu Lys Met Ile Glu Ser Thr Pro Ile Ala Glu Lys Ile Phe
             260                   265                   270

Asp Val Tyr Tyr Phe Ser Ser Cys Leu Ser Gln Lys Gln Ile Glu Glu
             275                   280                   285

Tyr Asn Arg Ile Ile Gly His Tyr Asn Leu Leu Ile Asn Leu Tyr Asn
         290                   295                   300

Gln Ala Lys Arg Ser Glu Gly Lys His Leu Ser Ala Asn Glu Lys Lys
305                   310                   315                   320

Tyr Lys Asp Leu Pro Lys Phe Lys Thr Leu Tyr Lys Gln Ile Gly Cys
                 325                   330                   335

Gly Lys Lys Lys Asp Leu Phe Tyr Thr Ile Lys Cys Asp Thr Glu Glu
             340                   345                   350

Glu Ala Asn Lys Ser Arg Asn Glu Gly Lys Glu Ser His Ser Val Glu
             355                   360                   365

Glu Ile Ile Asn Lys Ala Gln Glu Ala Ile Asn Lys Tyr Phe Lys Ser
         370                   375                   380

Asn Asn Asp Cys Glu Asn Ile Asn Thr Val Pro Asp Phe Ile Asn Tyr
385                   390                   395                   400

Ile Leu Thr Lys Glu Asn Tyr Glu Gly Val Tyr Trp Ser Lys Ala Ala
                 405                   410                   415

Met Asn Thr Ile Ser Asp Lys Tyr Phe Ala Asn Tyr His Asp Leu Gln
                 420                   425                   430

Asp Arg Leu Lys Glu Ala Lys Val Phe Gln Lys Ala Asp Lys Lys Ser
             435                   440                   445

Glu Asp Asp Ile Lys Ile Pro Glu Ala Ile Glu Leu Ser Gly Leu Phe
         450                   455                   460

Gly Val Leu Asp Ser Leu Ala Asp Trp Gln Thr Thr Leu Phe Lys Ser
465                   470                   475                   480
```

-continued

```
Ser Ile Leu Ser Asn Glu Asp Lys Leu Lys Ile Ile Thr Asp Ser Gln
            485             490             495

Thr Pro Ser Glu Ala Leu Leu Lys Met Ile Phe Asn Asp Ile Glu Lys
            500             505             510

Asn Met Glu Ser Phe Leu Lys Glu Thr Asn Asp Ile Ile Thr Leu Lys
            515             520             525

Lys Tyr Lys Gly Asn Lys Glu Gly Thr Glu Lys Ile Lys Gln Trp Phe
        530             535             540

Asp Tyr Thr Leu Ala Ile Asn Arg Met Leu Lys Tyr Phe Leu Val Lys
545             550             555             560

Glu Asn Lys Ile Lys Gly Asn Ser Leu Asp Thr Asn Ile Ser Glu Ala
            565             570             575

Leu Lys Thr Leu Ile Tyr Ser Asp Asp Ala Glu Trp Phe Lys Trp Tyr
            580             585             590

Asp Ala Leu Arg Asn Tyr Leu Thr Gln Lys Pro Gln Asp Glu Ala Lys
        595             600             605

Glu Asn Lys Leu Lys Leu Asn Phe Asp Asn Pro Ser Leu Ala Gly Gly
        610             615             620

Trp Asp Val Asn Lys Glu Cys Ser Asn Phe Cys Val Ile Leu Lys Asp
625             630             635             640

Lys Asn Glu Lys Lys Tyr Leu Ala Ile Met Lys Lys Gly Glu Asn Thr
            645             650             655

Leu Phe Gln Lys Glu Trp Thr Glu Gly Arg Gly Lys Asn Leu Thr Lys
            660             665             670

Lys Ser Asn Pro Leu Phe Glu Ile Asn Asn Cys Glu Ile Leu Ser Lys
        675             680             685

Met Glu Tyr Asp Phe Trp Ala Asp Val Ser Lys Met Ile Pro Lys Cys
        690             695             700

Ser Thr Gln Leu Lys Ala Val Val Asn His Phe Lys Gln Ser Asp Asn
705             710             715             720

Glu Phe Ile Phe Pro Ile Gly Tyr Lys Val Thr Ser Gly Glu Lys Phe
            725             730             735

Arg Glu Glu Cys Lys Ile Ser Lys Gln Asp Phe Glu Leu Asn Asn Lys
            740             745             750

Val Phe Asn Lys Asn Glu Leu Ser Val Thr Ala Met Arg Tyr Asp Leu
        755             760             765

Ser Ser Thr Gln Glu Lys Gln Tyr Ile Lys Ala Phe Gln Lys Glu Tyr
        770             775             780

Trp Glu Leu Leu Phe Lys Gln Glu Lys Arg Asp Thr Lys Leu Thr Asn
785             790             795             800

Asn Glu Ile Phe Asn Glu Trp Ile Asn Phe Cys Asn Lys Lys Tyr Ser
            805             810             815

Glu Leu Leu Ser Trp Glu Arg Lys Tyr Lys Asp Ala Leu Thr Asn Trp
        820             825             830

Ile Asn Phe Cys Lys Tyr Phe Leu Ser Lys Tyr Pro Lys Thr Thr Leu
        835             840             845

Phe Asn Tyr Ser Phe Lys Glu Ser Glu Asn Tyr Asn Ser Leu Asp Glu
    850             855             860

Phe Tyr Arg Asp Val Asp Ile Cys Ser Tyr Lys Leu Asn Ile Asn Thr
865             870             875             880

Thr Ile Asn Lys Ser Ile Leu Asp Arg Leu Val Glu Glu Gly Lys Leu
            885             890             895
```

```
Tyr Leu Phe Glu Ile Lys Asn Gln Asp Ser Asn Asp Gly Lys Ser Ile
        900                 905                 910

Gly His Lys Asn Asn Leu His Thr Ile Tyr Trp Asn Ala Ile Phe Glu
        915                 920                 925

Asn Phe Asp Asn Arg Pro Lys Leu Asn Gly Glu Ala Glu Ile Phe Tyr
    930                 935                 940

Arg Lys Ala Ile Ser Lys Asp Lys Leu Gly Ile Val Lys Gly Lys Lys
945                 950                 955                 960

Thr Lys Asn Gly Thr Glu Ile Ile Lys Asn Tyr Arg Phe Ser Lys Glu
                965                 970                 975

Lys Phe Ile Leu His Val Pro Ile Thr Leu Asn Phe Cys Ser Asn Asn
        980                 985                 990

Glu Tyr Val Asn Asp Ile Val Asn  Thr Lys Phe Tyr Asn  Phe Ser Asn
        995                 1000                1005

Leu His  Phe Leu Gly Ile Asp  Arg Gly Glu Lys His  Leu Ala Tyr
    1010                1015                1020

Tyr Ser  Leu Val Asn Lys Asn  Gly Glu Ile Val Asp  Gln Gly Thr
    1025                1030                1035

Leu Asn  Leu Pro Phe Thr Asp  Lys Asp Gly Asn Gln  Arg Ser Ile
    1040                1045                1050

Lys Lys  Glu Lys Tyr Phe Tyr  Asn Lys Gln Glu Asp  Lys Trp Glu
    1055                1060                1065

Ala Lys  Glu Val Asp Cys Trp  Asn Tyr Asn Asp Leu  Leu Asp Ala
    1070                1075                1080

Met Ala  Ser Asn Arg Asp Met  Ala Arg Lys Asn Trp  Gln Arg Ile
    1085                1090                1095

Gly Thr  Ile Lys Glu Ala Lys  Asn Gly Tyr Val Ser  Leu Val Ile
    1100                1105                1110

Arg Lys  Ile Ala Asp Leu Ala  Val Asn Asn Glu Arg  Pro Ala Phe
    1115                1120                1125

Ile Val  Leu Glu Asp Leu Asn  Thr Gly Phe Lys Arg  Ser Arg Gln
    1130                1135                1140

Lys Ile  Asp Lys Ser Val Tyr  Gln Lys Phe Glu Leu  Ala Leu Ala
    1145                1150                1155

Lys Lys  Leu Asn Phe Leu Val  Asp Lys Asn Ala Lys  Arg Asp Glu
    1160                1165                1170

Ile Gly  Ser Pro Thr Lys Ala  Leu Gln Leu Thr Pro  Pro Val Asn
    1175                1180                1185

Asn Tyr  Gly Asp Ile Glu Asn  Lys Lys Gln Ala Gly  Ile Met Leu
    1190                1195                1200

Tyr Thr  Arg Ala Asn Tyr Thr  Ser Gln Thr Asp Pro  Ala Thr Gly
    1205                1210                1215

Trp Arg  Lys Thr Ile Tyr Leu  Lys Ala Gly Pro Glu  Glu Thr Thr
    1220                1225                1230

Tyr Lys  Lys Asp Gly Lys Ile  Lys Asn Lys Ser Val  Lys Asp Gln
    1235                1240                1245

Ile Ile  Glu Thr Phe Thr Asp  Ile Gly Phe Asp Gly  Lys Asp Tyr
    1250                1255                1260

Tyr Phe  Glu Tyr Asp Lys Gly  Glu Phe Val Asp Glu  Lys Thr Gly
    1265                1270                1275

Glu Ile  Lys Pro Lys Lys Trp  Arg Leu Tyr Ser Gly  Glu Asn Gly
    1280                1285                1290

Lys Ser  Leu Asp Arg Phe Arg  Gly Glu Arg Glu Lys  Asp Lys Tyr
```

-continued

```
            1295                1300                1305

Glu Trp  Lys Ile Asp Lys Ile  Asp Ile Val Lys Ile  Leu Asp Asp
   1310                1315                1320

Leu Phe  Val Asn Phe Asp Lys  Asn Ile Ser Leu Leu  Lys Gln Leu
   1325                1330                1335

Lys Glu  Gly Val Glu Leu Thr  Arg Asn Asn Glu His  Gly Thr Gly
   1340                1345                1350

Glu Ser  Leu Arg Phe Ala Ile  Asn Leu Ile Gln Gln  Ile Arg Asn
   1355                1360                1365

Thr Gly  Asn Asn Glu Arg Asp  Asn Asp Phe Ile Leu  Ser Pro Val
   1370                1375                1380

Arg Asp  Glu Asn Gly Lys His  Phe Asp Ser Arg Glu  Tyr Trp Asp
   1385                1390                1395

Lys Glu  Thr Lys Gly Glu Lys  Ile Ser Met Pro Ser  Ser Gly Asp
   1400                1405                1410

Ala Asn  Gly Ala Phe Asn Ile  Ala Arg Lys Gly Ile  Ile Met Asn
   1415                1420                1425

Ala His  Ile Leu Ala Asn Ser  Asp Ser Lys Asp Leu  Ser Leu Phe
   1430                1435                1440

Val Ser  Asp Glu Glu Trp Asp  Leu His Leu Asn Asn  Lys Thr Glu
   1445                1450                1455

Trp Lys  Lys Gln Leu Asn Ile  Phe Ser Ser Arg Lys  Ala Met Ala
   1460                1465                1470

Lys Arg  Lys Lys
   1475

<210> SEQ ID NO 24
<211> LENGTH: 1307
<212> TYPE: PRT
<213> ORGANISM: Acidaminococcus

<400> SEQUENCE: 24

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
            115                 120                 125

Tyr Lys Gly Leu Phe Lys Ala Glu Leu Phe Asn Gly Lys Val Leu Lys
        130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175
```

```
Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
            245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
            275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
            325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
            405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
            485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
            565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
```

-continued

```
              595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
                675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
                740                 745                 750

Gly His His Gly Lys Pro Asn Leu His Thr Leu Tyr Trp Thr Gly Leu
                755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
                820                 825                 830

Arg Leu Ser His Asp Leu Ser Asp Glu Ala Arg Ala Leu Leu Pro Asn
                835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
                900                 905                 910

Asn Leu Ile Tyr Ile Thr Val Ile Asp Ser Thr Gly Lys Ile Leu Glu
                915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
                980                 985                 990

Glu Asn Leu Asn Phe Gly Phe Lys  Ser Lys Arg Thr Gly  Ile Ala Glu
    995                 1000                 1005

Lys Ala  Val Tyr Gln Gln Phe  Glu Lys Met Leu Ile  Asp Lys Leu
    1010                 1015                 1020
```

```
Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290

Ser Asn  Gln Asp Trp Leu Ala  Tyr Ile Gln Glu Leu  Arg Asn
    1295                1300                1305
```

```
<210> SEQ ID NO 25
<211> LENGTH: 1246
<212> TYPE: PRT
<213> ORGANISM: Porphyromonas macacae

<400> SEQUENCE: 25

Met Lys Thr Gln His Phe Phe Glu Asp Phe Thr Ser Leu Tyr Ser Leu
1               5                   10                  15

Ser Lys Thr Ile Arg Phe Glu Leu Lys Pro Ile Gly Lys Thr Leu Glu
            20                  25                  30

Asn Ile Lys Lys Asn Gly Leu Ile Arg Arg Asp Glu Gln Arg Leu Asp
        35                  40                  45

Asp Tyr Glu Lys Leu Lys Lys Val Ile Asp Glu Tyr His Glu Asp Phe
    50                  55                  60

Ile Ala Asn Ile Leu Ser Ser Phe Ser Phe Ser Glu Glu Ile Leu Gln
```

-continued

```
65                    70                    75                    80

Ser Tyr Ile Gln Asn Leu Ser Glu Ser Glu Ala Arg Ala Lys Ile Glu
                85                    90                    95

Lys Thr Met Arg Asp Thr Leu Ala Lys Ala Phe Ser Glu Asp Glu Arg
                100                   105                   110

Tyr Lys Ser Ile Phe Lys Lys Glu Leu Val Lys Lys Asp Ile Pro Val
                115                   120                   125

Trp Cys Pro Ala Tyr Lys Ser Leu Cys Lys Lys Phe Asp Asn Phe Thr
        130                   135                   140

Thr Ser Leu Val Pro Phe His Glu Asn Arg Lys Asn Leu Tyr Thr Ser
145                   150                   155                   160

Asn Glu Ile Thr Ala Ser Ile Pro Tyr Arg Ile Val His Val Asn Leu
                165                   170                   175

Pro Lys Phe Ile Gln Asn Ile Glu Ala Leu Cys Glu Leu Gln Lys Lys
                180                   185                   190

Met Gly Ala Asp Leu Tyr Leu Glu Met Met Glu Asn Leu Arg Asn Val
                195                   200                   205

Trp Pro Ser Phe Val Lys Thr Pro Asp Asp Leu Cys Asn Leu Lys Thr
        210                   215                   220

Tyr Asn His Leu Met Val Gln Ser Ser Ile Ser Glu Tyr Asn Arg Phe
225                   230                   235                   240

Val Gly Gly Tyr Ser Thr Glu Asp Gly Thr Lys His Gln Gly Ile Asn
                245                   250                   255

Glu Trp Ile Asn Ile Tyr Arg Gln Arg Asn Lys Glu Met Arg Leu Pro
                260                   265                   270

Gly Leu Val Phe Leu His Lys Gln Ile Leu Ala Lys Val Asp Ser Ser
                275                   280                   285

Ser Phe Ile Ser Asp Thr Leu Glu Asn Asp Asp Gln Val Phe Cys Val
        290                   295                   300

Leu Arg Gln Phe Arg Lys Leu Phe Trp Asn Thr Val Ser Ser Lys Glu
305                   310                   315                   320

Asp Asp Ala Ala Ser Leu Lys Asp Leu Phe Cys Gly Leu Ser Gly Tyr
                325                   330                   335

Asp Pro Glu Ala Ile Tyr Val Ser Asp Ala His Leu Ala Thr Ile Ser
                340                   345                   350

Lys Asn Ile Phe Asp Arg Trp Asn Tyr Ile Ser Asp Ala Ile Arg Arg
                355                   360                   365

Lys Thr Glu Val Leu Met Pro Arg Lys Lys Glu Ser Val Glu Arg Tyr
        370                   375                   380

Ala Glu Lys Ile Ser Lys Gln Ile Lys Lys Arg Gln Ser Tyr Ser Leu
385                   390                   395                   400

Ala Glu Leu Asp Asp Leu Leu Ala His Tyr Ser Glu Glu Ser Leu Pro
                405                   410                   415

Ala Gly Phe Ser Leu Leu Ser Tyr Phe Thr Ser Leu Gly Gly Gln Lys
                420                   425                   430

Tyr Leu Val Ser Asp Gly Glu Val Ile Leu Tyr Glu Glu Gly Ser Asn
                435                   440                   445

Ile Trp Asp Glu Val Leu Ile Ala Phe Arg Asp Leu Gln Val Ile Leu
        450                   455                   460

Asp Lys Asp Phe Thr Glu Lys Lys Leu Gly Lys Asp Glu Glu Ala Val
465                   470                   475                   480

Ser Val Ile Lys Lys Ala Leu Asp Ser Ala Leu Arg Leu Arg Lys Phe
                485                   490                   495
```

-continued

```
Phe Asp Leu Leu Ser Gly Thr Gly Ala Glu Ile Arg Arg Asp Ser Ser
        500                 505                 510

Phe Tyr Ala Leu Tyr Thr Asp Arg Met Asp Lys Leu Lys Gly Leu Leu
        515                 520                 525

Lys Met Tyr Asp Lys Val Arg Asn Tyr Leu Thr Lys Lys Pro Tyr Ser
        530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
        595                 600                 605

Met Glu Tyr Lys Gln Ile Ala Glu Pro Met Leu Met Leu Pro Lys Val
        610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
                660                 665                 670

Thr Val His Glu Trp Lys Leu Phe Asn Phe Ser Phe Ser Pro Thr Glu
            675                 680                 685

Gln Tyr Arg Asn Ile Gly Glu Phe Phe Asp Glu Val Arg Glu Gln Ala
        690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
                740                 745                 750

Ala Leu Phe Ser Glu Gln Asn Gln Ser Arg Val Tyr Lys Leu Cys Gly
        755                 760                 765

Gly Gly Glu Leu Phe Tyr Arg Lys Ala Ser Leu His Met Gln Asp Thr
        770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe Phe His Val Pro Ile Ser Ile Asn Tyr
            820                 825                 830

Lys Asn Lys Lys Ile Thr Asn Val Asn Gln Met Val Arg Asp Tyr Ile
        835                 840                 845

Ala Gln Asn Asp Asp Leu Gln Ile Ile Gly Ile Asp Arg Gly Glu Arg
        850                 855                 860

Asn Leu Leu Tyr Ile Ser Arg Ile Asp Thr Arg Gly Asn Leu Leu Glu
865                 870                 875                 880

Gln Phe Ser Leu Asn Val Ile Glu Ser Asp Lys Gly Asp Leu Arg Thr
                885                 890                 895

Asp Tyr Gln Lys Ile Leu Gly Asp Arg Glu Gln Glu Arg Leu Arg Arg
            900                 905                 910
```

-continued

```
Arg Gln Glu Trp Lys Ser Ile Glu Ser Ile Lys Asp Leu Lys Asp Gly
        915                 920                 925

Tyr Met Ser Gln Val Val His Lys Ile Cys Asn Met Val Val Glu His
    930                 935                 940

Lys Ala Ile Val Val Leu Glu Asn Leu Asn Leu Ser Phe Met Lys Gly
945                 950                 955                 960

Arg Lys Lys Val Glu Lys Ser Val Tyr Glu Lys Phe Glu Arg Met Leu
                965                 970                 975

Val Asp Lys Leu Asn Tyr Leu Val Val Asp Lys Lys Asn Leu Ser Asn
            980                 985                 990

Glu Pro Gly Gly Leu Tyr Ala Ala  Tyr Gln Leu Thr Asn  Pro Leu Phe
        995                 1000                1005

Ser Phe  Glu Glu Leu His Arg  Tyr Pro Gln Ser Gly  Ile Leu Phe
    1010                1015                1020

Phe Val  Asp Pro Trp Asn Thr  Ser Leu Thr Asp Pro  Ser Thr Gly
    1025                1030                1035

Phe Val  Asn Leu Leu Gly Arg  Ile Asn Tyr Thr Asn  Val Gly Asp
    1040                1045                1050

Ala Arg  Lys Phe Phe Asp Arg  Phe Asn Ala Ile Arg  Tyr Asp Gly
    1055                1060                1065

Lys Gly  Asn Ile Leu Phe Asp  Leu Asp Leu Ser Arg  Phe Asp Val
    1070                1075                1080

Arg Val  Glu Thr Gln Arg Lys  Leu Trp Thr Leu Thr  Thr Phe Gly
    1085                1090                1095

Ser Arg  Ile Ala Lys Ser Lys  Lys Ser Gly Lys Trp  Met Val Glu
    1100                1105                1110

Arg Ile  Glu Asn Leu Ser Leu  Cys Phe Leu Glu Leu  Phe Glu Gln
    1115                1120                1125

Phe Asn  Ile Gly Tyr Arg Val  Glu Lys Asp Leu Lys  Lys Ala Ile
    1130                1135                1140

Leu Ser  Gln Asp Arg Lys Glu  Phe Tyr Val Arg Leu  Ile Tyr Leu
    1145                1150                1155

Phe Asn  Leu Met Met Gln Ile  Arg Asn Ser Asp Gly  Glu Glu Asp
    1160                1165                1170

Tyr Ile  Leu Ser Pro Ala Leu  Asn Glu Lys Asn Leu  Gln Phe Asp
    1175                1180                1185

Ser Arg  Leu Ile Glu Ala Lys  Asp Leu Pro Val Asp  Ala Asp Ala
    1190                1195                1200

Asn Gly  Ala Tyr Asn Val Ala  Arg Lys Gly Leu Met  Val Val Gln
    1205                1210                1215

Arg Ile  Lys Arg Gly Asp His  Glu Ser Ile His Arg  Ile Gly Arg
    1220                1225                1230

Ala Gln  Trp Leu Arg Tyr Val  Gln Glu Gly Ile Val  Glu
    1235                1240                1245
```

```
<210> SEQ ID NO 26
<211> LENGTH: 1260
<212> TYPE: PRT
<213> ORGANISM: Porphyromonas crevioricanis

<400> SEQUENCE: 26

Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
            20                  25                  30
```

```
Lys Ala Gly Ile Leu Lys Glu Asp Glu His Arg Ala Glu Ser Tyr Arg
         35              40                  45

Arg Val Lys Lys Ile Ile Asp Thr Tyr His Lys Val Phe Ile Asp Ser
     50              55                  60

Ser Leu Glu Asn Met Ala Lys Met Gly Ile Glu Asn Glu Ile Lys Ala
65              70                  75                  80

Met Leu Gln Ser Phe Cys Glu Leu Tyr Lys Lys Asp His Arg Thr Glu
             85              90                  95

Gly Glu Asp Lys Ala Leu Asp Lys Ile Arg Ala Val Leu Arg Gly Leu
            100             105                 110

Ile Val Gly Ala Phe Thr Gly Val Cys Gly Arg Arg Glu Asn Thr Val
            115             120                 125

Gln Asn Glu Lys Tyr Glu Ser Leu Phe Lys Glu Lys Leu Ile Lys Glu
        130             135                 140

Ile Leu Pro Asp Phe Val Leu Ser Thr Glu Ala Glu Ser Leu Pro Phe
145             150                 155                 160

Ser Val Glu Glu Ala Thr Arg Ser Leu Lys Glu Phe Asp Ser Phe Thr
            165             170                 175

Ser Tyr Phe Ala Gly Phe Tyr Glu Asn Arg Lys Asn Ile Tyr Ser Thr
            180             185                 190

Lys Pro Gln Ser Thr Ala Ile Ala Tyr Arg Leu Ile His Glu Asn Leu
        195             200                 205

Pro Lys Phe Ile Asp Asn Ile Leu Val Phe Gln Lys Ile Lys Glu Pro
        210             215                 220

Ile Ala Lys Glu Leu Glu His Ile Arg Ala Asp Phe Ser Ala Gly Gly
225             230                 235                 240

Tyr Ile Lys Lys Asp Glu Arg Leu Glu Asp Ile Phe Ser Leu Asn Tyr
            245             250                 255

Tyr Ile His Val Leu Ser Gln Ala Gly Ile Glu Lys Tyr Asn Ala Leu
            260             265                 270

Ile Gly Lys Ile Val Thr Glu Gly Asp Gly Glu Met Lys Gly Leu Asn
        275             280                 285

Glu His Ile Asn Leu Tyr Asn Gln Gln Arg Gly Arg Glu Asp Arg Leu
        290             295                 300

Pro Leu Phe Arg Pro Leu Tyr Lys Gln Ile Leu Ser Asp Arg Glu Gln
305             310                 315                 320

Leu Ser Tyr Leu Pro Glu Ser Phe Glu Lys Asp Glu Glu Leu Leu Arg
            325             330                 335

Ala Leu Lys Glu Phe Tyr Asp His Ile Ala Glu Asp Ile Leu Gly Arg
            340             345                 350

Thr Gln Gln Leu Met Thr Ser Ile Ser Glu Tyr Asp Leu Ser Arg Ile
        355             360                 365

Tyr Val Arg Asn Asp Ser Gln Leu Thr Asp Ile Ser Lys Lys Met Leu
    370             375                 380

Gly Asp Trp Asn Ala Ile Tyr Met Ala Arg Glu Arg Ala Tyr Asp His
385             390                 395                 400

Glu Gln Ala Pro Lys Arg Ile Thr Ala Lys Tyr Glu Arg Asp Arg Ile
            405             410                 415

Lys Ala Leu Lys Gly Glu Glu Ser Ile Ser Leu Ala Asn Leu Asn Ser
            420             425                 430

Cys Ile Ala Phe Leu Asp Asn Val Arg Asp Cys Arg Val Asp Thr Tyr
            435             440                 445
```

-continued

```
Leu Ser Thr Leu Gly Gln Lys Glu Gly Pro His Gly Leu Ser Asn Leu
    450             455             460

Val Glu Asn Val Phe Ala Ser Tyr His Glu Ala Glu Gln Leu Leu Ser
465             470             475             480

Phe Pro Tyr Pro Glu Glu Asn Asn Leu Ile Gln Asp Lys Asp Asn Val
            485             490             495

Val Leu Ile Lys Asn Leu Leu Asp Asn Ile Ser Asp Leu Gln Arg Phe
            500             505             510

Leu Lys Pro Leu Trp Gly Met Gly Asp Glu Pro Asp Lys Asp Glu Arg
        515             520             525

Phe Tyr Gly Glu Tyr Asn Tyr Ile Arg Gly Ala Leu Asp Gln Val Ile
    530             535             540

Pro Leu Tyr Asn Lys Val Arg Asn Tyr Leu Thr Arg Lys Pro Tyr Ser
545             550             555             560

Thr Arg Lys Val Lys Leu Asn Phe Gly Asn Ser Gln Leu Leu Ser Gly
            565             570             575

Trp Asp Arg Asn Lys Glu Lys Asp Asn Ser Cys Val Ile Leu Arg Lys
        580             585             590

Gly Gln Asn Phe Tyr Leu Ala Ile Met Asn Asn Arg His Lys Arg Ser
    595             600             605

Phe Glu Asn Lys Met Leu Pro Glu Tyr Lys Glu Gly Glu Pro Tyr Phe
    610             615             620

Glu Lys Met Asp Tyr Lys Phe Leu Pro Asp Pro Asn Lys Met Leu Pro
625             630             635             640

Lys Val Phe Leu Ser Lys Lys Gly Ile Glu Ile Tyr Lys Pro Ser Pro
            645             650             655

Lys Leu Leu Glu Gln Tyr Gly His Gly Thr His Lys Lys Gly Asp Thr
            660             665             670

Phe Ser Met Asp Asp Leu His Glu Leu Ile Asp Phe Phe Lys His Ser
    675             680             685

Ile Glu Ala His Glu Asp Trp Lys Gln Phe Gly Phe Lys Phe Ser Asp
    690             695             700

Thr Ala Thr Tyr Glu Asn Val Ser Ser Phe Tyr Arg Glu Val Glu Asp
705             710             715             720

Gln Gly Tyr Lys Leu Ser Phe Arg Lys Val Ser Glu Ser Tyr Val Tyr
            725             730             735

Ser Leu Ile Asp Gln Gly Lys Leu Tyr Leu Phe Gln Ile Tyr Asn Lys
        740             745             750

Asp Phe Ser Pro Cys Ser Lys Gly Thr Pro Asn Leu His Thr Leu Tyr
        755             760             765

Trp Arg Met Leu Phe Asp Glu Arg Asn Leu Ala Asp Val Ile Tyr Lys
    770             775             780

Leu Asp Gly Lys Ala Glu Ile Phe Phe Arg Glu Lys Ser Leu Lys Asn
785             790             795             800

Asp His Pro Thr His Pro Ala Gly Lys Pro Ile Lys Lys Lys Ser Arg
            805             810             815

Gln Lys Lys Gly Glu Glu Ser Leu Phe Glu Tyr Asp Leu Val Lys Asp
        820             825             830

Arg Arg Tyr Thr Met Asp Lys Phe Gln Phe His Val Pro Ile Thr Met
        835             840             845

Asn Phe Lys Cys Ser Ala Gly Ser Lys Val Asn Asp Met Val Asn Ala
    850             855             860

His Ile Arg Glu Ala Lys Asp Met His Val Ile Gly Ile Asp Arg Gly
```

```
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
                900                 905                 910

Leu Leu Glu Ser Arg Asp Lys Asp Arg Gln Gln Glu His Arg Asn Trp
                915                 920                 925

Gln Thr Ile Glu Gly Ile Lys Glu Leu Lys Gln Gly Tyr Leu Ser Gln
        930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
                980                 985                 990

Asn Tyr Leu Val Asp Lys Lys Lys  Arg Pro Glu Asp Ile  Gly Gly Leu
                995                 1000                1005

Leu Arg  Ala Tyr Gln Phe Thr  Ala Pro Phe Lys Ser  Phe Lys Glu
        1010                1015                1020

Met Gly  Lys Gln Asn Gly Phe  Leu Phe Tyr Ile Pro  Ala Trp Asn
        1025                1030                1035

Thr Ser  Asn Ile Asp Pro Thr  Thr Gly Phe Val Asn  Leu Phe His
        1040                1045                1050

Val Gln  Tyr Glu Asn Val Asp  Lys Ala Lys Ser Phe  Phe Gln Lys
        1055                1060                1065

Phe Asp  Ser Ile Ser Tyr Asn  Pro Lys Lys Asp Trp  Phe Glu Phe
        1070                1075                1080

Ala Phe  Asp Tyr Lys Asn Phe  Thr Lys Lys Ala Glu  Gly Ser Arg
        1085                1090                1095

Ser Met  Trp Ile Leu Cys Thr  His Gly Ser Arg Ile  Lys Asn Phe
        1100                1105                1110

Arg Asn  Ser Gln Lys Asn Gly  Gln Trp Asp Ser Glu  Glu Phe Ala
        1115                1120                1125

Leu Thr  Glu Ala Phe Lys Ser  Leu Phe Val Arg Tyr  Glu Ile Asp
        1130                1135                1140

Tyr Thr  Ala Asp Leu Lys Thr  Ala Ile Val Asp Glu  Lys Gln Lys
        1145                1150                1155

Asp Phe  Phe Val Asp Leu Leu  Lys Leu Phe Lys Leu  Thr Val Gln
        1160                1165                1170

Met Arg  Asn Ser Trp Lys Glu  Lys Asp Leu Asp Tyr  Leu Ile Ser
        1175                1180                1185

Pro Val  Ala Gly Ala Asp Gly  Arg Phe Phe Asp Thr  Arg Glu Gly
        1190                1195                1200

Asn Lys  Ser Leu Pro Lys Asp  Ala Asp Ala Asn Gly  Ala Tyr Asn
        1205                1210                1215

Ile Ala  Leu Lys Gly Leu Trp  Ala Leu Arg Gln Ile  Arg Gln Thr
        1220                1225                1230

Ser Glu  Gly Gly Lys Leu Lys  Leu Ala Ile Ser Asn  Lys Glu Trp
        1235                1240                1245

Leu Gln  Phe Val Gln Glu Arg  Ser Tyr Glu Lys Asp
        1250                1255                1260
```

<210> SEQ ID NO 27

```
<211> LENGTH: 1300
<212> TYPE: PRT
<213> ORGANISM: Francisella tularensis

<400> SEQUENCE: 27

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
```

-continued 385                390                395                400

Asp Leu Ser Gln Gln Val Phe Asp Asp Tyr Ser Val Ile Gly Thr Ala
            405                410                415

Val Leu Glu Tyr Ile Thr Gln Gln Ile Ala Pro Lys Asn Leu Asp Asn
            420                425                430

Pro Ser Lys Lys Glu Gln Glu Leu Ile Ala Lys Lys Thr Glu Lys Ala
            435                440                445

Lys Tyr Leu Ser Leu Glu Thr Ile Lys Leu Ala Leu Glu Glu Phe Asn
            450                455                460

Lys His Arg Asp Ile Asp Lys Gln Cys Arg Phe Glu Glu Ile Leu Ala
465                470                475                480

Asn Phe Ala Ala Ile Pro Met Ile Phe Asp Glu Ile Ala Gln Asn Lys
            485                490                495

Asp Asn Leu Ala Gln Ile Ser Ile Lys Tyr Gln Asn Gln Gly Lys Lys
            500                505                510

Asp Leu Leu Gln Ala Ser Ala Glu Asp Asp Val Lys Ala Ile Lys Asp
            515                520                525

Leu Leu Asp Gln Thr Asn Asn Leu Leu His Lys Leu Lys Ile Phe His
            530                535                540

Ile Ser Gln Ser Glu Asp Lys Ala Asn Ile Leu Asp Lys Asp Glu His
545                550                555                560

Phe Tyr Leu Val Phe Glu Glu Cys Tyr Phe Glu Leu Ala Asn Ile Val
            565                570                575

Pro Leu Tyr Asn Lys Ile Arg Asn Tyr Ile Thr Gln Lys Pro Tyr Ser
            580                585                590

Asp Glu Lys Phe Lys Leu Asn Phe Glu Asn Ser Thr Leu Ala Asn Gly
            595                600                605

Trp Asp Lys Asn Lys Glu Pro Asp Asn Thr Ala Ile Leu Phe Ile Lys
            610                615                620

Asp Asp Lys Tyr Tyr Leu Gly Val Met Asn Lys Lys Asn Asn Lys Ile
625                630                635                640

Phe Asp Asp Lys Ala Ile Lys Glu Asn Lys Gly Glu Gly Tyr Lys Lys
            645                650                655

Ile Val Tyr Lys Leu Leu Pro Gly Ala Asn Lys Met Leu Pro Lys Val
            660                665                670

Phe Phe Ser Ala Lys Ser Ile Lys Phe Tyr Asn Pro Ser Glu Asp Ile
            675                680                685

Leu Arg Ile Arg Asn His Ser Thr His Thr Lys Asn Gly Ser Pro Gln
            690                695                700

Lys Gly Tyr Glu Lys Phe Glu Phe Asn Ile Glu Asp Cys Arg Lys Phe
705                710                715                720

Ile Asp Phe Tyr Lys Gln Ser Ile Ser Lys His Pro Glu Trp Lys Asp
            725                730                735

Phe Gly Phe Arg Phe Ser Asp Thr Gln Arg Tyr Asn Ser Ile Asp Glu
            740                745                750

Phe Tyr Arg Glu Val Glu Asn Gln Gly Tyr Lys Leu Thr Phe Glu Asn
            755                760                765

Ile Ser Glu Ser Tyr Ile Asp Ser Val Val Asn Gln Gly Lys Leu Tyr
            770                775                780

Leu Phe Gln Ile Tyr Asn Lys Asp Phe Ser Ala Tyr Ser Lys Gly Arg
785                790                795                800

Pro Asn Leu His Thr Leu Tyr Trp Lys Ala Leu Phe Asp Glu Arg Asn
            805                810                815

```
Leu Gln Asp Val Val Tyr Lys Leu Asn Gly Glu Ala Glu Leu Phe Tyr
        820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
        850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
        900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
        930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
1010                1015                1020

Tyr Gln  Lys Leu Glu Lys Met  Leu Ile Glu Lys Leu  Asn Tyr Leu
1025                1030                1035

Val Phe  Lys Asp Asn Glu Phe  Asp Lys Thr Gly Gly  Val Leu Arg
1040                1045                1050

Ala Tyr  Gln Leu Thr Ala Pro  Phe Glu Thr Phe Lys  Lys Met Gly
1055                1060                1065

Lys Gln  Thr Gly Ile Ile Tyr  Tyr Val Pro Ala Gly  Phe Thr Ser
1070                1075                1080

Lys Ile  Cys Pro Val Thr Gly  Phe Val Asn Gln Leu  Tyr Pro Lys
1085                1090                1095

Tyr Glu  Ser Val Ser Lys Ser  Gln Glu Phe Phe Ser  Lys Phe Asp
1100                1105                1110

Lys Ile  Cys Tyr Asn Leu Asp  Lys Gly Tyr Phe Glu  Phe Ser Phe
1115                1120                1125

Asp Tyr  Lys Asn Phe Gly Asp  Lys Ala Ala Lys Gly  Lys Trp Thr
1130                1135                1140

Ile Ala  Ser Phe Gly Ser Arg  Leu Ile Asn Phe Arg  Asn Ser Asp
1145                1150                1155

Lys Asn  His Asn Trp Asp Thr  Arg Glu Val Tyr Pro  Thr Lys Glu
1160                1165                1170

Leu Glu  Lys Leu Leu Lys Asp  Tyr Ser Ile Glu Tyr  Gly His Gly
1175                1180                1185

Glu Cys  Ile Lys Ala Ala Ile  Cys Gly Glu Ser Asp  Lys Lys Phe
1190                1195                1200

Phe Ala  Lys Leu Thr Ser Val  Leu Asn Thr Ile Leu  Gln Met Arg
1205                1210                1215
```

-continued

```
Asn Ser  Lys Thr Gly Thr Glu  Leu Asp Tyr Leu Ile  Ser Pro Val
    1220                1225            1230

Ala Asp  Val Asn Gly Asn Phe  Phe Asp Ser Arg Gln  Ala Pro Lys
    1235                1240            1245

Asn Met  Pro Gln Asp Ala Asp  Ala Asn Gly Ala Tyr  His Ile Gly
    1250                1255            1260

Leu Lys  Gly Leu Met Leu Leu  Gly Arg Ile Lys Asn  Asn Gln Glu
    1265                1270            1275

Gly Lys  Lys Leu Asn Leu Val  Ile Lys Asn Glu Glu  Tyr Phe Glu
    1280                1285            1290

Phe Val  Gln Asn Arg Asn Asn
    1295                1300

<210> SEQ ID NO 28
<211> LENGTH: 1307
<212> TYPE: PRT
<213> ORGANISM: Acidaminococcus

<400> SEQUENCE: 28

Met Thr Gln Phe Glu Gly Phe Thr Asn Leu Tyr Gln Val Ser Lys Thr
1                5                  10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
    275                 280                 285
```

```
Asp Glu Thr Ala His Ile Ile Ala Ser Leu Pro His Arg Phe Ile Pro
    290             295             300

Leu Phe Lys Gln Ile Leu Ser Asp Arg Asn Thr Leu Ser Phe Ile Leu
305             310             315             320

Glu Glu Phe Lys Ser Asp Glu Glu Val Ile Gln Ser Phe Cys Lys Tyr
            325             330             335

Lys Thr Leu Leu Arg Asn Glu Asn Val Leu Glu Thr Ala Glu Ala Leu
            340             345             350

Phe Asn Glu Leu Asn Ser Ile Asp Leu Thr His Ile Phe Ile Ser His
            355             360             365

Lys Lys Leu Glu Thr Ile Ser Ser Ala Leu Cys Asp His Trp Asp Thr
    370             375             380

Leu Arg Asn Ala Leu Tyr Glu Arg Arg Ile Ser Glu Leu Thr Gly Lys
385             390             395             400

Ile Thr Lys Ser Ala Lys Glu Lys Val Gln Arg Ser Leu Lys His Glu
            405             410             415

Asp Ile Asn Leu Gln Glu Ile Ile Ser Ala Ala Gly Lys Glu Leu Ser
            420             425             430

Glu Ala Phe Lys Gln Lys Thr Ser Glu Ile Leu Ser His Ala His Ala
            435             440             445

Ala Leu Asp Gln Pro Leu Pro Thr Thr Leu Lys Lys Gln Glu Glu Lys
    450             455             460

Glu Ile Leu Lys Ser Gln Leu Asp Ser Leu Leu Gly Leu Tyr His Leu
465             470             475             480

Leu Asp Trp Phe Ala Val Asp Glu Ser Asn Glu Val Asp Pro Glu Phe
            485             490             495

Ser Ala Arg Leu Thr Gly Ile Lys Leu Glu Met Glu Pro Ser Leu Ser
            500             505             510

Phe Tyr Asn Lys Ala Arg Asn Tyr Ala Thr Lys Lys Pro Tyr Ser Val
            515             520             525

Glu Lys Phe Lys Leu Asn Phe Gln Met Pro Thr Leu Ala Ser Gly Trp
    530             535             540

Asp Val Asn Lys Glu Lys Asn Asn Gly Ala Ile Leu Phe Val Lys Asn
545             550             555             560

Gly Leu Tyr Tyr Leu Gly Ile Met Pro Lys Gln Lys Gly Arg Tyr Lys
            565             570             575

Ala Leu Ser Phe Glu Pro Thr Glu Lys Thr Ser Glu Gly Phe Asp Lys
            580             585             590

Met Tyr Tyr Asp Tyr Phe Pro Asp Ala Ala Lys Met Ile Pro Lys Cys
            595             600             605

Ser Thr Gln Leu Lys Ala Val Thr Ala His Phe Gln Thr His Thr Thr
    610             615             620

Pro Ile Leu Leu Ser Asn Asn Phe Ile Glu Pro Leu Glu Ile Thr Lys
625             630             635             640

Glu Ile Tyr Asp Leu Asn Asn Pro Glu Lys Glu Pro Lys Lys Phe Gln
            645             650             655

Thr Ala Tyr Ala Lys Lys Thr Gly Asp Gln Lys Gly Tyr Arg Glu Ala
            660             665             670

Leu Cys Lys Trp Ile Asp Phe Thr Arg Asp Phe Leu Ser Lys Tyr Thr
    675             680             685

Lys Thr Thr Ser Ile Asp Leu Ser Ser Leu Arg Pro Ser Ser Gln Tyr
    690             695             700
```

```
Lys Asp Leu Gly Glu Tyr Tyr Ala Glu Leu Asn Pro Leu Leu Tyr His
705             710             715             720

Ile Ser Phe Gln Arg Ile Ala Glu Lys Glu Ile Met Asp Ala Val Glu
                725             730             735

Thr Gly Lys Leu Tyr Leu Phe Gln Ile Tyr Asn Lys Asp Phe Ala Lys
            740             745             750

Gly His His Gly Lys Pro Asn Leu His Thr Leu Tyr Trp Thr Gly Leu
        755             760             765

Phe Ser Pro Glu Asn Leu Ala Lys Thr Ser Ile Lys Leu Asn Gly Gln
    770             775             780

Ala Glu Leu Phe Tyr Arg Pro Lys Ser Arg Met Lys Arg Met Ala His
785             790             795             800

Arg Leu Gly Glu Lys Met Leu Asn Lys Lys Leu Lys Asp Gln Lys Thr
            805             810             815

Pro Ile Pro Asp Thr Leu Tyr Gln Glu Leu Tyr Asp Tyr Val Asn His
            820             825             830

Arg Leu Ser His Asp Leu Ser Asp Glu Ala Arg Ala Leu Leu Pro Asn
        835             840             845

Val Ile Thr Lys Glu Val Ser His Glu Ile Ile Lys Asp Arg Arg Phe
    850             855             860

Thr Ser Asp Lys Phe Phe Phe His Val Pro Ile Thr Leu Asn Tyr Gln
865             870             875             880

Ala Ala Asn Ser Pro Ser Lys Phe Asn Gln Arg Val Asn Ala Tyr Leu
                885             890             895

Lys Glu His Pro Glu Thr Pro Ile Ile Gly Ile Asp Arg Gly Glu Arg
            900             905             910

Asn Leu Ile Tyr Ile Thr Val Ile Asp Ser Thr Gly Lys Ile Leu Glu
        915             920             925

Gln Arg Ser Leu Asn Thr Ile Gln Gln Phe Asp Tyr Gln Lys Lys Leu
    930             935             940

Asp Asn Arg Glu Lys Glu Arg Val Ala Ala Arg Gln Ala Trp Ser Val
945             950             955             960

Val Gly Thr Ile Lys Asp Leu Lys Gln Gly Tyr Leu Ser Gln Val Ile
            965             970             975

His Glu Ile Val Asp Leu Met Ile His Tyr Gln Ala Val Val Val Leu
        980             985             990

Glu Asn Leu Asn Phe Gly Phe Lys  Ser Lys Arg Thr Gly  Ile Ala Glu
        995             1000             1005

Lys Ala  Val Tyr Gln Gln Phe  Glu Lys Met Leu Ile  Asp Lys Leu
    1010             1015             1020

Asn Cys  Leu Val Leu Lys Asp  Tyr Pro Ala Glu Lys  Val Gly Gly
    1025             1030             1035

Val Leu  Asn Pro Tyr Gln Leu  Thr Asp Gln Phe Thr  Ser Phe Ala
    1040             1045             1050

Lys Met  Gly Thr Gln Ser Gly  Phe Leu Phe Tyr Val  Pro Ala Pro
    1055             1060             1065

Tyr Thr  Ser Lys Ile Asp Pro  Leu Thr Gly Phe Val  Asp Pro Phe
    1070             1075             1080

Val Trp  Lys Thr Ile Lys Asn  His Glu Ser Arg Lys  His Phe Leu
    1085             1090             1095

Glu Gly  Phe Asp Phe Leu His  Tyr Asp Val Lys Thr  Gly Asp Phe
    1100             1105             1110

Ile Leu  His Phe Lys Met Asn  Arg Asn Leu Ser Phe  Gln Arg Gly
```

-continued

```
              1115                1120                1125

Leu Pro  Gly Phe Met Pro Ala  Trp Asp Ile Val Phe  Glu Lys Asn
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290

Ser Asn  Gln Asp Trp Leu Ala  Tyr Ile Gln Glu Leu  Arg Asn
    1295                1300                1305

<210> SEQ ID NO 29
<211> LENGTH: 1323
<212> TYPE: PRT
<213> ORGANISM: Prevotella disiens

<400> SEQUENCE: 29

Met Glu Asn Tyr Gln Glu Phe Thr Asn Leu Phe Gln Leu Asn Lys Thr
1               5                   10                  15

Leu Arg Phe Glu Leu Lys Pro Ile Gly Lys Thr Cys Glu Leu Leu Glu
            20                  25                  30

Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Glu Val Lys Lys Thr Ala Leu Arg
            100                 105                 110

Asn Lys Cys Thr Ser Ile Gln Arg Ala Met Arg Glu Ala Ile Ser Gln
        115                 120                 125

Ala Phe Leu Lys Ser Pro Gln Lys Lys Leu Leu Ala Ile Lys Asn Leu
    130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175
```

```
Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
            195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
    275                 280                 285

Phe Phe Ile Ser Leu Lys Lys Gln Ile Leu Ser Asp Arg Glu Ala Leu
    290                 295                 300

Ser Trp Leu Pro Asp Met Phe Lys Asn Asp Ser Glu Val Ile Lys Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
            355                 360                 365

Tyr Arg Asn Phe Ser Ile Asp Glu Ala Ile Asp Ala Asn Ala Glu Leu
    370                 375                 380

Gln Thr Phe Asn Asn Tyr Glu Leu Ile Ala Asn Ala Leu Arg Ala Lys
385                 390                 395                 400

Ile Lys Lys Glu Thr Lys Gln Gly Arg Lys Ser Phe Glu Lys Tyr Glu
                405                 410                 415

Glu Tyr Ile Asp Lys Lys Val Lys Ala Ile Asp Ser Leu Ser Ile Gln
            420                 425                 430

Glu Ile Asn Glu Leu Val Glu Asn Tyr Val Ser Glu Phe Asn Ser Asn
            435                 440                 445

Ser Gly Asn Met Pro Arg Lys Val Glu Asp Tyr Phe Ser Leu Met Arg
    450                 455                 460

Lys Gly Asp Phe Gly Ser Asn Asp Leu Ile Glu Asn Ile Lys Thr Lys
465                 470                 475                 480

Leu Ser Ala Ala Glu Lys Leu Leu Gly Thr Lys Tyr Gln Glu Thr Ala
                485                 490                 495

Lys Asp Ile Phe Lys Lys Asp Glu Asn Ser Lys Leu Ile Lys Glu Leu
            500                 505                 510

Leu Asp Ala Thr Lys Gln Phe Gln His Phe Ile Lys Pro Leu Leu Gly
            515                 520                 525

Thr Gly Glu Glu Ala Asp Arg Asp Leu Val Phe Tyr Gly Asp Phe Leu
    530                 535                 540

Pro Leu Tyr Glu Lys Phe Glu Glu Leu Thr Leu Leu Tyr Asn Lys Val
545                 550                 555                 560

Arg Asn Arg Leu Thr Gln Lys Pro Tyr Ser Lys Asp Lys Ile Arg Leu
                565                 570                 575

Cys Phe Asn Lys Pro Lys Leu Met Thr Gly Trp Val Asp Ser Lys Thr
            580                 585                 590

Glu Lys Ser Asp Asn Gly Thr Gln Tyr Gly Gly Tyr Leu Phe Arg Lys
```

-continued

```
             595                 600                 605
Lys Asn Glu Ile Gly Glu Tyr Asp Tyr Phe Leu Gly Ile Ser Ser Lys
         610                 615                 620

Ala Gln Leu Phe Arg Lys Asn Glu Ala Val Ile Gly Asp Tyr Glu Arg
625                 630                 635                 640

Leu Asp Tyr Tyr Gln Pro Lys Ala Asn Thr Ile Tyr Gly Ser Ala Tyr
             645                 650                 655

Glu Gly Glu Asn Ser Tyr Lys Glu Asp Lys Lys Arg Leu Asn Lys Val
         660                 665                 670

Ile Ile Ala Tyr Ile Glu Gln Ile Lys Gln Thr Asn Ile Lys Lys Ser
         675                 680                 685

Ile Ile Glu Ser Ile Ser Lys Tyr Pro Asn Ile Ser Asp Asp Asp Lys
         690                 695                 700

Val Thr Pro Ser Ser Leu Leu Glu Lys Ile Lys Lys Val Ser Ile Asp
705                 710                 715                 720

Ser Tyr Asn Gly Ile Leu Ser Phe Lys Ser Phe Gln Ser Val Asn Lys
             725                 730                 735

Glu Val Ile Asp Asn Leu Leu Lys Thr Ile Ser Pro Leu Lys Asn Lys
             740                 745                 750

Ala Glu Phe Leu Asp Leu Ile Asn Lys Asp Tyr Gln Ile Phe Thr Glu
             755                 760                 765

Val Gln Ala Val Ile Asp Glu Ile Cys Lys Gln Lys Thr Phe Ile Tyr
             770                 775                 780

Phe Pro Ile Ser Asn Val Glu Leu Glu Lys Glu Met Gly Asp Lys Asp
785                 790                 795                 800

Lys Pro Leu Cys Leu Phe Gln Ile Ser Asn Lys Asp Leu Ser Phe Ala
             805                 810                 815

Lys Thr Phe Ser Ala Asn Leu Arg Lys Lys Arg Gly Ala Glu Asn Leu
             820                 825                 830

His Thr Met Leu Phe Lys Ala Leu Met Glu Gly Asn Gln Asp Asn Leu
             835                 840                 845

Asp Leu Gly Ser Gly Ala Ile Phe Tyr Arg Ala Lys Ser Leu Asp Gly
         850                 855                 860

Asn Lys Pro Thr His Pro Ala Asn Glu Ala Ile Lys Cys Arg Asn Val
865                 870                 875                 880

Ala Asn Lys Asp Lys Val Ser Leu Phe Thr Tyr Asp Ile Tyr Lys Asn
             885                 890                 895

Arg Arg Tyr Met Glu Asn Lys Phe Leu Phe His Leu Ser Ile Val Gln
             900                 905                 910

Asn Tyr Lys Ala Ala Asn Asp Ser Ala Gln Leu Asn Ser Ser Ala Thr
         915                 920                 925

Glu Tyr Ile Arg Lys Ala Asp Asp Leu His Ile Ile Gly Ile Asp Arg
         930                 935                 940

Gly Glu Arg Asn Leu Leu Tyr Tyr Ser Val Ile Asp Met Lys Gly Asn
945                 950                 955                 960

Ile Val Glu Gln Asp Ser Leu Asn Ile Ile Arg Asn Asn Asp Leu Glu
             965                 970                 975

Thr Asp Tyr His Asp Leu Leu Asp Lys Arg Glu Lys Glu Arg Lys Ala
             980                 985                 990

Asn Arg Gln Asn Trp Glu Ala Val  Glu Gly Ile Lys Asp  Leu Lys Lys
         995                 1000                 1005

Gly Tyr  Leu Ser Gln Ala Val  His Gln Ile Ala Gln  Leu Met Leu
     1010                 1015                 1020
```

```
Lys Tyr  Asn Ala Ile Ile Ala  Leu Glu Asp Leu Gly  Gln Met Phe
    1025             1030              1035

Val Thr  Arg Gly Gln Lys Ile  Glu Lys Ala Val Tyr  Gln Gln Phe
    1040             1045              1050

Glu Lys  Ser Leu Val Asp Lys  Leu Ser Tyr Leu Val  Asp Lys Lys
    1055             1060              1065

Arg Pro  Tyr Asn Glu Leu Gly  Gly Ile Leu Lys Ala  Tyr Gln Leu
    1070             1075              1080

Ala Ser  Ser Ile Thr Lys Asn  Asn Ser Asp Lys Gln  Asn Gly Phe
    1085             1090              1095

Leu Phe  Tyr Val Pro Ala Trp  Asn Thr Ser Lys Ile  Asp Pro Val
    1100             1105              1110

Thr Gly  Phe Thr Asp Leu Leu  Arg Pro Lys Ala Met  Thr Ile Lys
    1115             1120              1125

Glu Ala  Gln Asp Phe Phe Gly  Ala Phe Asp Asn Ile  Ser Tyr Asn
    1130             1135              1140

Asp Lys  Gly Tyr Phe Glu Phe  Glu Thr Asn Tyr Asp  Lys Phe Lys
    1145             1150              1155

Ile Arg  Met Lys Ser Ala Gln  Thr Arg Trp Thr Ile  Cys Thr Phe
    1160             1165              1170

Gly Asn  Arg Ile Lys Arg Lys  Lys Asp Lys Asn Tyr  Trp Asn Tyr
    1175             1180              1185

Glu Glu  Val Glu Leu Thr Glu  Glu Phe Lys Lys Leu  Phe Lys Asp
    1190             1195              1200

Ser Asn  Ile Asp Tyr Glu Asn  Cys Asn Leu Lys Glu  Glu Ile Gln
    1205             1210              1215

Asn Lys  Asp Asn Arg Lys Phe  Phe Asp Asp Leu Ile  Lys Leu Leu
    1220             1225              1230

Gln Leu  Thr Leu Gln Met Arg  Asn Ser Asp Asp Lys  Gly Asn Asp
    1235             1240              1245

Tyr Ile  Ile Ser Pro Val Ala  Asn Ala Glu Gly Gln  Phe Phe Asp
    1250             1255              1260

Ser Arg  Asn Gly Asp Lys Lys  Leu Pro Leu Asp Ala  Asp Ala Asn
    1265             1270              1275

Gly Ala  Tyr Asn Ile Ala Arg  Lys Gly Leu Trp Asn  Ile Arg Gln
    1280             1285              1290

Ile Lys  Gln Thr Lys Asn Asp  Lys Lys Leu Asn Leu  Ser Ile Ser
    1295             1300              1305

Ser Thr  Glu Trp Leu Asp Phe  Val Arg Glu Lys Pro  Tyr Leu Lys
    1310             1315              1320
```

```
<210> SEQ ID NO 30
<211> LENGTH: 1373
<212> TYPE: PRT
<213> ORGANISM: Moraxella bovoculi

<400> SEQUENCE: 30

Met Leu Phe Gln Asp Phe Thr His Leu Tyr Pro Leu Ser Lys Thr Val
1               5               10              15

Arg Phe Glu Leu Lys Pro Ile Asp Arg Thr Leu Glu His Ile His Ala
            20              25              30

Lys Asn Phe Leu Ser Gln Asp Glu Thr Met Ala Asp Met His Gln Lys
        35              40              45

Val Lys Val Ile Leu Asp Asp Tyr His Arg Asp Phe Ile Ala Asp Met
```

```
            50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Glu Leu Gln Lys Gln Leu
                85                  90                  95

Lys Asp Leu Gln Ala Val Leu Arg Lys Glu Ile Val Lys Pro Ile Gly
                100                 105                 110

Asn Gly Gly Lys Tyr Lys Ala Gly Tyr Asp Arg Leu Phe Gly Ala Lys
                115                 120                 125

Leu Phe Lys Asp Gly Lys Glu Leu Gly Asp Leu Ala Lys Phe Val Ile
                130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
                180                 185                 190

His Glu Asn Leu Pro Arg Phe Ile Asp Asn Leu Gln Ile Leu Thr Thr
                195                 200                 205

Ile Lys Gln Lys His Ser Ala Leu Tyr Asp Gln Ile Ile Asn Glu Leu
                210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
                260                 265                 270

Glu Leu Ile Asn Ser His His Asn Gln His Cys His Lys Ser Glu Arg
                275                 280                 285

Ile Ala Lys Leu Arg Pro Leu His Lys Gln Ile Leu Ser Asp Gly Met
                290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
                340                 345                 350

Tyr Val Glu His Lys Asn Leu Asn Glu Leu Ser Lys Gln Ala Phe Gly
                355                 360                 365

Asp Phe Ala Leu Leu Gly Arg Val Leu Asp Gly Tyr Tyr Val Asp Val
                370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
                420                 425                 430

His Asp Asp Glu Ser Val Gln Ala Gly Lys Leu Gly Gln Tyr Phe Lys
                435                 440                 445

His Gly Leu Ala Gly Val Asp Asn Pro Ile Gln Lys Ile His Asn Asn
                450                 455                 460

His Ser Thr Ile Lys Gly Phe Leu Glu Arg Glu Arg Pro Ala Gly Glu
465                 470                 475                 480
```

```
Arg Ala Leu Pro Lys Ile Lys Ser Gly Lys Asn Pro Glu Met Thr Gln
            485             490             495

Leu Arg Gln Leu Lys Glu Leu Leu Asp Asn Ala Leu Asn Val Ala His
        500             505             510

Phe Ala Lys Leu Leu Thr Thr Lys Thr Thr Leu Asp Asn Gln Asp Gly
        515             520             525

Asn Phe Tyr Gly Glu Phe Gly Val Leu Tyr Asp Glu Leu Ala Lys Ile
    530             535             540

Pro Thr Leu Tyr Asn Lys Val Arg Asp Tyr Leu Ser Gln Lys Pro Phe
545             550             555             560

Ser Thr Glu Lys Tyr Lys Leu Asn Phe Gly Asn Pro Thr Leu Leu Asn
            565             570             575

Gly Trp Asp Leu Asn Lys Glu Lys Asp Asn Phe Gly Val Ile Leu Gln
        580             585             590

Lys Asp Gly Cys Tyr Tyr Leu Ala Leu Leu Asp Lys Ala His Lys Lys
        595             600             605

Val Phe Asp Asn Ala Pro Asn Thr Gly Lys Ser Ile Tyr Gln Lys Met
        610             615             620

Ile Tyr Lys Tyr Leu Glu Val Arg Lys Gln Phe Pro Lys Val Phe Phe
625             630             635             640

Ser Lys Glu Ala Ile Ala Ile Asn Tyr His Pro Ser Lys Glu Leu Val
            645             650             655

Glu Ile Lys Asp Lys Gly Arg Gln Arg Ser Asp Asp Glu Arg Leu Lys
            660             665             670

Leu Tyr Arg Phe Ile Leu Glu Cys Leu Lys Ile His Pro Lys Tyr Asp
        675             680             685

Lys Lys Phe Glu Gly Ala Ile Gly Asp Ile Gln Leu Phe Lys Lys Asp
        690             695             700

Lys Lys Gly Arg Glu Val Pro Ile Ser Glu Lys Asp Leu Phe Asp Lys
705             710             715             720

Ile Asn Gly Ile Phe Ser Ser Lys Pro Lys Leu Glu Met Glu Asp Phe
            725             730             735

Phe Ile Gly Glu Phe Lys Arg Tyr Asn Pro Ser Gln Asp Leu Val Asp
        740             745             750

Gln Tyr Asn Ile Tyr Lys Lys Ile Asp Ser Asn Asp Asn Arg Lys Lys
        755             760             765

Glu Asn Phe Tyr Asn Asn His Pro Lys Phe Lys Lys Asp Leu Val Arg
        770             775             780

Tyr Tyr Tyr Glu Ser Met Cys Lys His Glu Glu Trp Glu Glu Ser Phe
785             790             795             800

Glu Phe Ser Lys Lys Leu Gln Asp Ile Gly Cys Tyr Val Asp Val Asn
            805             810             815

Glu Leu Phe Thr Glu Ile Glu Thr Arg Arg Leu Asn Tyr Lys Ile Ser
        820             825             830

Phe Cys Asn Ile Asn Ala Asp Tyr Ile Asp Glu Leu Val Glu Gln Gly
        835             840             845

Gln Leu Tyr Leu Phe Gln Ile Tyr Asn Lys Asp Phe Ser Pro Lys Ala
    850             855             860

His Gly Lys Pro Asn Leu His Thr Leu Tyr Phe Lys Ala Leu Phe Ser
865             870             875             880

Glu Asp Asn Leu Ala Asp Pro Ile Tyr Lys Leu Asn Gly Glu Ala Gln
            885             890             895
```

-continued

```
Ile Phe Tyr Arg Lys Ala Ser Leu Asp Met Asn Glu Thr Thr Ile His
            900                 905                 910

Arg Ala Gly Glu Val Leu Glu Asn Lys Asn Pro Asp Asn Pro Lys Lys
        915                 920                 925

Arg Gln Phe Val Tyr Asp Ile Ile Lys Asp Lys Arg Tyr Thr Gln Asp
        930                 935                 940

Lys Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
                980                 985                 990

Leu Tyr Leu Thr Val Ile Asn Ser  Lys Gly Glu Ile Leu  Glu Gln Cys
        995                 1000                1005

Ser Leu  Asn Asp Ile Thr Thr  Ala Ser Ala Asn Gly  Thr Gln Met
    1010                1015                1020

Thr Thr  Pro Tyr His Lys Ile  Leu Asp Lys Arg Glu  Ile Glu Arg
    1025                1030                1035

Leu Asn  Ala Arg Val Gly Trp  Gly Glu Ile Glu Thr  Ile Lys Glu
    1040                1045                1050

Leu Lys  Ser Gly Tyr Leu Ser  His Val Val His Gln  Ile Ser Gln
    1055                1060                1065

Leu Met  Leu Lys Tyr Asn Ala  Ile Val Val Leu Glu  Asp Leu Asn
    1070                1075                1080

Phe Gly  Phe Lys Arg Gly Arg  Phe Lys Val Glu Lys  Gln Ile Tyr
    1085                1090                1095

Gln Asn  Phe Glu Asn Ala Leu  Ile Lys Lys Leu Asn  His Leu Val
    1100                1105                1110

Leu Lys  Asp Lys Ala Asp Asp  Glu Ile Gly Ser Tyr  Lys Asn Ala
    1115                1120                1125

Leu Gln  Leu Thr Asn Asn Phe  Thr Asp Leu Lys Ser  Ile Gly Lys
    1130                1135                1140

Gln Thr  Gly Phe Leu Phe Tyr  Val Pro Ala Trp Asn  Thr Ser Lys
    1145                1150                1155

Ile Asp  Pro Glu Thr Gly Phe  Val Asp Leu Leu Lys  Pro Arg Tyr
    1160                1165                1170

Glu Asn  Ile Ala Gln Ser Gln  Ala Phe Phe Gly Lys  Phe Asp Lys
    1175                1180                1185

Ile Cys  Tyr Asn Ala Asp Lys  Asp Tyr Phe Glu Phe  His Ile Asp
    1190                1195                1200

Tyr Ala  Lys Phe Thr Asp Lys  Ala Lys Asn Ser Arg  Gln Ile Trp
    1205                1210                1215

Thr Ile  Cys Ser His Gly Asp  Lys Arg Tyr Val Tyr  Asp Lys Thr
    1220                1225                1230

Ala Asn  Gln Asn Lys Gly Ala  Ala Lys Gly Ile Asn  Val Asn Asp
    1235                1240                1245

Glu Leu  Lys Ser Leu Phe Ala  Arg His His Ile Asn  Glu Lys Gln
    1250                1255                1260

Pro Asn  Leu Val Met Asp Ile  Cys Gln Asn Asn Asp  Lys Glu Phe
    1265                1270                1275

His Lys  Ser Leu Met Tyr Leu  Leu Lys Thr Leu Leu  Ala Leu Arg
    1280                1285                1290

Tyr Ser  Asn Ala Ser Ser Asp  Glu Asp Phe Ile Leu  Ser Pro Val
```

-continued

```
              1295              1300              1305

Ala Asn  Asp Glu Gly Val Phe  Phe Asn Ser Ala Leu  Ala Asp Asp
    1310              1315              1320

Thr Gln  Pro Gln Asn Ala Asp  Ala Asn Gly Ala Tyr  His Ile Ala
    1325              1330              1335

Leu Lys  Gly Leu Trp Leu Leu  Asn Glu Leu Lys Asn  Ser Asp Asp
    1340              1345              1350

Leu Asn  Lys Val Lys Leu Ala  Ile Asp Asn Gln Thr  Trp Leu Asn
    1355              1360              1365

Phe Ala  Gln Asn Arg
    1370

<210> SEQ ID NO 31
<211> LENGTH: 1263
<212> TYPE: PRT
<213> ORGANISM: Leptospira inadai

<400> SEQUENCE: 31

Met Glu Asp Tyr Ser Gly Phe Val Asn Ile Tyr Ser Ile Gln Lys Thr
1               5               10              15

Leu Arg Phe Glu Leu Lys Pro Val Gly Lys Thr Leu Glu His Ile Glu
            20              25              30

Lys Lys Gly Phe Leu Lys Lys Asp Lys Ile Arg Ala Glu Asp Tyr Lys
        35              40              45

Ala Val Lys Lys Ile Ile Asp Lys Tyr His Arg Ala Tyr Ile Glu Glu
    50              55              60

Val Phe Asp Ser Val Leu His Gln Lys Lys Lys Asp Lys Thr Arg
65              70              75              80

Phe Ser Thr Gln Phe Ile Lys Glu Ile Lys Glu Phe Ser Glu Leu Tyr
                85              90              95

Tyr Lys Thr Glu Lys Asn Ile Pro Asp Lys Glu Arg Leu Glu Ala Leu
            100             105             110

Ser Glu Lys Leu Arg Lys Met Leu Val Gly Ala Phe Lys Gly Glu Phe
        115             120             125

Ser Glu Glu Val Ala Glu Lys Tyr Lys Asn Leu Phe Ser Lys Glu Leu
    130             135             140

Ile Arg Asn Glu Ile Glu Lys Phe Cys Glu Thr Asp Glu Glu Arg Lys
145             150             155             160

Gln Val Ser Asn Phe Lys Ser Phe Thr Thr Tyr Phe Thr Gly Phe His
            165             170             175

Ser Asn Arg Gln Asn Ile Tyr Ser Asp Glu Lys Lys Ser Thr Ala Ile
            180             185             190

Gly Tyr Arg Ile Ile His Gln Asn Leu Pro Lys Phe Leu Asp Asn Leu
            195             200             205

Lys Ile Ile Glu Ser Ile Gln Arg Arg Phe Lys Asp Phe Pro Trp Ser
    210             215             220

Asp Leu Lys Lys Asn Leu Lys Lys Ile Asp Lys Asn Ile Lys Leu Thr
225             230             235             240

Glu Tyr Phe Ser Ile Asp Gly Phe Val Asn Val Leu Asn Gln Lys Gly
            245             250             255

Ile Asp Ala Tyr Asn Thr Ile Leu Gly Gly Lys Ser Glu Glu Ser Gly
            260             265             270

Glu Lys Ile Gln Gly Leu Asn Glu Tyr Ile Asn Leu Tyr Arg Gln Lys
        275             280             285
```

-continued

```
Asn Asn Ile Asp Arg Lys Asn Leu Pro Asn Val Lys Ile Leu Phe Lys
    290             295             300

Gln Ile Leu Gly Asp Arg Glu Thr Lys Ser Phe Ile Pro Glu Ala Phe
305             310             315             320

Pro Asp Asp Gln Ser Val Leu Asn Ser Ile Thr Glu Phe Ala Lys Tyr
            325             330             335

Leu Lys Leu Asp Lys Lys Lys Ser Ile Ile Ala Glu Leu Lys Lys
            340             345             350

Phe Leu Ser Ser Phe Asn Arg Tyr Glu Leu Asp Gly Ile Tyr Leu Ala
        355             360             365

Asn Asp Asn Ser Leu Ala Ser Ile Ser Thr Phe Leu Phe Asp Asp Trp
    370             375             380

Ser Phe Ile Lys Lys Ser Val Ser Phe Lys Tyr Asp Glu Ser Val Gly
385             390             395             400

Asp Pro Lys Lys Lys Ile Lys Ser Pro Leu Lys Tyr Glu Lys Glu Lys
            405             410             415

Glu Lys Trp Leu Lys Gln Lys Tyr Tyr Thr Ile Ser Phe Leu Asn Asp
            420             425             430

Ala Ile Glu Ser Tyr Ser Lys Ser Gln Asp Glu Lys Arg Val Lys Ile
        435             440             445

Arg Leu Glu Ala Tyr Phe Ala Glu Phe Lys Ser Lys Asp Asp Ala Lys
    450             455             460

Lys Gln Phe Asp Leu Leu Glu Arg Ile Glu Glu Ala Tyr Ala Ile Val
465             470             475             480

Glu Pro Leu Leu Gly Ala Glu Tyr Pro Arg Asp Arg Asn Leu Lys Ala
            485             490             495

Asp Lys Lys Glu Val Gly Lys Ile Lys Asp Phe Leu Asp Ser Ile Lys
            500             505             510

Ser Leu Gln Phe Phe Leu Lys Pro Leu Leu Ser Ala Glu Ile Phe Asp
        515             520             525

Glu Lys Asp Leu Gly Phe Tyr Asn Gln Leu Glu Gly Tyr Tyr Glu Glu
    530             535             540

Ile Asp Ser Ile Gly His Leu Tyr Asn Lys Val Arg Asn Tyr Leu Thr
545             550             555             560

Gly Lys Ile Tyr Ser Lys Glu Lys Phe Lys Leu Asn Phe Glu Asn Ser
            565             570             575

Thr Leu Leu Lys Gly Trp Asp Glu Asn Arg Glu Val Ala Asn Leu Cys
        580             585             590

Val Ile Phe Arg Glu Asp Gln Lys Tyr Tyr Leu Gly Val Met Asp Lys
        595             600             605

Glu Asn Asn Thr Ile Leu Ser Asp Ile Pro Lys Val Lys Pro Asn Glu
    610             615             620

Leu Phe Tyr Glu Lys Met Val Tyr Lys Leu Ile Pro Thr Pro His Met
625             630             635             640

Gln Leu Pro Arg Ile Ile Phe Ser Ser Asp Asn Leu Ser Ile Tyr Asn
            645             650             655

Pro Ser Lys Ser Ile Leu Lys Ile Arg Glu Ala Lys Ser Phe Lys Glu
            660             665             670

Gly Lys Asn Phe Lys Leu Lys Asp Cys His Lys Phe Ile Asp Phe Tyr
        675             680             685

Lys Glu Ser Ile Ser Lys Asn Glu Asp Trp Ser Arg Phe Asp Phe Lys
    690             695             700

Phe Ser Lys Thr Ser Ser Tyr Glu Asn Ile Ser Glu Phe Tyr Arg Glu
```

```
705              710              715              720

Val Glu Arg Gln Gly Tyr Asn Leu Asp Phe Lys Lys Val Ser Lys Phe
                725              730              735

Tyr Ile Asp Ser Leu Val Glu Asp Gly Lys Leu Tyr Leu Phe Gln Ile
            740              745              750

Tyr Asn Lys Asp Phe Ser Ile Phe Ser Lys Gly Lys Pro Asn Leu His
        755              760              765

Thr Ile Tyr Phe Arg Ser Leu Phe Ser Lys Glu Asn Leu Lys Asp Val
    770              775              780

Cys Leu Lys Leu Asn Gly Glu Ala Glu Met Phe Phe Arg Lys Lys Ser
785              790              795              800

Ile Asn Tyr Asp Glu Lys Lys Arg Glu Gly His His Pro Glu Leu
            805              810              815

Phe Glu Lys Leu Lys Tyr Pro Ile Leu Lys Asp Lys Arg Tyr Ser Glu
            820              825              830

Asp Lys Phe Gln Phe His Leu Pro Ile Ser Leu Asn Phe Lys Ser Lys
        835              840              845

Glu Arg Leu Asn Phe Asn Leu Lys Val Asn Glu Phe Leu Lys Arg Asn
    850              855              860

Lys Asp Ile Asn Ile Ile Gly Ile Asp Arg Gly Glu Arg Asn Leu Leu
865              870              875              880

Tyr Leu Val Met Ile Asn Gln Lys Gly Glu Ile Leu Lys Gln Thr Leu
            885              890              895

Leu Asp Ser Met Gln Ser Gly Lys Gly Arg Pro Glu Ile Asn Tyr Lys
            900              905              910

Glu Lys Leu Gln Glu Lys Glu Ile Glu Arg Asp Lys Ala Arg Lys Ser
        915              920              925

Trp Gly Thr Val Glu Asn Ile Lys Glu Leu Lys Glu Gly Tyr Leu Ser
    930              935              940

Ile Val Ile His Gln Ile Ser Lys Leu Met Val Glu Asn Asn Ala Ile
945              950              955              960

Val Val Leu Glu Asp Leu Asn Ile Gly Phe Lys Arg Gly Arg Gln Lys
            965              970              975

Val Glu Arg Gln Val Tyr Gln Lys Phe Glu Lys Met Leu Ile Asp Lys
            980              985              990

Leu Asn Phe Leu Val Phe Lys Glu  Asn Lys Pro Thr Glu  Pro Gly Gly
        995              1000              1005

Val Leu  Lys Ala Tyr Gln Leu  Thr Asp Glu Phe Gln  Ser Phe Glu
    1010              1015              1020

Lys Leu  Ser Lys Gln Thr Gly  Phe Leu Phe Tyr Val  Pro Ser Trp
    1025              1030              1035

Asn Thr  Ser Lys Ile Asp Pro  Arg Thr Gly Phe Ile  Asp Phe Leu
    1040              1045              1050

His Pro  Ala Tyr Glu Asn Ile  Glu Lys Ala Lys Gln  Trp Ile Asn
    1055              1060              1065

Lys Phe  Asp Ser Ile Arg Phe  Asn Ser Lys Met Asp  Trp Phe Glu
    1070              1075              1080

Phe Thr  Ala Asp Thr Arg Lys  Phe Ser Glu Asn Leu  Met Leu Gly
    1085              1090              1095

Lys Asn  Arg Val Trp Val Ile  Cys Thr Thr Asn Val  Glu Arg Tyr
    1100              1105              1110

Phe Thr  Ser Lys Thr Ala Asn  Ser Ser Ile Gln Tyr  Asn Ser Ile
    1115              1120              1125
```

-continued

```
Gln Ile Thr Glu Lys Leu Lys Glu Leu Phe Val Asp Ile Pro Phe
    1130            1135            1140

Ser Asn Gly Gln Asp Leu Lys Pro Glu Ile Leu Arg Lys Asn Asp
    1145            1150            1155

Ala Val Phe Phe Lys Ser Leu Leu Phe Tyr Ile Lys Thr Thr Leu
    1160            1165            1170

Ser Leu Arg Gln Asn Asn Gly Lys Lys Gly Glu Glu Glu Lys Asp
    1175            1180            1185

Phe Ile Leu Ser Pro Val Val Asp Ser Lys Gly Arg Phe Phe Asn
    1190            1195            1200

Ser Leu Glu Ala Ser Asp Asp Glu Pro Lys Asp Ala Asp Ala Asn
    1205            1210            1215

Gly Ala Tyr His Ile Ala Leu Lys Gly Leu Met Asn Leu Leu Val
    1220            1225            1230

Leu Asn Glu Thr Lys Glu Glu Asn Leu Ser Arg Pro Lys Trp Lys
    1235            1240            1245

Ile Lys Asn Lys Asp Trp Leu Glu Phe Val Trp Glu Arg Asn Arg
    1250            1255            1260

<210> SEQ ID NO 32
<211> LENGTH: 1206
<212> TYPE: PRT
<213> ORGANISM: Lachnospiraceae

<400> SEQUENCE: 32

Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
            20                  25                  30

Asn Asn Ile Leu Glu Ser Asp Val Lys Arg Lys Gln Asn Tyr Glu His
        35                  40                  45

Val Lys Gly Ile Leu Asp Glu Tyr His Lys Gln Leu Ile Asn Glu Ala
    50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140

Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Glu Gln Asp
        195                 200                 205

Ser Leu Phe Ile Val Glu Thr Phe Asn Lys Thr Leu Thr Gln Asp Gly
    210                 215                 220

Ile Asp Thr Tyr Asn Ser Gln Val Gly Lys Ile Asn Ser Ser Ile Asn
```

```
225                 230                 235                 240

Leu Tyr Asn Gln Lys Asn Gln Lys Ala Asn Gly Phe Arg Lys Ile Pro
                245                 250                 255

Lys Met Lys Met Leu Tyr Lys Gln Ile Leu Ser Asp Arg Glu Glu Ser
                260                 265                 270

Phe Ile Asp Glu Phe Gln Ser Asp Glu Val Leu Ile Asp Asn Val Glu
                275                 280                 285

Ser Tyr Gly Ser Val Leu Ile Glu Ser Leu Lys Ser Ser Lys Val Ser
                290                 295                 300

Ala Phe Phe Asp Ala Leu Arg Glu Ser Lys Gly Lys Asn Val Tyr Val
305                 310                 315                 320

Lys Asn Asp Leu Ala Lys Thr Ala Met Ser Asn Ile Val Phe Glu Asn
                325                 330                 335

Trp Arg Thr Phe Asp Asp Leu Leu Asn Gln Glu Tyr Asp Leu Ala Asn
                340                 345                 350

Glu Asn Lys Lys Lys Asp Asp Lys Tyr Phe Glu Lys Arg Gln Lys Glu
                355                 360                 365

Leu Lys Lys Asn Lys Ser Tyr Ser Leu Glu His Leu Cys Asn Leu Ser
                370                 375                 380

Glu Asp Ser Cys Asn Leu Ile Glu Asn Tyr Ile His Gln Ile Ser Asp
385                 390                 395                 400

Asp Ile Glu Asn Ile Ile Ile Asn Asn Glu Thr Phe Leu Arg Ile Val
                405                 410                 415

Ile Asn Glu His Asp Arg Ser Arg Lys Leu Ala Lys Asn Arg Lys Ala
                420                 425                 430

Val Lys Ala Ile Lys Asp Phe Leu Asp Ser Ile Lys Val Leu Glu Arg
                435                 440                 445

Glu Leu Lys Leu Ile Asn Ser Ser Gly Gln Glu Leu Glu Lys Asp Leu
                450                 455                 460

Ile Val Tyr Ser Ala His Glu Glu Leu Leu Val Glu Leu Lys Gln Val
465                 470                 475                 480

Asp Ser Leu Tyr Asn Met Thr Arg Asn Tyr Leu Thr Lys Lys Pro Phe
                485                 490                 495

Ser Thr Glu Lys Val Lys Leu Asn Phe Asn Arg Ser Thr Leu Leu Asn
                500                 505                 510

Gly Trp Asp Arg Asn Lys Glu Thr Asp Asn Leu Gly Val Leu Leu Leu
                515                 520                 525

Lys Asp Gly Lys Tyr Tyr Leu Gly Ile Met Asn Thr Ser Ala Asn Lys
                530                 535                 540

Ala Phe Val Asn Pro Pro Val Ala Lys Thr Glu Lys Val Phe Lys Lys
545                 550                 555                 560

Val Asp Tyr Lys Leu Leu Pro Val Pro Asn Gln Met Leu Pro Lys Val
                565                 570                 575

Phe Phe Ala Lys Ser Asn Ile Asp Phe Tyr Asn Pro Ser Ser Glu Ile
                580                 585                 590

Tyr Ser Asn Tyr Lys Lys Gly Thr His Lys Lys Gly Asn Met Phe Ser
                595                 600                 605

Leu Glu Asp Cys His Asn Leu Ile Asp Phe Phe Lys Glu Ser Ile Ser
                610                 615                 620

Lys His Glu Asp Trp Ser Lys Phe Gly Phe Lys Phe Ser Asp Thr Ala
625                 630                 635                 640

Ser Tyr Asn Asp Ile Ser Glu Phe Tyr Arg Glu Val Glu Lys Gln Gly
                645                 650                 655
```

```
Tyr Lys Leu Thr Tyr Thr Asp Ile Asp Glu Thr Tyr Ile Asn Asp Leu
            660                 665                 670

Ile Glu Arg Asn Glu Leu Tyr Leu Phe Gln Ile Tyr Asn Lys Asp Phe
            675                 680                 685

Ser Met Tyr Ser Lys Gly Lys Leu Asn Leu His Thr Leu Tyr Phe Met
    690                 695                 700

Met Leu Phe Asp Gln Arg Asn Ile Asp Asp Val Val Tyr Lys Leu Asn
705                 710                 715                 720

Gly Glu Ala Glu Val Phe Tyr Arg Pro Ala Ser Ile Ser Glu Asp Glu
                725                 730                 735

Leu Ile Ile His Lys Ala Gly Glu Glu Ile Lys Asn Lys Asn Pro Asn
                740                 745                 750

Arg Ala Arg Thr Lys Glu Thr Ser Thr Phe Ser Tyr Asp Ile Val Lys
            755                 760                 765

Asp Lys Arg Tyr Ser Lys Asp Lys Phe Thr Leu His Ile Pro Ile Thr
    770                 775                 780

Met Asn Phe Gly Val Asp Glu Val Lys Arg Phe Asn Asp Ala Val Asn
785                 790                 795                 800

Ser Ala Ile Arg Ile Asp Glu Asn Val Asn Val Ile Gly Ile Asp Arg
                805                 810                 815

Gly Glu Arg Asn Leu Leu Tyr Val Val Val Ile Asp Ser Lys Gly Asn
                820                 825                 830

Ile Leu Glu Gln Ile Ser Leu Asn Ser Ile Ile Asn Lys Glu Tyr Asp
            835                 840                 845

Ile Glu Thr Asp Tyr His Ala Leu Leu Asp Glu Arg Glu Gly Gly Arg
    850                 855                 860

Asp Lys Ala Arg Lys Asp Trp Asn Thr Val Glu Asn Ile Arg Asp Leu
865                 870                 875                 880

Lys Ala Gly Tyr Leu Ser Gln Val Val Asn Val Val Ala Lys Leu Val
                885                 890                 895

Leu Lys Tyr Asn Ala Ile Ile Cys Leu Glu Asp Leu Asn Phe Gly Phe
                900                 905                 910

Lys Arg Gly Arg Gln Lys Val Glu Lys Gln Val Tyr Gln Lys Phe Glu
            915                 920                 925

Lys Met Leu Ile Asp Lys Leu Asn Tyr Leu Val Ile Asp Lys Ser Arg
    930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
                965                 970                 975

Val Ile Tyr Tyr Val Pro Ala Tyr Leu Thr Ser Lys Ile Asp Pro Thr
                980                 985                 990

Thr Gly Phe Ala Asn Leu Phe Tyr  Met Lys Cys Glu Asn  Val Glu Lys
            995                 1000                1005

Ser Lys  Arg Phe Phe Asp Gly  Phe Asp Phe Ile Arg  Phe Asn Ala
    1010                1015                1020

Leu Glu  Asn Val Phe Glu Phe  Gly Phe Asp Tyr Arg  Ser Phe Thr
    1025                1030                1035

Gln Arg  Ala Cys Gly Ile Asn  Ser Lys Trp Thr Val  Cys Thr Asn
    1040                1045                1050

Gly Glu  Arg Ile Ile Lys Tyr  Arg Asn Pro Asp Lys  Asn Asn Met
    1055                1060                1065
```

```
Phe Asp  Glu Lys Val Val Val  Val Thr Asp Glu Met  Lys Asn Leu
    1070              1075              1080

Phe Glu  Gln Tyr Lys Ile Pro  Tyr Glu Asp Gly Arg  Asn Val Lys
    1085              1090              1095

Asp Met  Ile Ile Ser Asn Glu  Glu Ala Glu Phe Tyr  Arg Arg Leu
    1100              1105              1110

Tyr Arg  Leu Leu Gln Gln Thr  Leu Gln Met Arg Asn  Ser Thr Ser
    1115              1120              1125

Asp Gly  Thr Arg Asp Tyr Ile  Ile Ser Pro Val Lys  Asn Lys Arg
    1130              1135              1140

Glu Ala  Tyr Phe Asn Ser Glu  Leu Ser Asp Gly Ser  Val Pro Lys
    1145              1150              1155

Asp Ala  Asp Ala Asn Gly Ala  Tyr Asn Ile Ala Arg  Lys Gly Leu
    1160              1165              1170

Trp Val  Leu Glu Gln Ile Arg  Gln Lys Ser Glu Gly  Glu Lys Ile
    1175              1180              1185

Asn Leu  Ala Met Thr Asn Ala  Glu Trp Leu Glu Tyr  Ala Gln Thr
    1190              1195              1200

His Leu  Leu
    1205

<210> SEQ ID NO 33
<211> LENGTH: 1300
<212> TYPE: PRT
<213> ORGANISM: Francisella tularensis

<400> SEQUENCE: 33

Met Ser Ile Tyr Gln Glu Phe Val Asn Lys Tyr Ser Leu Ser Lys Thr
1               5               10              15

Leu Arg Phe Glu Leu Ile Pro Gln Gly Lys Thr Leu Glu Asn Ile Lys
            20              25              30

Ala Arg Gly Leu Ile Leu Asp Asp Glu Lys Arg Ala Lys Asp Tyr Lys
        35              40              45

Lys Ala Lys Gln Ile Ile Asp Lys Tyr His Gln Phe Phe Ile Glu Glu
    50              55              60

Ile Leu Ser Ser Val Cys Ile Ser Glu Asp Leu Leu Gln Asn Tyr Ser
65              70              75              80

Asp Val Tyr Phe Lys Leu Lys Lys Ser Asp Asp Asp Asn Leu Gln Lys
            85              90              95

Asp Phe Lys Ser Ala Lys Asp Thr Ile Lys Lys Gln Ile Ser Glu Tyr
            100             105             110

Ile Lys Asp Ser Glu Lys Phe Lys Asn Leu Phe Asn Gln Asn Leu Ile
        115             120             125

Asp Ala Lys Lys Gly Gln Glu Ser Asp Leu Ile Leu Trp Leu Lys Gln
    130             135             140

Ser Lys Asp Asn Gly Ile Glu Leu Phe Lys Ala Asn Ser Asp Ile Thr
145             150             155             160

Asp Ile Asp Glu Ala Leu Glu Ile Ile Lys Ser Phe Lys Gly Trp Thr
            165             170             175

Thr Tyr Phe Lys Gly Phe His Glu Asn Arg Lys Asn Val Tyr Ser Ser
            180             185             190

Asn Asp Ile Pro Thr Ser Ile Ile Tyr Arg Ile Val Asp Asp Asn Leu
            195             200             205

Pro Lys Phe Leu Glu Asn Lys Ala Lys Tyr Glu Ser Leu Lys Asp Lys
    210             215             220
```

-continued

```
Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
                260                 265                 270

Leu Asn Gln Ser Gly Ile Thr Lys Phe Asn Thr Ile Ile Gly Gly Lys
            275                 280                 285

Phe Val Asn Gly Glu Asn Thr Lys Arg Lys Gly Ile Asn Glu Tyr Ile
        290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
                340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Asp Leu Lys Ala Gln
        370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
                420                 425                 430

Pro Ser Lys Lys Glu Gln Glu Leu Ile Ala Lys Lys Thr Glu Lys Ala
            435                 440                 445

Lys Tyr Leu Ser Leu Glu Thr Ile Lys Leu Ala Leu Glu Glu Phe Asn
        450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
        530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
        610                 615                 620

Asp Asp Lys Tyr Tyr Leu Gly Val Met Asn Lys Lys Asn Asn Lys Ile
625                 630                 635                 640
```

-continued

```
Phe Asp Asp Lys Ala Ile Lys Glu Asn Lys Gly Glu Gly Tyr Lys Lys
              645                 650                 655

Ile Val Tyr Lys Leu Leu Pro Gly Ala Asn Lys Met Leu Pro Lys Val
              660                 665                 670

Phe Phe Ser Ala Lys Ser Ile Lys Phe Tyr Asn Pro Ser Glu Asp Ile
              675                 680                 685

Leu Arg Ile Arg Asn His Ser Thr His Thr Lys Asn Gly Ser Pro Gln
        690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
              725                 730                 735

Phe Gly Phe Arg Phe Ser Asp Thr Gln Arg Tyr Asn Ser Ile Asp Glu
              740                 745                 750

Phe Tyr Arg Glu Val Glu Asn Gln Gly Tyr Lys Leu Thr Phe Glu Asn
              755                 760                 765

Ile Ser Glu Ser Tyr Ile Asp Ser Val Val Asn Gln Gly Lys Leu Tyr
        770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
              805                 810                 815

Leu Gln Asp Val Val Tyr Lys Leu Asn Gly Glu Ala Glu Leu Phe Tyr
              820                 825                 830

Arg Lys Gln Ser Ile Pro Lys Lys Ile Thr His Pro Ala Lys Glu Ala
              835                 840                 845

Ile Ala Asn Lys Asn Lys Asp Asn Pro Lys Lys Glu Ser Val Phe Glu
        850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
              885                 890                 895

Asn Asp Glu Ile Asn Leu Leu Leu Lys Glu Lys Ala Asn Asp Val His
              900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
        930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
              965                 970                 975

Ile Lys Glu Met Lys Glu Gly Tyr Leu Ser Gln Val Val His Glu Ile
              980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
```

```
        1055                    1060                    1065

Lys Gln  Thr Gly Ile Ile Tyr  Tyr Val Pro Ala Gly  Phe Thr Ser
    1070                    1075                    1080

Lys Ile  Cys Pro Val Thr Gly  Phe Val Asn Gln Leu  Tyr Pro Lys
    1085                    1090                    1095

Tyr Glu  Ser Val Ser Lys Ser  Gln Glu Phe Phe Ser  Lys Phe Asp
    1100                    1105                    1110

Lys Ile  Cys Tyr Asn Leu Asp  Lys Gly Tyr Phe Glu  Phe Ser Phe
    1115                    1120                    1125

Asp Tyr  Lys Asn Phe Gly Asp  Lys Ala Ala Lys Gly  Lys Trp Thr
    1130                    1135                    1140

Ile Ala  Ser Phe Gly Ser Arg  Leu Ile Asn Phe Arg  Asn Ser Asp
    1145                    1150                    1155

Lys Asn  His Asn Trp Asp Thr  Arg Glu Val Tyr Pro  Thr Lys Glu
    1160                    1165                    1170

Leu Glu  Lys Leu Leu Lys Asp  Tyr Ser Ile Glu Tyr  Gly His Gly
    1175                    1180                    1185

Glu Cys  Ile Lys Ala Ala Ile  Cys Gly Glu Ser Asp  Lys Lys Phe
    1190                    1195                    1200

Phe Ala  Lys Leu Thr Ser Val  Leu Asn Thr Ile Leu  Gln Met Arg
    1205                    1210                    1215

Asn Ser  Lys Thr Gly Thr Glu  Leu Asp Tyr Leu Ile  Ser Pro Val
    1220                    1225                    1230

Ala Asp  Val Asn Gly Asn Phe  Phe Asp Ser Arg Gln  Ala Pro Lys
    1235                    1240                    1245

Asn Met  Pro Gln Asp Ala Asp  Ala Asn Gly Ala Tyr  His Ile Gly
    1250                    1255                    1260

Leu Lys  Gly Leu Met Leu Leu  Gly Arg Ile Lys Asn  Asn Gln Glu
    1265                    1270                    1275

Gly Lys  Lys Leu Asn Leu Val  Ile Lys Asn Glu Glu  Tyr Phe Glu
    1280                    1285                    1290

Phe Val  Gln Asn Arg Asn Asn
    1295                    1300

<210> SEQ ID NO 34
<211> LENGTH: 15
<212> TYPE: PRT
<213> ORGANISM: artificial
<220> FEATURE:
<223> OTHER INFORMATION: SLN

<400> SEQUENCE: 34

Gly Gly Met Ala Ala Pro Lys Lys Lys Arg Lys Val Asp Gly Gly
1               5                   10                  15

<210> SEQ ID NO 35
<211> LENGTH: 8
<212> TYPE: PRT
<213> ORGANISM: artificial
<220> FEATURE:
<223> OTHER INFORMATION: linker1

<400> SEQUENCE: 35

Gly Ile His Gly Val Pro Ala Ala
1               5

<210> SEQ ID NO 36
<211> LENGTH: 12
```

```
<212> TYPE: PRT
<213> ORGANISM: artificial
<220> FEATURE:
<223> OTHER INFORMATION: linker2

<400> SEQUENCE: 36

Pro Glu Phe Met Ala Met Glu Ala Pro Gly Ile Arg
1               5                   10

<210> SEQ ID NO 37
<211> LENGTH: 31
<212> TYPE: PRT
<213> ORGANISM: artificial
<220> FEATURE:
<223> OTHER INFORMATION: 6xHis-3xFlag Tag

<400> SEQUENCE: 37

His His His His His His Gly Asp Tyr Lys Asp Asp Asp Lys Asp
1               5                   10                  15

Tyr Lys Asp Asp Asp Asp Lys Asp Tyr Lys Asp Asp Asp Asp Lys
            20                  25                  30

<210> SEQ ID NO 38
<211> LENGTH: 1368
<212> TYPE: PRT
<213> ORGANISM: Streptococcus pyogenes

<400> SEQUENCE: 38

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240
```

```
Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
```

```
                660               665               670

Lys Gln Ser Gly Lys Thr Ile Leu Asp Phe Leu Lys Ser Asp Gly Phe
            675               680               685

Ala Asn Arg Asn Phe Met Gln Leu Ile His Asp Asp Ser Leu Thr Phe
    690               695               700

Lys Glu Asp Ile Gln Lys Ala Gln Val Ser Gly Gln Gly Asp Ser Leu
705               710               715               720

His Glu His Ile Ala Asn Leu Ala Gly Ser Pro Ala Ile Lys Lys Gly
                725               730               735

Ile Leu Gln Thr Val Lys Val Val Asp Glu Leu Val Lys Val Met Gly
                740               745               750

Arg His Lys Pro Glu Asn Ile Val Ile Glu Met Ala Arg Glu Asn Gln
            755               760               765

Thr Thr Gln Lys Gly Gln Lys Asn Ser Arg Glu Arg Met Lys Arg Ile
    770               775               780

Glu Glu Gly Ile Lys Glu Leu Gly Ser Gln Ile Leu Lys Glu His Pro
785               790               795               800

Val Glu Asn Thr Gln Leu Gln Asn Glu Lys Leu Tyr Leu Tyr Tyr Leu
                805               810               815

Gln Asn Gly Arg Asp Met Tyr Val Asp Gln Glu Leu Asp Ile Asn Arg
                820               825               830

Leu Ser Asp Tyr Asp Val Asp His Ile Val Pro Gln Ser Phe Leu Lys
            835               840               845

Asp Asp Ser Ile Asp Asn Lys Val Leu Thr Arg Ser Asp Lys Asn Arg
    850               855               860

Gly Lys Ser Asp Asn Val Pro Ser Glu Glu Val Val Lys Lys Met Lys
865               870               875               880

Asn Tyr Trp Arg Gln Leu Leu Asn Ala Lys Leu Ile Thr Gln Arg Lys
                885               890               895

Phe Asp Asn Leu Thr Lys Ala Glu Arg Gly Gly Leu Ser Glu Leu Asp
                900               905               910

Lys Ala Gly Phe Ile Lys Arg Gln Leu Val Glu Thr Arg Gln Ile Thr
            915               920               925

Lys His Val Ala Gln Ile Leu Asp Ser Arg Met Asn Thr Lys Tyr Asp
    930               935               940

Glu Asn Asp Lys Leu Ile Arg Glu Val Lys Val Ile Thr Leu Lys Ser
945               950               955               960

Lys Leu Val Ser Asp Phe Arg Lys Asp Phe Gln Phe Tyr Lys Val Arg
                965               970               975

Glu Ile Asn Asn Tyr His His Ala His Asp Ala Tyr Leu Asn Ala Val
                980               985               990

Val Gly Thr Ala Leu Ile Lys Lys  Tyr Pro Lys Leu Glu  Ser Glu Phe
            995               1000               1005

Val Tyr  Gly Asp Tyr Lys Val  Tyr Asp Val Arg Lys  Met Ile Ala
    1010               1015               1020

Lys Ser  Glu Gln Glu Ile Gly  Lys Ala Thr Ala Lys  Tyr Phe Phe
    1025               1030               1035

Tyr Ser  Asn Ile Met Asn Phe  Phe Lys Thr Glu Ile  Thr Leu Ala
    1040               1045               1050

Asn Gly  Glu Ile Arg Lys Arg  Pro Leu Ile Glu Thr  Asn Gly Glu
    1055               1060               1065

Thr Gly  Glu Ile Val Trp Asp  Lys Gly Arg Asp Phe  Ala Thr Val
    1070               1075               1080
```

```
Arg Lys Val Leu Ser Met Pro  Gln Val Asn Ile Val  Lys Lys Thr
    1085                1090                 1095

Glu Val  Gln Thr Gly Gly Phe  Ser Lys Glu Ser Ile  Leu Pro Lys
    1100                1105                 1110

Arg Asn  Ser Asp Lys Leu Ile  Ala Arg Lys Lys Asp  Trp Asp Pro
    1115                1120                 1125

Lys Lys  Tyr Gly Gly Phe Asp  Ser Pro Thr Val Ala  Tyr Ser Val
    1130                1135                 1140

Leu Val  Val Ala Lys Val Glu  Lys Gly Lys Ser Lys  Lys Leu Lys
    1145                1150                 1155

Ser Val  Lys Glu Leu Leu Gly  Ile Thr Ile Met Glu  Arg Ser Ser
    1160                1165                 1170

Phe Glu  Lys Asn Pro Ile Asp  Phe Leu Glu Ala Lys  Gly Tyr Lys
    1175                1180                 1185

Glu Val  Lys Lys Asp Leu Ile  Ile Lys Leu Pro Lys  Tyr Ser Leu
    1190                1195                 1200

Phe Glu  Leu Glu Asn Gly Arg  Lys Arg Met Leu Ala  Ser Ala Gly
    1205                1210                 1215

Glu Leu  Gln Lys Gly Asn Glu  Leu Ala Leu Pro Ser  Lys Tyr Val
    1220                1225                 1230

Asn Phe  Leu Tyr Leu Ala Ser  His Tyr Glu Lys Leu  Lys Gly Ser
    1235                1240                 1245

Pro Glu  Asp Asn Glu Gln Lys  Gln Leu Phe Val Glu  Gln His Lys
    1250                1255                 1260

His Tyr  Leu Asp Glu Ile Ile  Glu Gln Ile Ser Glu  Phe Ser Lys
    1265                1270                 1275

Arg Val  Ile Leu Ala Asp Ala  Asn Leu Asp Lys Val  Leu Ser Ala
    1280                1285                 1290

Tyr Asn  Lys His Arg Asp Lys  Pro Ile Arg Glu Gln  Ala Glu Asn
    1295                1300                 1305

Ile Ile  His Leu Phe Thr Leu  Thr Asn Leu Gly Ala  Pro Ala Ala
    1310                1315                 1320

Phe Lys  Tyr Phe Asp Thr Thr  Ile Asp Arg Lys Arg  Tyr Thr Ser
    1325                1330                 1335

Thr Lys  Glu Val Leu Asp Ala  Thr Leu Ile His Gln  Ser Ile Thr
    1340                1345                 1350

Gly Leu  Tyr Glu Thr Arg Ile  Asp Leu Ser Gln Leu  Gly Gly Asp
    1355                1360                 1365
```

<210> SEQ ID NO 39
<211> LENGTH: 1409
<212> TYPE: PRT
<213> ORGANISM: Streptococcus thermophiles

<400> SEQUENCE: 39

```
Met Leu Phe Asn Lys Cys Ile Ile Ile Ser Ile Asn Leu Asp Phe Ser
1               5                   10                  15

Asn Lys Glu Lys Cys Met Thr Lys Pro Tyr Ser Ile Gly Leu Asp Ile
            20                  25                  30

Gly Thr Asn Ser Val Gly Trp Ala Val Ile Thr Asp Asn Tyr Lys Val
        35                  40                  45

Pro Ser Lys Lys Met Lys Val Leu Gly Asn Thr Ser Lys Lys Tyr Ile
    50                  55                  60

Lys Lys Asn Leu Leu Gly Val Leu Leu Phe Asp Ser Gly Ile Thr Ala
```

-continued

```
65                  70                  75                  80

Glu Gly Arg Arg Leu Lys Arg Thr Ala Arg Arg Arg Tyr Thr Arg Arg
                85                  90                  95

Arg Asn Arg Ile Leu Tyr Leu Gln Glu Ile Phe Ser Thr Glu Met Ala
                100                 105                 110

Thr Leu Asp Asp Ala Phe Phe Gln Arg Leu Asp Asp Ser Phe Leu Val
                115                 120                 125

Pro Asp Asp Lys Arg Asp Ser Lys Tyr Pro Ile Phe Gly Asn Leu Val
                130                 135                 140

Glu Glu Lys Val Tyr His Asp Glu Phe Pro Thr Ile Tyr His Leu Arg
145                 150                 155                 160

Lys Tyr Leu Ala Asp Ser Thr Lys Lys Ala Asp Leu Arg Leu Val Tyr
                165                 170                 175

Leu Ala Leu Ala His Met Ile Lys Tyr Arg Gly His Phe Leu Ile Glu
                180                 185                 190

Gly Glu Phe Asn Ser Lys Asn Asn Asp Ile Gln Lys Asn Phe Gln Asp
                195                 200                 205

Phe Leu Asp Thr Tyr Asn Ala Ile Phe Glu Ser Asp Leu Ser Leu Glu
                210                 215                 220

Asn Ser Lys Gln Leu Glu Glu Ile Val Lys Asp Lys Ile Ser Lys Leu
225                 230                 235                 240

Glu Lys Lys Asp Arg Ile Leu Lys Leu Phe Pro Gly Glu Lys Asn Ser
                245                 250                 255

Gly Ile Phe Ser Glu Phe Leu Lys Leu Ile Val Gly Asn Gln Ala Asp
                260                 265                 270

Phe Arg Lys Cys Phe Asn Leu Asp Glu Lys Ala Ser Leu His Phe Ser
                275                 280                 285

Lys Glu Ser Tyr Asp Glu Asp Leu Glu Thr Leu Leu Gly Tyr Ile Gly
                290                 295                 300

Asp Asp Tyr Ser Asp Val Phe Leu Lys Ala Lys Lys Leu Tyr Asp Ala
305                 310                 315                 320

Ile Leu Leu Ser Gly Phe Leu Thr Val Thr Asp Asn Glu Thr Glu Ala
                325                 330                 335

Pro Leu Ser Ser Ala Met Ile Lys Arg Tyr Asn Glu His Lys Glu Asp
                340                 345                 350

Leu Ala Leu Leu Lys Glu Tyr Ile Arg Asn Ile Ser Leu Lys Thr Tyr
                355                 360                 365

Asn Glu Val Phe Lys Asp Asp Thr Lys Asn Gly Tyr Ala Gly Tyr Ile
                370                 375                 380

Asp Gly Lys Thr Asn Gln Glu Asp Phe Tyr Val Tyr Leu Lys Asn Leu
385                 390                 395                 400

Leu Ala Glu Phe Glu Gly Ala Asp Tyr Phe Leu Glu Lys Ile Asp Arg
                405                 410                 415

Glu Asp Phe Leu Arg Lys Gln Arg Thr Phe Asp Asn Gly Ser Ile Pro
                420                 425                 430

Tyr Gln Ile His Leu Gln Glu Met Arg Ala Ile Leu Asp Lys Gln Ala
                435                 440                 445

Lys Phe Tyr Pro Phe Leu Ala Lys Asn Lys Glu Arg Ile Glu Lys Ile
                450                 455                 460

Leu Thr Phe Arg Ile Pro Tyr Tyr Val Gly Pro Leu Ala Arg Gly Asn
465                 470                 475                 480

Ser Asp Phe Ala Trp Ser Ile Arg Lys Arg Asn Glu Lys Ile Thr Pro
                485                 490                 495
```

```
Trp Asn Phe Glu Asp Val Ile Asp Lys Glu Ser Ser Ala Glu Ala Phe
            500                 505                 510

Ile Asn Arg Met Thr Ser Phe Asp Leu Tyr Leu Pro Glu Glu Lys Val
            515                 520                 525

Leu Pro Lys His Ser Leu Leu Tyr Glu Thr Phe Asn Val Tyr Asn Glu
            530                 535                 540

Leu Thr Lys Val Arg Phe Ile Ala Glu Ser Met Arg Asp Tyr Gln Phe
545                 550                 555                 560

Leu Asp Ser Lys Gln Lys Lys Asp Ile Val Arg Leu Tyr Phe Lys Asp
                565                 570                 575

Lys Arg Lys Val Thr Asp Lys Asp Ile Ile Glu Tyr Leu His Ala Ile
            580                 585                 590

Tyr Gly Tyr Asp Gly Ile Glu Leu Lys Gly Ile Glu Lys Gln Phe Asn
            595                 600                 605

Ser Ser Leu Ser Thr Tyr His Asp Leu Leu Asn Ile Ile Asn Asp Lys
            610                 615                 620

Glu Phe Leu Asp Asp Ser Ser Asn Glu Ala Ile Ile Glu Glu Ile Ile
625                 630                 635                 640

His Thr Leu Thr Ile Phe Glu Asp Arg Glu Met Ile Lys Gln Arg Leu
                645                 650                 655

Ser Lys Phe Glu Asn Ile Phe Asp Lys Ser Val Leu Lys Lys Leu Ser
            660                 665                 670

Arg Arg His Tyr Thr Gly Trp Gly Lys Leu Ser Ala Lys Leu Ile Asn
            675                 680                 685

Gly Ile Arg Asp Glu Lys Ser Gly Asn Thr Ile Leu Asp Tyr Leu Ile
            690                 695                 700

Asp Asp Gly Ile Ser Asn Arg Asn Phe Met Gln Leu Ile His Asp Asp
705                 710                 715                 720

Ala Leu Ser Phe Lys Lys Lys Ile Gln Lys Ala Gln Ile Ile Gly Asp
                725                 730                 735

Glu Asp Lys Gly Asn Ile Lys Glu Val Val Lys Ser Leu Pro Gly Ser
            740                 745                 750

Pro Ala Ile Lys Lys Gly Ile Leu Gln Ser Ile Lys Ile Val Asp Glu
            755                 760                 765

Leu Val Lys Val Met Gly Gly Arg Lys Pro Glu Ser Ile Val Val Glu
            770                 775                 780

Met Ala Arg Glu Asn Gln Tyr Thr Asn Gln Gly Lys Ser Asn Ser Gln
785                 790                 795                 800

Gln Arg Leu Lys Arg Leu Glu Lys Ser Leu Lys Glu Leu Gly Ser Lys
                805                 810                 815

Ile Leu Lys Glu Asn Ile Pro Ala Lys Leu Ser Lys Ile Asp Asn Asn
            820                 825                 830

Ala Leu Gln Asn Asp Arg Leu Tyr Leu Tyr Tyr Leu Gln Asn Gly Lys
            835                 840                 845

Asp Met Tyr Thr Gly Asp Asp Leu Asp Ile Asp Arg Leu Ser Asn Tyr
            850                 855                 860

Asp Ile Asp His Ile Ile Pro Gln Ala Phe Leu Lys Asp Asn Ser Ile
865                 870                 875                 880

Asp Asn Lys Val Leu Val Ser Ser Ala Ser Asn Arg Gly Lys Ser Asp
                885                 890                 895

Asp Phe Pro Ser Leu Glu Val Val Lys Lys Arg Lys Thr Phe Trp Tyr
            900                 905                 910
```

-continued

```
Gln Leu Leu Lys Ser Lys Leu Ile Ser Gln Arg Lys Phe Asp Asn Leu
        915                 920                 925

Thr Lys Ala Glu Arg Gly Gly Leu Leu Pro Glu Asp Lys Ala Gly Phe
        930                 935                 940

Ile Gln Arg Gln Leu Val Glu Thr Arg Gln Ile Thr Lys His Val Ala
945                 950                 955                 960

Arg Leu Leu Asp Glu Lys Phe Asn Asn Lys Lys Asp Glu Asn Asn Arg
                965                 970                 975

Ala Val Arg Thr Val Lys Ile Ile Thr Leu Lys Ser Thr Leu Val Ser
                980                 985                 990

Gln Phe Arg Lys Asp Phe Glu Leu  Tyr Lys Val Arg Glu  Ile Asn Asp
        995                 1000                1005

Phe His  His Ala His Asp Ala  Tyr Leu Asn Ala Val  Ile Ala Ser
        1010                1015                1020

Ala Leu  Leu Lys Lys Tyr Pro  Lys Leu Glu Pro Glu  Phe Val Tyr
        1025                1030                1035

Gly Asp  Tyr Pro Lys Tyr Asn  Ser Phe Arg Glu Arg  Lys Ser Ala
        1040                1045                1050

Thr Glu  Lys Val Tyr Phe Tyr  Ser Asn Ile Met Asn  Ile Phe Lys
        1055                1060                1065

Lys Ser  Ile Ser Leu Ala Asp  Gly Arg Val Ile Glu  Arg Pro Leu
        1070                1075                1080

Ile Glu  Val Asn Glu Glu Thr  Gly Glu Ser Val Trp  Asn Lys Glu
        1085                1090                1095

Ser Asp  Leu Ala Thr Val Arg  Arg Val Leu Ser Tyr  Pro Gln Val
        1100                1105                1110

Asn Val  Val Lys Lys Val Glu  Glu Gln Asn His Gly  Leu Asp Arg
        1115                1120                1125

Gly Lys  Pro Lys Gly Leu Phe  Asn Ala Asn Leu Ser  Ser Lys Pro
        1130                1135                1140

Lys Pro  Asn Ser Asn Glu Asn  Leu Val Gly Ala Lys  Glu Tyr Leu
        1145                1150                1155

Asp Pro  Lys Lys Tyr Gly Gly  Tyr Ala Gly Ile Ser  Asn Ser Phe
        1160                1165                1170

Ala Val  Leu Val Lys Gly Thr  Ile Glu Lys Gly Ala  Lys Lys Lys
        1175                1180                1185

Ile Thr  Asn Val Leu Glu Phe  Gln Gly Ile Ser Ile  Leu Asp Arg
        1190                1195                1200

Ile Asn  Tyr Arg Lys Asp Lys  Leu Asn Phe Leu Leu  Glu Lys Gly
        1205                1210                1215

Tyr Lys  Asp Ile Glu Leu Ile  Ile Glu Leu Pro Lys  Tyr Ser Leu
        1220                1225                1230

Phe Glu  Leu Ser Asp Gly Ser  Arg Arg Met Leu Ala  Ser Ile Leu
        1235                1240                1245

Ser Thr  Asn Asn Lys Arg Gly  Glu Ile His Lys Gly  Asn Gln Ile
        1250                1255                1260

Phe Leu  Ser Gln Lys Phe Val  Lys Leu Leu Tyr His  Ala Lys Arg
        1265                1270                1275

Ile Ser  Asn Thr Ile Asn Glu  Asn His Arg Lys Tyr  Val Glu Asn
        1280                1285                1290

His Lys  Lys Glu Phe Glu Glu  Leu Phe Tyr Tyr Ile  Leu Glu Phe
        1295                1300                1305

Asn Glu  Asn Tyr Val Gly Ala  Lys Lys Asn Gly Lys  Leu Leu Asn
```

```
        1310              1315              1320
```

Ser Ala  Phe Gln Ser Trp Gln  Asn His Ser Ile Asp  Glu Leu Cys
    1325              1330              1335

Ser Ser  Phe Ile Gly Pro Thr  Gly Ser Glu Arg Lys  Gly Leu Phe
    1340              1345              1350

Glu Leu  Thr Ser Arg Gly Ser  Ala Ala Asp Phe Glu  Phe Leu Gly
    1355              1360              1365

Val Lys  Ile Pro Arg Tyr Arg  Asp Tyr Thr Pro Ser  Ser Leu Leu
    1370              1375              1380

Lys Asp  Ala Thr Leu Ile His  Gln Ser Val Thr Gly  Leu Tyr Glu
    1385              1390              1395

Thr Arg  Ile Asp Leu Ala Lys  Leu Gly Glu Gly
    1400              1405

<210> SEQ ID NO 40
<211> LENGTH: 1053
<212> TYPE: PRT
<213> ORGANISM: Staphylococcus aureus

<400> SEQUENCE: 40
```

Met Lys Arg Asn Tyr Ile Leu Gly Leu Asp Ile Gly Ile Thr Ser Val
1                 5                  10                 15

Gly Tyr Gly Ile Ile Asp Tyr Glu Thr Arg Asp Val Ile Asp Ala Gly
                20                 25                 30

Val Arg Leu Phe Lys Glu Ala Asn Val Glu Asn Asn Glu Gly Arg Arg
        35                 40                 45

Ser Lys Arg Gly Ala Arg Arg Leu Lys Arg Arg Arg His Arg Ile
    50                 55                 60

Gln Arg Val Lys Lys Leu Leu Phe Asp Tyr Asn Leu Leu Thr Asp His
65                 70                 75                 80

Ser Glu Leu Ser Gly Ile Asn Pro Tyr Glu Ala Arg Val Lys Gly Leu
                85                 90                 95

Ser Gln Lys Leu Ser Glu Glu Glu Phe Ser Ala Ala Leu Leu His Leu
            100                105                110

Ala Lys Arg Arg Gly Val His Asn Val Asn Glu Val Glu Glu Asp Thr
        115                120                125

Gly Asn Glu Leu Ser Thr Lys Glu Gln Ile Ser Arg Asn Ser Lys Ala
    130                135                140

Leu Glu Glu Lys Tyr Val Ala Glu Leu Gln Leu Glu Arg Leu Lys Lys
145                150                155                160

Asp Gly Glu Val Arg Gly Ser Ile Asn Arg Phe Lys Thr Ser Asp Tyr
                165                170                175

Val Lys Glu Ala Lys Gln Leu Leu Lys Val Gln Lys Ala Tyr His Gln
            180                185                190

Leu Asp Gln Ser Phe Ile Asp Thr Tyr Ile Asp Leu Leu Glu Thr Arg
            195                200                205

Arg Thr Tyr Tyr Glu Gly Pro Gly Glu Gly Ser Pro Phe Gly Trp Lys
        210                215                220

Asp Ile Lys Glu Trp Tyr Glu Met Leu Met Gly His Cys Thr Tyr Phe
225                230                235                240

Pro Glu Glu Leu Arg Ser Val Lys Tyr Ala Tyr Asn Ala Asp Leu Tyr
                245                250                255

Asn Ala Leu Asn Asp Leu Asn Asn Leu Val Ile Thr Arg Asp Glu Asn
            260                265                270

-continued

```
Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
        290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
                340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
        370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
        450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
        530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
        580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
        610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
```

-continued

```
            690             695             700

Ala Leu Ile Ile Ala Asn Ala Asp Phe Ile Phe Lys Glu Trp Lys Lys
705             710             715             720

Leu Asp Lys Ala Lys Lys Val Met Glu Asn Gln Met Phe Glu Glu Lys
            725             730             735

Gln Ala Glu Ser Met Pro Glu Ile Glu Thr Glu Gln Glu Tyr Lys Glu
            740             745             750

Ile Phe Ile Thr Pro His Gln Ile Lys His Ile Lys Asp Phe Lys Asp
            755             760             765

Tyr Lys Tyr Ser His Arg Val Asp Lys Lys Pro Asn Arg Glu Leu Ile
            770             775             780

Asn Asp Thr Leu Tyr Ser Thr Arg Lys Asp Asp Lys Gly Asn Thr Leu
785             790             795             800

Ile Val Asn Asn Leu Asn Gly Leu Tyr Asp Lys Asp Asn Asp Lys Leu
            805             810             815

Lys Lys Leu Ile Asn Lys Ser Pro Glu Lys Leu Leu Met Tyr His His
            820             825             830

Asp Pro Gln Thr Tyr Gln Lys Leu Lys Leu Ile Met Glu Gln Tyr Gly
            835             840             845

Asp Glu Lys Asn Pro Leu Tyr Lys Tyr Tyr Glu Glu Thr Gly Asn Tyr
            850             855             860

Leu Thr Lys Tyr Ser Lys Lys Asp Asn Gly Pro Val Ile Lys Lys Ile
865             870             875             880

Lys Tyr Tyr Gly Asn Lys Leu Asn Ala His Leu Asp Ile Thr Asp Asp
            885             890             895

Tyr Pro Asn Ser Arg Asn Lys Val Val Lys Leu Ser Leu Lys Pro Tyr
            900             905             910

Arg Phe Asp Val Tyr Leu Asp Asn Gly Val Tyr Lys Phe Val Thr Val
            915             920             925

Lys Asn Leu Asp Val Ile Lys Lys Glu Asn Tyr Tyr Glu Val Asn Ser
            930             935             940

Lys Cys Tyr Glu Glu Ala Lys Lys Leu Lys Lys Ile Ser Asn Gln Ala
945             950             955             960

Glu Phe Ile Ala Ser Phe Tyr Asn Asn Asp Leu Ile Lys Ile Asn Gly
            965             970             975

Glu Leu Tyr Arg Val Ile Gly Val Asn Asn Asp Leu Leu Asn Arg Ile
            980             985             990

Glu Val Asn Met Ile Asp Ile Thr  Tyr Arg Glu Tyr Leu  Glu Asn Met
            995             1000            1005

Asn Asp  Lys Arg Pro Pro Arg  Ile Ile Lys Thr Ile  Ala Ser Lys
    1010            1015            1020

Thr Gln  Ser Ile Lys Lys Tyr  Ser Thr Asp Ile Leu  Gly Asn Leu
    1025            1030            1035

Tyr Glu  Val Lys Ser Lys Lys  His Pro Gln Ile Ile  Lys Lys Gly
    1040            1045            1050
```

```
<210> SEQ ID NO 41
<211> LENGTH: 984
<212> TYPE: PRT
<213> ORGANISM: Campylobacter jejuni

<400> SEQUENCE: 41

Met Ala Arg Ile Leu Ala Phe Asp Ile Gly Ile Ser Ser Ile Gly Trp
1               5               10              15
```

```
Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg
            35                  40                  45

Arg Leu Ala Arg Ser Ala Arg Lys Arg Leu Ala Arg Arg Lys Ala Arg
        50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
                100                 105                 110

Leu Ser Lys Gln Asp Phe Ala Arg Val Ile Leu His Ile Ala Lys Arg
            115                 120                 125

Arg Gly Tyr Asp Asp Ile Lys Asn Ser Asp Asp Lys Glu Lys Gly Ala
        130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
            195                 200                 205

Lys Lys Gln Arg Glu Phe Gly Phe Ser Phe Ser Lys Lys Phe Glu Glu
            210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
            275                 280                 285

Asp Asp Leu Asn Ala Leu Leu Asn Glu Val Leu Lys Asn Gly Thr Leu
        290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
            355                 360                 365

Lys Lys Ala Leu Ala Lys Tyr Asp Leu Asn Gln Asn Gln Ile Asp Ser
        370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
```

-continued

```
            435                 440                 445
Asn Pro Val Val Leu Arg Ala Ile Lys Glu Tyr Arg Lys Val Leu Asn
    450                 455                 460
Ala Leu Leu Lys Lys Tyr Gly Lys Val His Lys Ile Asn Ile Glu Leu
465                 470                 475                 480
Ala Arg Glu Val Gly Lys Asn His Ser Gln Arg Ala Lys Ile Glu Lys
                485                 490                 495
Glu Gln Asn Glu Asn Tyr Lys Ala Lys Lys Asp Ala Glu Leu Glu Cys
                500                 505                 510
Glu Lys Leu Gly Leu Lys Ile Asn Ser Lys Asn Ile Leu Lys Leu Arg
            515                 520                 525
Leu Phe Lys Glu Gln Lys Glu Phe Cys Ala Tyr Ser Gly Glu Lys Ile
    530                 535                 540
Lys Ile Ser Asp Leu Gln Asp Glu Lys Met Leu Glu Ile Asp His Ile
545                 550                 555                 560
Tyr Pro Tyr Ser Arg Ser Phe Asp Asp Ser Tyr Met Asn Lys Val Leu
                565                 570                 575
Val Phe Thr Lys Gln Asn Gln Glu Lys Leu Asn Gln Thr Pro Phe Glu
                580                 585                 590
Ala Phe Gly Asn Asp Ser Ala Lys Trp Gln Lys Ile Glu Val Leu Ala
            595                 600                 605
Lys Asn Leu Pro Thr Lys Lys Gln Lys Arg Ile Leu Asp Lys Asn Tyr
    610                 615                 620
Lys Asp Lys Glu Gln Lys Asn Phe Lys Asp Arg Asn Leu Asn Asp Thr
625                 630                 635                 640
Arg Tyr Ile Ala Arg Leu Val Leu Asn Tyr Thr Lys Asp Tyr Leu Asp
                645                 650                 655
Phe Leu Pro Leu Ser Asp Asp Glu Asn Thr Lys Leu Asn Asp Thr Gln
            660                 665                 670
Lys Gly Ser Lys Val His Val Glu Ala Lys Ser Gly Met Leu Thr Ser
            675                 680                 685
Ala Leu Arg His Thr Trp Gly Phe Ser Ala Lys Asp Arg Asn Asn His
    690                 695                 700
Leu His His Ala Ile Asp Ala Val Ile Ile Ala Tyr Ala Asn Asn Ser
705                 710                 715                 720
Ile Val Lys Ala Phe Ser Asp Phe Lys Lys Glu Gln Glu Ser Asn Ser
                725                 730                 735
Ala Glu Leu Tyr Ala Lys Lys Ile Ser Glu Leu Asp Tyr Lys Asn Lys
                740                 745                 750
Arg Lys Phe Phe Glu Pro Phe Ser Gly Phe Arg Gln Lys Val Leu Asp
            755                 760                 765
Lys Ile Asp Glu Ile Phe Val Ser Lys Pro Glu Arg Lys Lys Pro Ser
    770                 775                 780
Gly Ala Leu His Glu Glu Thr Phe Arg Lys Glu Glu Glu Phe Tyr Gln
785                 790                 795                 800
Ser Tyr Gly Gly Lys Glu Gly Val Leu Lys Ala Leu Glu Leu Gly Lys
                805                 810                 815
Ile Arg Lys Val Asn Gly Lys Ile Val Lys Asn Gly Asp Met Phe Arg
                820                 825                 830
Val Asp Ile Phe Lys His Lys Lys Thr Asn Lys Phe Tyr Ala Val Pro
            835                 840                 845
Ile Tyr Thr Met Asp Phe Ala Leu Lys Val Leu Pro Asn Lys Ala Val
    850                 855                 860
```

-continued

```
Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
            900                 905                 910

Thr Ser Ser Thr Val Ser Leu Ile Val Ser Lys His Asp Asn Lys Phe
            915                 920                 925

Glu Thr Leu Ser Lys Asn Gln Lys Ile Leu Phe Lys Asn Ala Asn Glu
        930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys
            980

<210> SEQ ID NO 42
<211> LENGTH: 1629
<212> TYPE: PRT
<213> ORGANISM: Francisella novicida

<400> SEQUENCE: 42

Met Asn Phe Lys Ile Leu Pro Ile Ala Ile Asp Leu Gly Val Lys Asn
1               5                   10                  15

Thr Gly Val Phe Ser Ala Phe Tyr Gln Lys Gly Thr Ser Leu Glu Arg
                20                  25                  30

Leu Asp Asn Lys Asn Gly Lys Val Tyr Glu Leu Ser Lys Asp Ser Tyr
            35                  40                  45

Thr Leu Leu Met Asn Asn Arg Thr Ala Arg Arg His Gln Arg Arg Gly
        50                  55                  60

Ile Asp Arg Lys Gln Leu Val Lys Arg Leu Phe Lys Leu Ile Trp Thr
65                  70                  75                  80

Glu Gln Leu Asn Leu Glu Trp Asp Lys Asp Thr Gln Gln Ala Ile Ser
                85                  90                  95

Phe Leu Phe Asn Arg Arg Gly Phe Ser Phe Ile Thr Asp Gly Tyr Ser
                100                 105                 110

Pro Glu Tyr Leu Asn Ile Val Pro Glu Gln Val Lys Ala Ile Leu Met
            115                 120                 125

Asp Ile Phe Asp Asp Tyr Asn Gly Glu Asp Asp Leu Asp Ser Tyr Leu
        130                 135                 140

Lys Leu Ala Thr Glu Gln Glu Ser Lys Ile Ser Glu Ile Tyr Asn Lys
145                 150                 155                 160

Leu Met Gln Lys Ile Leu Glu Phe Lys Leu Met Lys Leu Cys Thr Asp
                165                 170                 175

Ile Lys Asp Asp Lys Val Ser Thr Lys Thr Leu Lys Glu Ile Thr Ser
            180                 185                 190

Tyr Glu Phe Glu Leu Leu Ala Asp Tyr Leu Ala Asn Tyr Ser Glu Ser
            195                 200                 205

Leu Lys Thr Gln Lys Phe Ser Tyr Thr Asp Lys Gln Gly Asn Leu Lys
        210                 215                 220

Glu Leu Ser Tyr Tyr His His Asp Lys Tyr Asn Ile Gln Glu Phe Leu
225                 230                 235                 240

Lys Arg His Ala Thr Ile Asn Asp Arg Ile Leu Asp Thr Leu Leu Thr
```

```
                    245             250             255

Asp Asp Leu Asp Ile Trp Asn Phe Asn Phe Glu Lys Phe Asp Phe Asp
            260             265             270

Lys Asn Glu Glu Lys Leu Gln Asn Gln Glu Asp Lys Asp His Ile Gln
        275             280             285

Ala His Leu His His Phe Val Phe Ala Val Asn Lys Ile Lys Ser Glu
    290             295             300

Met Ala Ser Gly Gly Arg His Arg Ser Gln Tyr Phe Gln Glu Ile Thr
305             310             315             320

Asn Val Leu Asp Glu Asn Asn His Gln Glu Gly Tyr Leu Lys Asn Phe
            325             330             335

Cys Glu Asn Leu His Asn Lys Lys Tyr Ser Asn Leu Ser Val Lys Asn
            340             345             350

Leu Val Asn Leu Ile Gly Asn Leu Ser Asn Leu Glu Leu Lys Pro Leu
            355             360             365

Arg Lys Tyr Phe Asn Asp Lys Ile His Ala Lys Ala Asp His Trp Asp
    370             375             380

Glu Gln Lys Phe Thr Glu Thr Tyr Cys His Trp Ile Leu Gly Glu Trp
385             390             395             400

Arg Val Gly Val Lys Asp Gln Asp Lys Lys Asp Gly Ala Lys Tyr Ser
            405             410             415

Tyr Lys Asp Leu Cys Asn Glu Leu Lys Gln Lys Val Thr Lys Ala Gly
            420             425             430

Leu Val Asp Phe Leu Leu Glu Leu Asp Pro Cys Arg Thr Ile Pro Pro
            435             440             445

Tyr Leu Asp Asn Asn Asn Arg Lys Pro Pro Lys Cys Gln Ser Leu Ile
    450             455             460

Leu Asn Pro Lys Phe Leu Asp Asn Gln Tyr Pro Asn Trp Gln Gln Tyr
465             470             475             480

Leu Gln Glu Leu Lys Lys Leu Gln Ser Ile Gln Asn Tyr Leu Asp Ser
            485             490             495

Phe Glu Thr Asp Leu Lys Val Leu Lys Ser Ser Lys Asp Gln Pro Tyr
            500             505             510

Phe Val Glu Tyr Lys Ser Ser Asn Gln Gln Ile Ala Ser Gly Gln Arg
            515             520             525

Asp Tyr Lys Asp Leu Asp Ala Arg Ile Leu Gln Phe Ile Phe Asp Arg
    530             535             540

Val Lys Ala Ser Asp Glu Leu Leu Leu Asn Glu Ile Tyr Phe Gln Ala
545             550             555             560

Lys Lys Leu Lys Gln Lys Ala Ser Ser Glu Leu Glu Lys Leu Glu Ser
            565             570             575

Ser Lys Lys Leu Asp Glu Val Ile Ala Asn Ser Gln Leu Ser Gln Ile
            580             585             590

Leu Lys Ser Gln His Thr Asn Gly Ile Phe Glu Gln Gly Thr Phe Leu
            595             600             605

His Leu Val Cys Lys Tyr Tyr Lys Gln Arg Gln Arg Ala Arg Asp Ser
    610             615             620

Arg Leu Tyr Ile Met Pro Glu Tyr Arg Tyr Asp Lys Lys Leu His Lys
625             630             635             640

Tyr Asn Asn Thr Gly Arg Phe Asp Asp Asp Asn Gln Leu Leu Thr Tyr
            645             650             655

Cys Asn His Lys Pro Arg Gln Lys Arg Tyr Gln Leu Leu Asn Asp Leu
            660             665             670
```

```
Ala Gly Val Leu Gln Val Ser Pro Asn Phe Leu Lys Asp Lys Ile Gly
        675             680             685

Ser Asp Asp Asp Leu Phe Ile Ser Lys Trp Leu Val Glu His Ile Arg
    690             695             700

Gly Phe Lys Lys Ala Cys Glu Asp Ser Leu Lys Ile Gln Lys Asp Asn
705             710             715             720

Arg Gly Leu Leu Asn His Lys Ile Asn Ile Ala Arg Asn Thr Lys Gly
            725             730             735

Lys Cys Glu Lys Glu Ile Phe Asn Leu Ile Cys Lys Ile Glu Gly Ser
            740             745             750

Glu Asp Lys Lys Gly Asn Tyr Lys His Gly Leu Ala Tyr Glu Leu Gly
            755             760             765

Val Leu Leu Phe Gly Glu Pro Asn Glu Ala Ser Lys Pro Glu Phe Asp
    770             775             780

Arg Lys Ile Lys Lys Phe Asn Ser Ile Tyr Ser Phe Ala Gln Ile Gln
785             790             795             800

Gln Ile Ala Phe Ala Glu Arg Lys Gly Asn Ala Asn Thr Cys Ala Val
            805             810             815

Cys Ser Ala Asp Asn Ala His Arg Met Gln Gln Ile Lys Ile Thr Glu
            820             825             830

Pro Val Glu Asp Asn Lys Asp Lys Ile Ile Leu Ser Ala Lys Ala Gln
            835             840             845

Arg Leu Pro Ala Ile Pro Thr Arg Ile Val Asp Gly Ala Val Lys Lys
    850             855             860

Met Ala Thr Ile Leu Ala Lys Asn Ile Val Asp Asp Asn Trp Gln Asn
865             870             875             880

Ile Lys Gln Val Leu Ser Ala Lys His Gln Leu His Ile Pro Ile Ile
            885             890             895

Thr Glu Ser Asn Ala Phe Glu Phe Glu Pro Ala Leu Ala Asp Val Lys
            900             905             910

Gly Lys Ser Leu Lys Asp Arg Arg Lys Lys Ala Leu Glu Arg Ile Ser
            915             920             925

Pro Glu Asn Ile Phe Lys Asp Lys Asn Asn Arg Ile Lys Glu Phe Ala
    930             935             940

Lys Gly Ile Ser Ala Tyr Ser Gly Ala Asn Leu Thr Asp Gly Asp Phe
945             950             955             960

Asp Gly Ala Lys Glu Glu Leu Asp His Ile Ile Pro Arg Ser His Lys
            965             970             975

Lys Tyr Gly Thr Leu Asn Asp Glu Ala Asn Leu Ile Cys Val Thr Arg
            980             985             990

Gly Asp Asn Lys Asn Lys Gly Asn  Arg Ile Phe Cys Leu  Arg Asp Leu
            995             1000             1005

Ala Asp  Asn Tyr Lys Leu Lys  Gln Phe Glu Thr Thr  Asp Asp Leu
    1010             1015             1020

Glu Ile  Glu Lys Lys Ile Ala  Asp Thr Ile Trp Asp  Ala Asn Lys
    1025             1030             1035

Lys Asp  Phe Lys Phe Gly Asn  Tyr Arg Ser Phe Ile  Asn Leu Thr
    1040             1045             1050

Pro Gln  Glu Gln Lys Ala Phe  Arg His Ala Leu Phe  Leu Ala Asp
    1055             1060             1065

Glu Asn  Pro Ile Lys Gln Ala  Val Ile Arg Ala Ile  Asn Asn Arg
    1070             1075             1080
```

-continued

```
Asn Arg Thr Phe Val Asn Gly  Thr Gln Arg Tyr Phe  Ala Glu Val
    1085             1090             1095

Leu Ala Asn Asn Ile Tyr Leu  Arg Ala Lys Lys Glu  Asn Leu Asn
    1100             1105             1110

Thr Asp Lys Ile Ser Phe Asp  Tyr Phe Gly Ile Pro  Thr Ile Gly
    1115             1120             1125

Asn Gly Arg Gly Ile Ala Glu  Ile Arg Gln Leu Tyr  Glu Lys Val
    1130             1135             1140

Asp Ser Asp Ile Gln Ala Tyr  Ala Lys Gly Asp Lys  Pro Gln Ala
    1145             1150             1155

Ser Tyr Ser His Leu Ile Asp  Ala Met Leu Ala Phe  Cys Ile Ala
    1160             1165             1170

Ala Asp Glu His Arg Asn Asp  Gly Ser Ile Gly Leu  Glu Ile Asp
    1175             1180             1185

Lys Asn Tyr Ser Leu Tyr Pro  Leu Asp Lys Asn Thr  Gly Glu Val
    1190             1195             1200

Phe Thr Lys Asp Ile Phe Ser  Gln Ile Lys Ile Thr  Asp Asn Glu
    1205             1210             1215

Phe Ser Asp Lys Lys Leu Val  Arg Lys Lys Ala Ile  Glu Gly Phe
    1220             1225             1230

Asn Thr His Arg Gln Met Thr  Arg Asp Gly Ile Tyr  Ala Glu Asn
    1235             1240             1245

Tyr Leu Pro Ile Leu Ile His  Lys Glu Leu Asn Glu  Val Arg Lys
    1250             1255             1260

Gly Tyr Thr Trp Lys Asn Ser  Glu Glu Ile Lys Ile  Phe Lys Gly
    1265             1270             1275

Lys Lys Tyr Asp Ile Gln Gln  Leu Asn Asn Leu Val  Tyr Cys Leu
    1280             1285             1290

Lys Phe Val Asp Lys Pro Ile  Ser Ile Asp Ile Gln  Ile Ser Thr
    1295             1300             1305

Leu Glu Glu Leu Arg Asn Ile  Leu Thr Thr Asn Asn  Ile Ala Ala
    1310             1315             1320

Thr Ala Glu Tyr Tyr Tyr Ile  Asn Leu Lys Thr Gln  Lys Leu His
    1325             1330             1335

Glu Tyr Tyr Ile Glu Asn Tyr  Asn Thr Ala Leu Gly  Tyr Lys Lys
    1340             1345             1350

Tyr Ser Lys Glu Met Glu Phe  Leu Arg Ser Leu Ala  Tyr Arg Ser
    1355             1360             1365

Glu Arg Val Lys Ile Lys Ser  Ile Asp Asp Val Lys  Gln Val Leu
    1370             1375             1380

Asp Lys Asp Ser Asn Phe Ile  Ile Gly Lys Ile Thr  Leu Pro Phe
    1385             1390             1395

Lys Lys Glu Trp Gln Arg Leu  Tyr Arg Glu Trp Gln  Asn Thr Thr
    1400             1405             1410

Ile Lys Asp Asp Tyr Glu Phe  Leu Lys Ser Phe Phe  Asn Val Lys
    1415             1420             1425

Ser Ile Thr Lys Leu His Lys  Lys Val Arg Lys Asp  Phe Ser Leu
    1430             1435             1440

Pro Ile Ser Thr Asn Glu Gly  Lys Phe Leu Val Lys  Arg Lys Thr
    1445             1450             1455

Trp Asp Asn Asn Phe Ile Tyr  Gln Ile Leu Asn Asp  Ser Asp Ser
    1460             1465             1470

Arg Ala Asp Gly Thr Lys Pro  Phe Ile Pro Ala Phe  Asp Ile Ser
```

-continued

```
         1475                1480                1485

Lys Asn  Glu Ile Val Glu Ala  Ile Ile Asp Ser Phe  Thr Ser Lys
    1490                1495                1500

Asn Ile  Phe Trp Leu Pro Lys  Asn Ile Glu Leu Gln  Lys Val Asp
    1505                1510                1515

Asn Lys  Asn Ile Phe Ala Ile  Asp Thr Ser Lys Trp  Phe Glu Val
    1520                1525                1530

Glu Thr  Pro Ser Asp Leu Arg  Asp Ile Gly Ile Ala  Thr Ile Gln
    1535                1540                1545

Tyr Lys  Ile Asp Asn Asn Ser  Arg Pro Lys Val Arg  Val Lys Leu
    1550                1555                1560

Asp Tyr  Val Ile Asp Asp Asp  Ser Lys Ile Asn Tyr  Phe Met Asn
    1565                1570                1575

His Ser  Leu Leu Lys Ser Arg  Tyr Pro Asp Lys Val  Leu Glu Ile
    1580                1585                1590

Leu Lys  Gln Ser Thr Ile Ile  Glu Phe Glu Ser Ser  Gly Phe Asn
    1595                1600                1605

Lys Thr  Ile Lys Glu Met Leu  Gly Met Lys Leu Ala  Gly Ile Tyr
    1610                1615                1620

Asn Glu  Thr Ser Asn Asn
    1625

<210> SEQ ID NO 43
<211> LENGTH: 1082
<212> TYPE: PRT
<213> ORGANISM: Neisseria meningitides

<400> SEQUENCE: 43

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205
```

```
Gln Ala Glu Leu Ile Leu Leu Phe Glu Lys Gln Lys Glu Phe Gly Asn
    210             215             220

Pro His Val Ser Gly Gly Leu Lys Glu Gly Ile Glu Thr Leu Leu Met
225             230             235             240

Thr Gln Arg Pro Ala Leu Ser Gly Asp Ala Val Gln Lys Met Leu Gly
            245             250             255

His Cys Thr Phe Glu Pro Ala Glu Pro Lys Ala Ala Lys Asn Thr Tyr
            260             265             270

Thr Ala Glu Arg Phe Ile Trp Leu Thr Lys Leu Asn Asn Leu Arg Ile
        275             280             285

Leu Glu Gln Gly Ser Glu Arg Pro Leu Thr Asp Thr Glu Arg Ala Thr
    290             295             300

Leu Met Asp Glu Pro Tyr Arg Lys Ser Lys Leu Thr Tyr Ala Gln Ala
305             310             315             320

Arg Lys Leu Leu Gly Leu Glu Asp Thr Ala Phe Phe Lys Gly Leu Arg
            325             330             335

Tyr Gly Lys Asp Asn Ala Glu Ala Ser Thr Leu Met Glu Met Lys Ala
        340             345             350

Tyr His Ala Ile Ser Arg Ala Leu Glu Lys Glu Gly Leu Lys Asp Lys
        355             360             365

Lys Ser Pro Leu Asn Leu Ser Pro Glu Leu Gln Asp Glu Ile Gly Thr
    370             375             380

Ala Phe Ser Leu Phe Lys Thr Asp Glu Asp Ile Thr Gly Arg Leu Lys
385             390             395             400

Asp Arg Ile Gln Pro Glu Ile Leu Glu Ala Leu Leu Lys His Ile Ser
            405             410             415

Phe Asp Lys Phe Val Gln Ile Ser Leu Lys Ala Leu Arg Arg Ile Val
            420             425             430

Pro Leu Met Glu Gln Gly Lys Arg Tyr Asp Glu Ala Cys Ala Glu Ile
        435             440             445

Tyr Gly Asp His Tyr Gly Lys Lys Asn Thr Glu Glu Lys Ile Tyr Leu
    450             455             460

Pro Pro Ile Pro Ala Asp Glu Ile Arg Asn Pro Val Val Leu Arg Ala
465             470             475             480

Leu Ser Gln Ala Arg Lys Val Ile Asn Gly Val Val Arg Arg Tyr Gly
            485             490             495

Ser Pro Ala Arg Ile His Ile Glu Thr Ala Arg Glu Val Gly Lys Ser
            500             505             510

Phe Lys Asp Arg Lys Glu Ile Glu Lys Arg Gln Glu Glu Asn Arg Lys
            515             520             525

Asp Arg Glu Lys Ala Ala Ala Lys Phe Arg Glu Tyr Phe Pro Asn Phe
    530             535             540

Val Gly Glu Pro Lys Ser Lys Asp Ile Leu Lys Leu Arg Leu Tyr Glu
545             550             555             560

Gln Gln His Gly Lys Cys Leu Tyr Ser Gly Lys Glu Ile Asn Leu Gly
            565             570             575

Arg Leu Asn Glu Lys Gly Tyr Val Glu Ile Asp His Ala Leu Pro Phe
            580             585             590

Ser Arg Thr Trp Asp Asp Ser Phe Asn Asn Lys Val Leu Val Leu Gly
            595             600             605

Ser Glu Asn Gln Asn Lys Gly Asn Gln Thr Pro Tyr Glu Tyr Phe Asn
    610             615             620

Gly Lys Asp Asn Ser Arg Glu Trp Gln Glu Phe Lys Ala Arg Val Glu
```

```
625                    630                    635                    640

Thr Ser Arg Phe Pro Arg Ser Lys Lys Gln Arg Ile Leu Leu Gln Lys
                645                    650                    655

Phe Asp Glu Asp Gly Phe Lys Glu Arg Asn Leu Asn Asp Thr Arg Tyr
                660                    665                    670

Val Asn Arg Phe Leu Cys Gln Phe Val Ala Asp Arg Met Arg Leu Thr
            675                    680                    685

Gly Lys Gly Lys Lys Arg Val Phe Ala Ser Asn Gly Gln Ile Thr Asn
        690                    695                    700

Leu Leu Arg Gly Phe Trp Gly Leu Arg Lys Val Arg Ala Glu Asn Asp
705                    710                    715                    720

Arg His His Ala Leu Asp Ala Val Val Ala Cys Ser Thr Val Ala
                725                    730                    735

Met Gln Gln Lys Ile Thr Arg Phe Val Arg Tyr Lys Glu Met Asn Ala
                740                    745                    750

Phe Asp Gly Lys Thr Ile Asp Lys Glu Thr Gly Glu Val Leu His Gln
            755                    760                    765

Lys Thr His Phe Pro Gln Pro Trp Glu Phe Phe Ala Gln Glu Val Met
        770                    775                    780

Ile Arg Val Phe Gly Lys Pro Asp Gly Lys Pro Glu Phe Glu Glu Ala
785                    790                    795                    800

Asp Thr Pro Glu Lys Leu Arg Thr Leu Leu Ala Glu Lys Leu Ser Ser
                805                    810                    815

Arg Pro Glu Ala Val His Glu Tyr Val Thr Pro Leu Phe Val Ser Arg
                820                    825                    830

Ala Pro Asn Arg Lys Met Ser Gly Gln Gly His Met Glu Thr Val Lys
            835                    840                    845

Ser Ala Lys Arg Leu Asp Glu Gly Val Ser Val Leu Arg Val Pro Leu
        850                    855                    860

Thr Gln Leu Lys Leu Lys Asp Leu Glu Lys Met Val Asn Arg Glu Arg
865                    870                    875                    880

Glu Pro Lys Leu Tyr Glu Ala Leu Lys Ala Arg Leu Glu Ala His Lys
                885                    890                    895

Asp Asp Pro Ala Lys Ala Phe Ala Glu Pro Phe Tyr Lys Tyr Asp Lys
            900                    905                    910

Ala Gly Asn Arg Thr Gln Gln Val Lys Ala Val Arg Val Glu Gln Val
            915                    920                    925

Gln Lys Thr Gly Val Trp Val Arg Asn His Asn Gly Ile Ala Asp Asn
        930                    935                    940

Ala Thr Met Val Arg Val Asp Val Phe Glu Lys Gly Asp Lys Tyr Tyr
945                    950                    955                    960

Leu Val Pro Ile Tyr Ser Trp Gln Val Ala Lys Gly Ile Leu Pro Asp
            965                    970                    975

Arg Ala Val Val Gln Gly Lys Asp Glu Glu Asp Trp Gln Leu Ile Asp
            980                    985                    990

Asp Ser Phe Asn Phe Lys Phe Ser Leu His Pro Asn Asp Leu Val Glu
        995                    1000                   1005

Val Ile Thr Lys Lys Ala Arg Met Phe Gly Tyr Phe Ala Ser Cys
    1010                   1015                   1020

His Arg Gly Thr Gly Asn Ile Asn Ile Arg Ile His Asp Leu Asp
    1025                   1030                   1035

His Lys Ile Gly Lys Asn Gly Ile Leu Glu Gly Ile Gly Val Lys
    1040                   1045                   1050
```

Thr Ala  Leu Ser Phe Gln Lys  Tyr Gln Ile Asp Glu  Leu Gly Lys
    1055                1060                1065

Glu Ile  Arg Pro Cys Arg Leu  Lys Lys Arg Pro Pro  Val Arg
    1070                1075                1080

<210> SEQ ID NO 44
<211> LENGTH: 14
<212> TYPE: PRT
<213> ORGANISM: artificial
<220> FEATURE:
<223> OTHER INFORMATION: V5 Tag 14 amino acids

<400> SEQUENCE: 44

Gly Lys Pro Ile Pro Asn Pro Leu Leu Gly Leu Asp Ser Thr
1               5               10

<210> SEQ ID NO 45
<211> LENGTH: 9
<212> TYPE: PRT
<213> ORGANISM: artificial
<220> FEATURE:
<223> OTHER INFORMATION: V5 Tag 9 amino acids

<400> SEQUENCE: 45

Ile Pro Asn Pro Leu Leu Gly Leu Asp
1               5

<210> SEQ ID NO 46
<211> LENGTH: 385
<212> TYPE: PRT
<213> ORGANISM: Oryza sativa

<400> SEQUENCE: 46

Met Ala Glu Ala Gly Val Ala Ala Ala Ser Leu Phe Gly Ala Asp Arg
1               5               10              15

Arg Leu Cys Ser Ala Asp Ile Leu Pro Pro Ala Glu Val Arg Ala Arg
            20              25              30

Ile Glu Val Ala Val Leu Asn Phe Leu Ala Ala Leu Thr Asp Pro Ala
        35              40              45

Ala Pro Ala Ile Ser Ala Leu Pro Leu Ile Ser Arg Gly Ala Ala Asn
    50              55              60

Arg Gly Leu Arg Arg Ala Leu Leu Arg Asp Asp Val Ser Ser Val Tyr
65              70              75              80

Leu Ser Tyr Ala Ser Cys Lys Arg Ser Leu Thr Arg Ala Asn Asp Ala
            85              90              95

Lys Ala Phe Val Arg Val Trp Lys Val Met Glu Met Cys Tyr Lys Ile
            100             105             110

Leu Gly Glu Gly Lys Leu Val Thr Leu Arg Glu Leu Phe Tyr Thr Leu
        115             120             125

Leu Ser Glu Ser Pro Thr Tyr Phe Thr Cys Gln Arg His Val Asn Gln
    130             135             140

Thr Val Gln Asp Val Val Ser Leu Leu Arg Cys Thr Arg Gln Ser Leu
145             150             155             160

Gly Ile Met Ala Ser Ser Arg Gly Ala Leu Ile Gly Arg Leu Val Val
            165             170             175

Gln Gly Pro Glu Glu Glu His Val Asp Cys Ser Ile Leu Gly Pro Ser
        180             185             190

Gly His Ala Ile Thr Gly Asp Leu Asn Val Leu Ser Lys Leu Ile Phe
        195             200             205

-continued

```
Ser Ser Asp Ala Arg Tyr Ile Ile Val Val Glu Lys Asp Ala Ile Phe
    210                 215                 220

Gln Arg Leu Ala Glu Asp Arg Ile Tyr Ser His Leu Pro Cys Ile Leu
225                 230                 235                 240

Ile Thr Ala Lys Gly Tyr Pro Asp Leu Ala Thr Arg Phe Ile Leu His
                245                 250                 255

Arg Leu Ser Gln Thr Tyr Pro Asn Met Pro Ile Phe Ala Leu Val Asp
                260                 265                 270

Trp Asn Pro Ala Gly Leu Ala Ile Leu Cys Thr Tyr Lys Tyr Gly Ser
                275                 280                 285

Ile Ser Met Gly Leu Glu Ser Tyr Arg Tyr Ala Cys Asn Val Lys Trp
    290                 295                 300

Leu Gly Leu Arg Gly Asp Asp Leu Gln Leu Ile Pro Gln Ser Ala Tyr
305                 310                 315                 320

Gln Glu Leu Lys Pro Arg Asp Leu Gln Ile Ala Lys Ser Leu Leu Ser
                325                 330                 335

Ser Lys Phe Leu Gln Asp Lys His Arg Ala Glu Leu Thr Leu Met Leu
                340                 345                 350

Glu Thr Gly Lys Arg Ala Glu Ile Glu Ala Leu Tyr Ser His Gly Phe
                355                 360                 365

Asp Phe Leu Gly Lys Tyr Val Ala Arg Lys Ile Val Gln Gly Asp Tyr
    370                 375                 380

Ile
385
```

<210> SEQ ID NO 47
<211> LENGTH: 383
<212> TYPE: PRT
<213> ORGANISM: Zea mays

<400> SEQUENCE: 47

```
Met Ala Gly Arg Asp Lys Arg Arg Arg Ala Ala Pro Leu Glu Gly Asp
1               5                   10                  15

Glu Gln Gln Leu Arg Arg Arg Leu Glu Glu Ala Ala Leu Leu Leu Arg
                20                  25                  30

Arg Ile Lys Gly Leu Val Arg Trp Ile Val Glu Glu Val Ala Ala Gly
        35                  40                  45

Arg Ser Pro Ser Ile Val Leu His Arg Tyr Arg Asn Tyr Cys Ser Ser
    50                  55                  60

Ala Asp Ser Ala Ser Pro Ser Pro Cys Ala Cys Ser Tyr Asp Ile Pro
65                  70                  75                  80

Val Gly Thr Asp Val Leu Ser Leu Leu His Lys Asp Tyr His Thr Ser
                85                  90                  95

Arg Leu Asn Val Leu Leu Arg Val Leu Phe Val Val Gln Gln Leu Leu
                100                 105                 110

Gln Gln Asn Lys His Cys Ser Lys Arg Asp Ile Tyr Tyr Met Tyr Pro
            115                 120                 125

Ser Ile Phe Val Glu Val Ala Val Val Asp Arg Ala Ile Asn Asp Ile
    130                 135                 140

Cys Ile Leu Phe Lys Cys Ser Arg His Asn Leu Asn Val Val Pro Val
145                 150                 155                 160

Val Lys Gly Leu Val Met Gly Trp Ile Arg Phe Met Glu Gly Glu Lys
                165                 170                 175

Lys Val Tyr Cys Ile Thr Ser Val Asn Ala Ala Phe Ser Ile Pro Val
```

```
            180             185             190

Asp Ile Glu Ala Ile Lys Asp Val Val Ser Val Ala His Tyr Ile Leu
        195             200             205

Val Val Glu Lys Glu Thr Val Phe Gln Arg Leu Ala Asn Asp Lys Phe
        210             215             220

Cys Glu Arg Asn Arg Cys Ile Val Ile Thr Gly Arg Gly Tyr Pro Asp
225             230             235             240

Ile Pro Thr Arg Arg Phe Leu Arg Tyr Leu Val Glu Leu Leu His Leu
            245             250             255

Pro Ala Tyr Cys Leu Val Asp Ser Asp Pro Tyr Gly Phe Asp Ile Leu
            260             265             270

Ala Thr Tyr Lys Phe Gly Ser Leu Gln Leu Ala His Asp Ala Asn Leu
            275             280             285

Leu Arg Val Pro Asp Ile Arg Trp Leu Gly Val Phe Thr Ser Asp Phe
            290             295             300

Glu Glu Tyr Cys Leu Pro Asp Cys Cys Leu Leu Arg Leu Ser Pro Glu
305             310             315             320

Asp Arg Arg Lys Ala Glu Gly Ile Leu Ala Arg Cys Tyr Leu His Arg
            325             330             335

Glu Ala Pro Glu Trp Arg Ser Glu Leu Glu Ala Met Leu Gln Lys Gly
            340             345             350

Val Lys Phe Glu Ile Glu Ala Leu Ser Ala Asn Ser Ile Ser Phe Leu
            355             360             365

Ser Asp Glu Tyr Ile Pro Gln Lys Ile Lys Gln Gly Met His Leu
        370             375             380

<210> SEQ ID NO 48
<211> LENGTH: 382
<212> TYPE: PRT
<213> ORGANISM: Zea mays

<400> SEQUENCE: 48

Met Ala Glu Ala Asn Val Ala Ala Ala Ser Leu Phe Gly Ala Asp Arg
1               5               10              15

Arg Leu Cys Ser Ala Asp Ile Leu Ala Pro Pro Glu Val Arg Gly Arg
            20              25              30

Ile Glu Val Ala Val Leu Asn Phe Leu Ala Ala Leu Ala Ser Pro Ser
            35              40              45

Ser Pro Ala Ile Ser Val Leu Pro Leu Ile Ser Arg Ser Ser Ala Asn
        50              55              60

Cys Ser Leu Arg Ser Gly Leu Leu Asn Asp Val Ser Ser Val Tyr Leu
65              70              75              80

Ser Tyr Thr Phe Cys Lys Arg Ser Leu Thr His Asn Pro Lys Ala Phe
                85              90              95

Val Arg Val Trp Lys Val Met Glu Met Cys Tyr Lys Ile Leu Gly Glu
            100             105             110

Gly Lys Leu Ala Gln Gln Arg Glu Leu Phe Tyr Lys Leu Leu Ser Asp
            115             120             125

Ser Pro Lys Tyr Phe Ser Cys Gln Arg His Val Asn Gln Ala Ile Gln
        130             135             140

Asp Val Val Ser Leu Leu Arg Cys Thr Arg Gln Ser Leu Gly Val Met
145             150             155             160

Ala Ser Ser Arg Gly Ala Leu Ile Gly Arg Leu Val Leu His Glu Pro
            165             170             175
```

```
Asp Gly Glu Gln Ile Asp Cys Ser Ile Leu Gly Ala Ser Gly His Ala
            180                 185                 190

Ile Thr Gly Asp Leu Asn Leu Leu Ser Lys Leu Asn Leu Ser Ser Gly
            195                 200                 205

Ser Arg Tyr Ile Ile Val Val Glu Lys Asp Ala Val Phe Gln Arg Leu
            210                 215                 220

Ala Glu Asp Arg Leu Tyr Asn Gln Leu Pro Cys Ile Leu Ile Thr Ala
225                 230                 235                 240

Lys Gly Tyr Pro Asp Ile Ala Thr Arg Phe Ile Leu His Arg Leu Ser
                245                 250                 255

Gln Thr Phe Pro Asn Met Pro Ile Phe Ala Leu Val Asp Trp Asn Pro
            260                 265                 270

Ala Gly Leu Ala Ile Leu Cys Thr Tyr Lys Tyr Gly Ser Ile Ser Met
            275                 280                 285

Gly Leu Glu Ser Tyr Arg Tyr Ala Cys Asn Val Lys Trp Leu Gly Val
            290                 295                 300

Arg Gly Gly Asp Leu His Leu Ile Pro Glu Gly Ala Phe Gln Glu Leu
305                 310                 315                 320

Lys Pro Arg Asp Leu Gln Ile Ala Lys Ser Leu Met Ser Ser Lys Phe
                325                 330                 335

Leu Gln Glu Ser His Arg Ala Glu Leu Ala Leu Met Val Asp Arg Gly
            340                 345                 350

Lys Arg Ala Asp Ile Glu Ala Leu Tyr Ser His Gly Phe Asp Phe Leu
            355                 360                 365

Gly Lys Tyr Ile Ala Arg Lys Ile Val Gln Gly Asp Tyr Ile
    370                 375                 380

<210> SEQ ID NO 49
<211> LENGTH: 219
<212> TYPE: PRT
<213> ORGANISM: Streptococcus thermophilus

<400> SEQUENCE: 49

Met Lys Ile Asn Phe Ser Leu Leu Asp Glu Pro Met Glu Val Asn Leu
1               5                   10                  15

Gly Thr Val Leu Val Ile Glu Asp Val Ser Val Phe Ala Gln Leu Val
            20                  25                  30

Lys Glu Phe Tyr Gln Tyr Asp Glu Gln Ser Asn Leu Thr Ile Phe Asp
            35                  40                  45

Ser Lys Ile Arg Ser Ile Arg Ser Ser Glu Leu Leu Leu Ile Thr Asp
            50                  55                  60

Ile Leu Gly Tyr Asp Ile Asn Thr Ser Gln Val Leu Lys Leu Leu His
65                  70                  75                  80

Thr Asp Ile Val Ser Gln Leu Asn Asp Lys Pro Glu Val Arg Ser Glu
                85                  90                  95

Ile Asp Ser Leu Val Ser Leu Ile Thr Asp Ile Ile Met Ala Glu Cys
            100                 105                 110

Ile Glu Asn Glu Leu Asp Ile Glu Tyr Asp Glu Ile Thr Leu Leu Glu
            115                 120                 125

Leu Ile Lys Ala Leu Gly Val Arg Ile Glu Thr Lys Ser Cys Thr Val
            130                 135                 140

Phe Glu Lys Ile Phe Glu Ile Leu Gln Ile Phe Lys Tyr Leu Val Lys
145                 150                 155                 160

Lys Arg Ile Leu Val Phe Val Asn Ser Leu Ser Tyr Phe Ser Lys Asp
                165                 170                 175
```

```
Glu Ile Tyr Gln Ile Leu Glu Tyr Thr Lys Leu Ser Gln Ala Asp Val
            180                 185                 190

Leu Phe Leu Glu Pro Arg Gln Ile Glu Gly Ile Gln Gln Phe Ile Leu
            195                 200                 205

Asp Lys Asp Tyr Ile Leu Met Pro Tyr Asn Asn
    210                 215

<210> SEQ ID NO 50
<211> LENGTH: 220
<212> TYPE: PRT
<213> ORGANISM: Streptococcus pyogenes

<400> SEQUENCE: 50

Met Asn Leu Asn Phe Ser Leu Leu Asp Glu Pro Ile Pro Leu Arg Gly
1               5                   10                  15

Gly Thr Ile Leu Val Leu Glu Asp Val Cys Val Phe Ser Lys Ile Val
            20                  25                  30

Gln Tyr Cys Tyr Lys Tyr Glu Glu Asp Ser Glu Leu Lys Phe Phe Asp
        35                  40                  45

His Lys Met Lys Thr Ile Lys Glu Ser Glu Ile Met Leu Val Thr Asp
    50                  55                  60

Ile Leu Gly Phe Asp Val Asn Ser Ser Thr Ile Leu Lys Leu Ile His
65                  70                  75                  80

Ala Asp Leu Glu Ser Gln Phe Asn Glu Lys Pro Glu Val Lys Ser Met
            85                  90                  95

Ile Asp Lys Leu Val Ala Thr Ile Thr Glu Leu Ile Val Phe Glu Cys
            100                 105                 110

Leu Glu Asn Glu Leu Asp Leu Glu Tyr Asp Glu Ile Thr Ile Leu Glu
            115                 120                 125

Leu Ile Lys Ser Leu Gly Val Lys Val Glu Thr Gln Ser Asp Thr Ile
    130                 135                 140

Phe Glu Lys Cys Leu Glu Ile Leu Gln Ile Phe Lys Tyr Leu Thr Lys
145                 150                 155                 160

Lys Lys Leu Val Val Phe Val Asn Ser Gly Ala Phe Leu Thr Lys Glu
            165                 170                 175

Glu Val Ala Ser Leu Gln Glu Tyr Ile Ser Leu Thr Asn Leu Thr Val
            180                 185                 190

Leu Phe Leu Glu Pro Arg Glu Leu Tyr Asp Phe Pro Gln Tyr Ile Leu
            195                 200                 205

Asp Glu Asp Tyr Phe Leu Ile Thr Lys Asn Met Val
    210                 215                 220

<210> SEQ ID NO 51
<211> LENGTH: 221
<212> TYPE: PRT
<213> ORGANISM: Streptococcus canis

<400> SEQUENCE: 51

Met Val Met Leu Asn Phe Glu Leu Leu Asp Asn Pro Leu Thr Ile Glu
1               5                   10                  15

Lys Met Thr Thr Leu Val Ile Lys Asp Val Asn Val Phe Ser Ser Phe
            20                  25                  30

Val Arg Gln Cys Tyr Gln Tyr Gly Glu Thr Asn Asp Leu Gln Ile Phe
        35                  40                  45

Asp Thr Lys Leu Lys Ala Leu Lys Val Ser Glu Val Met Leu Ile Thr
    50                  55                  60
```

```
Asp Ile Leu Gly Tyr Asp Ile Asn Ser Pro Ser Ile Leu Lys Met Ile
65                  70                  75                  80

His Ala Asp Leu Glu Asp Cys Phe Asn Ser Gln Pro Glu Val Lys Ser
                85                  90                  95

Met Ile Glu Lys Leu Ala Ala Thr Ile Thr Glu Leu Ile Ala Tyr Glu
                100                 105                 110

Cys Leu Glu Asn Glu Leu Asp Leu Glu Tyr Asp Glu Ile Thr Ile Leu
                115                 120                 125

Glu Leu Ile Lys Ala Leu Gly Val Lys Val Glu Thr Gln Ser Asp Thr
    130                 135                 140

Ile Phe Glu Lys Cys Leu Glu Ile Leu Gln Val Phe Lys Tyr Leu Ser
145                 150                 155                 160

Lys Lys Lys Leu Leu Ile Phe Ile Asn Cys Gly Ser Tyr Leu Thr Lys
                165                 170                 175

Glu Glu Leu Leu Lys Ile Arg Glu Tyr Ile Asp Leu Ser Gln Gln Arg
                180                 185                 190

Val Leu Phe Ile Glu Pro Arg Lys Leu Tyr Asn Ile Pro Gln Tyr Ile
    195                 200                 205

Leu Asp Glu Asp Tyr Phe Leu Ile Lys Glu His Thr Thr
    210                 215                 220
```

```
<210> SEQ ID NO 52
<211> LENGTH: 1285
<212> TYPE: PRT
<213> ORGANISM: Herbinix hemicellulosilytica

<400> SEQUENCE: 52
```

```
Met Lys Leu Thr Arg Arg Ile Ser Gly Asn Ser Val Asp Gln Lys
1               5                   10                  15

Ile Thr Ala Ala Phe Tyr Arg Asp Met Ser Gln Gly Leu Leu Tyr Tyr
                20                  25                  30

Asp Ser Glu Asp Asn Asp Cys Thr Asp Lys Val Ile Glu Ser Met Asp
        35                  40                  45

Phe Glu Arg Ser Trp Arg Gly Arg Ile Leu Lys Asn Gly Glu Asp Asp
    50                  55                  60

Lys Asn Pro Phe Tyr Met Phe Val Lys Gly Leu Val Gly Ser Asn Asp
65                  70                  75                  80

Lys Ile Val Cys Glu Pro Ile Asp Val Asp Ser Asp Pro Asp Asn Leu
                85                  90                  95

Asp Ile Leu Ile Asn Lys Asn Leu Thr Gly Phe Gly Arg Asn Leu Lys
                100                 105                 110

Ala Pro Asp Ser Asn Asp Thr Leu Glu Asn Leu Ile Arg Lys Ile Gln
                115                 120                 125

Ala Gly Ile Pro Glu Glu Glu Val Leu Pro Glu Leu Lys Lys Ile Lys
    130                 135                 140

Glu Met Ile Gln Lys Asp Ile Val Asn Arg Lys Glu Gln Leu Leu Lys
145                 150                 155                 160

Ser Ile Lys Asn Asn Arg Ile Pro Phe Ser Leu Glu Gly Ser Lys Leu
                165                 170                 175

Val Pro Ser Thr Lys Lys Met Lys Trp Leu Phe Lys Leu Ile Asp Val
                180                 185                 190

Pro Asn Lys Thr Phe Asn Glu Lys Met Leu Glu Lys Tyr Trp Glu Ile
    195                 200                 205

Tyr Asp Tyr Asp Lys Leu Lys Ala Asn Ile Thr Asn Arg Leu Asp Lys
```

-continued

```
          210                215                220

Thr Asp Lys Lys Ala Arg Ser Ile Ser Arg Ala Val Ser Glu Glu Leu
225                230                235                240

Arg Glu Tyr His Lys Asn Leu Arg Thr Asn Tyr Asn Arg Phe Val Ser
              245                250                255

Gly Asp Arg Pro Ala Ala Gly Leu Asp Asn Gly Gly Ser Ala Lys Tyr
              260                265                270

Asn Pro Asp Lys Glu Glu Phe Leu Leu Phe Leu Lys Glu Val Glu Gln
              275                280                285

Tyr Phe Lys Lys Tyr Phe Pro Val Lys Ser Lys His Ser Asn Lys Ser
              290                295                300

Lys Asp Lys Ser Leu Val Asp Lys Tyr Lys Asn Tyr Cys Ser Tyr Lys
305                310                315                320

Val Val Lys Lys Glu Val Asn Arg Ser Ile Ile Asn Gln Leu Val Ala
              325                330                335

Gly Leu Ile Gln Gln Gly Lys Leu Leu Tyr Tyr Phe Tyr Tyr Asn Asp
              340                345                350

Thr Trp Gln Glu Asp Phe Leu Asn Ser Tyr Gly Leu Ser Tyr Ile Gln
              355                360                365

Val Glu Glu Ala Phe Lys Lys Ser Val Met Thr Ser Leu Ser Trp Gly
              370                375                380

Ile Asn Arg Leu Thr Ser Phe Phe Ile Asp Asp Ser Asn Thr Val Lys
385                390                395                400

Phe Asp Asp Ile Thr Thr Lys Lys Ala Lys Glu Ala Ile Glu Ser Asn
              405                410                415

Tyr Phe Asn Lys Leu Arg Thr Cys Ser Arg Met Gln Asp His Phe Lys
              420                425                430

Glu Lys Leu Ala Phe Phe Tyr Pro Val Tyr Val Lys Asp Lys Lys Asp
              435                440                445

Arg Pro Asp Asp Asp Ile Glu Asn Leu Ile Val Leu Val Lys Asn Ala
              450                455                460

Ile Glu Ser Val Ser Tyr Leu Arg Asn Arg Thr Phe His Phe Lys Glu
465                470                475                480

Ser Ser Leu Leu Glu Leu Leu Lys Glu Leu Asp Asp Lys Asn Ser Gly
              485                490                495

Gln Asn Lys Ile Asp Tyr Ser Val Ala Ala Glu Phe Ile Lys Arg Asp
              500                505                510

Ile Glu Asn Leu Tyr Asp Val Phe Arg Glu Gln Ile Arg Ser Leu Gly
              515                520                525

Ile Ala Glu Tyr Tyr Lys Ala Asp Met Ile Ser Asp Cys Phe Lys Thr
              530                535                540

Cys Gly Leu Glu Phe Ala Leu Tyr Ser Pro Lys Asn Ser Leu Met Pro
545                550                555                560

Ala Phe Lys Asn Val Tyr Lys Arg Gly Ala Asn Leu Asn Lys Ala Tyr
              565                570                575

Ile Arg Asp Lys Gly Pro Lys Glu Thr Gly Asp Gln Gly Gln Asn Ser
              580                585                590

Tyr Lys Ala Leu Glu Glu Tyr Arg Glu Leu Thr Trp Tyr Ile Glu Val
              595                600                605

Lys Asn Asn Asp Gln Ser Tyr Asn Ala Tyr Lys Asn Leu Leu Gln Leu
              610                615                620

Ile Tyr Tyr His Ala Phe Leu Pro Glu Val Arg Glu Asn Glu Ala Leu
625                630                635                640
```

```
Ile Thr Asp Phe Ile Asn Arg Thr Lys Glu Trp Asn Arg Lys Glu Thr
            645                 650                 655

Glu Glu Arg Leu Asn Thr Lys Asn Asn Lys Lys His Lys Asn Phe Asp
            660                 665                 670

Glu Asn Asp Asp Ile Thr Val Asn Thr Tyr Arg Tyr Glu Ser Ile Pro
            675                 680                 685

Asp Tyr Gln Gly Glu Ser Leu Asp Asp Tyr Leu Lys Val Leu Gln Arg
        690                 695                 700

Lys Gln Met Ala Arg Ala Lys Glu Val Asn Glu Lys Glu Glu Gly Asn
705                 710                 715                 720

Asn Asn Tyr Ile Gln Phe Ile Arg Asp Val Val Val Trp Ala Phe Gly
            725                 730                 735

Ala Tyr Leu Glu Asn Lys Leu Lys Asn Tyr Lys Asn Glu Leu Gln Pro
            740                 745                 750

Pro Leu Ser Lys Glu Asn Ile Gly Leu Asn Asp Thr Leu Lys Glu Leu
            755                 760                 765

Phe Pro Glu Glu Lys Val Lys Ser Pro Phe Asn Ile Lys Cys Arg Phe
        770                 775                 780

Ser Ile Ser Thr Phe Ile Asp Asn Lys Gly Lys Ser Thr Asp Asn Thr
785                 790                 795                 800

Ser Ala Glu Ala Val Lys Thr Asp Gly Lys Glu Asp Glu Lys Asp Lys
            805                 810                 815

Lys Asn Ile Lys Arg Lys Asp Leu Leu Cys Phe Tyr Leu Phe Leu Arg
            820                 825                 830

Leu Leu Asp Glu Asn Glu Ile Cys Lys Leu Gln His Gln Phe Ile Lys
            835                 840                 845

Tyr Arg Cys Ser Leu Lys Glu Arg Arg Phe Pro Gly Asn Arg Thr Lys
        850                 855                 860

Leu Glu Lys Glu Thr Glu Leu Leu Ala Glu Leu Glu Glu Leu Met Glu
865                 870                 875                 880

Leu Val Arg Phe Thr Met Pro Ser Ile Pro Glu Ile Ser Ala Lys Ala
            885                 890                 895

Glu Ser Gly Tyr Asp Thr Met Ile Lys Lys Tyr Phe Lys Asp Phe Ile
            900                 905                 910

Glu Lys Lys Val Phe Lys Asn Pro Lys Thr Ser Asn Leu Tyr Tyr His
            915                 920                 925

Ser Asp Ser Lys Thr Pro Val Thr Arg Lys Tyr Met Ala Leu Leu Met
        930                 935                 940

Arg Ser Ala Pro Leu His Leu Tyr Lys Asp Ile Phe Lys Gly Tyr Tyr
945                 950                 955                 960

Leu Ile Thr Lys Lys Glu Cys Leu Glu Tyr Ile Lys Leu Ser Asn Ile
            965                 970                 975

Ile Lys Asp Tyr Gln Asn Ser Leu Asn Glu Leu His Glu Gln Leu Glu
            980                 985                 990

Arg Ile Lys Leu Lys Ser Glu Lys  Gln Asn Gly Lys Asp  Ser Leu Tyr
            995                 1000                1005

Leu Asp  Lys Lys Asp Phe Tyr  Lys Val Lys Glu Tyr  Val Glu Asn
    1010                1015                1020

Leu Glu  Gln Val Ala Arg Tyr  Lys His Leu Gln His  Lys Ile Asn
    1025                1030                1035

Phe Glu  Ser Leu Tyr Arg Ile  Phe Arg Ile His Val  Asp Ile Ala
    1040                1045                1050
```

```
Ala Arg Met Val Gly Tyr Thr  Gln Asp Trp Glu Arg  Asp Met His
    1055             1060              1065

Phe Leu Phe Lys Ala Leu Val  Tyr Asn Gly Val Leu  Glu Glu Arg
    1070             1075              1080

Arg Phe Glu Ala Ile Phe Asn  Asn Asn Asp Asp Asn  Asn Asp Gly
    1085             1090              1095

Arg Ile Val Lys Lys Ile Gln  Asn Asn Leu Asn Asn  Lys Asn Arg
    1100             1105              1110

Glu Leu Val Ser Met Leu Cys  Trp Asn Lys Lys Leu  Asn Lys Asn
    1115             1120              1125

Glu Phe Gly Ala Ile Ile Trp  Lys Arg Asn Pro Ile  Ala His Leu
    1130             1135              1140

Asn His Phe Thr Gln Thr Glu  Gln Asn Ser Lys Ser  Ser Leu Glu
    1145             1150              1155

Ser Leu Ile Asn Ser Leu Arg  Ile Leu Leu Ala Tyr  Asp Arg Lys
    1160             1165              1170

Arg Gln Asn Ala Val Thr Lys  Thr Ile Asn Asp Leu  Leu Leu Asn
    1175             1180              1185

Asp Tyr His Ile Arg Ile Lys  Trp Glu Gly Arg Val  Asp Glu Gly
    1190             1195              1200

Gln Ile Tyr Phe Asn Ile Lys  Glu Lys Glu Asp Ile  Glu Asn Glu
    1205             1210              1215

Pro Ile Ile His Leu Lys His  Leu His Lys Lys Asp  Cys Tyr Ile
    1220             1225              1230

Tyr Lys Asn Ser Tyr Met Phe  Asp Lys Gln Lys Glu  Trp Ile Cys
    1235             1240              1245

Asn Gly Ile Lys Glu Glu Val  Tyr Asp Lys Ser Ile  Leu Lys Cys
    1250             1255              1260

Ile Gly Asn Leu Phe Lys Phe  Asp Tyr Glu Asp Lys  Asn Lys Ser
    1265             1270              1275

Ser Ala Asn Pro Lys His Thr
    1280             1285
```

<210> SEQ ID NO 53
<211> LENGTH: 1437
<212> TYPE: PRT
<213> ORGANISM: Lachnospiraceae bacterium

<400> SEQUENCE: 53

```
Met Lys Ile Ser Lys Val Arg  Glu Glu Asn Arg Gly  Ala Lys Leu Thr
1                5                 10                15

Val Asn Ala Lys Thr Ala Val  Val Ser Glu Asn Arg  Ser Gln Glu Gly
            20                25                30

Ile Leu Tyr Asn Asp Pro Ser  Arg Tyr Gly Lys Ser  Arg Lys Asn Asp
            35                40                45

Glu Asp Arg Asp Arg Tyr Ile  Glu Ser Arg Leu Lys  Ser Ser Gly Lys
    50                55                60

Leu Tyr Arg Ile Phe Asn Glu  Asp Lys Asn Lys Arg  Glu Thr Asp Glu
65                70                75                80

Leu Gln Trp Phe Leu Ser Glu  Ile Val Lys Lys Ile  Asn Arg Arg Asn
            85                90                95

Gly Leu Val Leu Ser Asp Met  Leu Ser Val Asp Asp  Arg Ala Phe Glu
            100               105               110

Lys Ala Phe Glu Lys Tyr Ala  Glu Leu Ser Tyr Thr  Asn Arg Arg Asn
            115               120               125
```

```
Lys Val Ser Gly Ser Pro Ala Phe Glu Thr Cys Gly Val Asp Ala Ala
    130                 135                 140

Thr Ala Glu Arg Leu Lys Gly Ile Ile Ser Glu Thr Asn Phe Ile Asn
145                 150                 155                 160

Arg Ile Lys Asn Asn Ile Asp Asn Lys Val Ser Glu Asp Ile Ile Asp
                165                 170                 175

Arg Ile Ile Ala Lys Tyr Leu Lys Lys Ser Leu Cys Arg Glu Arg Val
                180                 185                 190

Lys Arg Gly Leu Lys Lys Leu Leu Met Asn Ala Phe Asp Leu Pro Tyr
            195                 200                 205

Ser Asp Pro Asp Ile Asp Val Gln Arg Asp Phe Ile Asp Tyr Val Leu
    210                 215                 220

Glu Asp Phe Tyr His Val Arg Ala Lys Ser Gln Val Ser Arg Ser Ile
225                 230                 235                 240

Lys Asn Met Asn Met Pro Val Gln Pro Glu Gly Asp Gly Lys Phe Ala
                245                 250                 255

Ile Thr Val Ser Lys Gly Gly Thr Glu Ser Gly Asn Lys Arg Ser Ala
            260                 265                 270

Glu Lys Glu Ala Phe Lys Lys Phe Leu Ser Asp Tyr Ala Ser Leu Asp
        275                 280                 285

Glu Arg Val Arg Asp Asp Met Leu Arg Arg Met Arg Arg Leu Val Val
    290                 295                 300

Leu Tyr Phe Tyr Gly Ser Asp Asp Ser Lys Leu Ser Asp Val Asn Glu
305                 310                 315                 320

Lys Phe Asp Val Trp Glu Asp His Ala Ala Arg Arg Val Asp Asn Arg
                325                 330                 335

Glu Phe Ile Lys Leu Pro Leu Glu Asn Lys Leu Ala Asn Gly Lys Thr
            340                 345                 350

Asp Lys Asp Ala Glu Arg Ile Arg Lys Asn Thr Val Lys Glu Leu Tyr
        355                 360                 365

Arg Asn Gln Asn Ile Gly Cys Tyr Arg Gln Ala Val Lys Ala Val Glu
    370                 375                 380

Glu Asp Asn Asn Gly Arg Tyr Phe Asp Asp Lys Met Leu Asn Met Phe
385                 390                 395                 400

Phe Ile His Arg Ile Glu Tyr Gly Val Glu Lys Ile Tyr Ala Asn Leu
            405                 410                 415

Lys Gln Val Thr Glu Phe Lys Ala Arg Thr Gly Tyr Leu Ser Glu Lys
            420                 425                 430

Ile Trp Lys Asp Leu Ile Asn Tyr Ile Ser Ile Lys Tyr Ile Ala Met
            435                 440                 445

Gly Lys Ala Val Tyr Asn Tyr Ala Met Asp Glu Leu Asn Ala Ser Asp
    450                 455                 460

Lys Lys Glu Ile Glu Leu Gly Lys Ile Ser Glu Glu Tyr Leu Ser Gly
465                 470                 475                 480

Ile Ser Ser Phe Asp Tyr Glu Leu Ile Lys Ala Glu Glu Met Leu Gln
            485                 490                 495

Arg Glu Thr Ala Val Tyr Val Ala Phe Ala Ala Arg His Leu Ser Ser
            500                 505                 510

Gln Thr Val Glu Leu Asp Ser Glu Asn Ser Asp Phe Leu Leu Leu Lys
            515                 520                 525

Pro Lys Gly Thr Met Asp Lys Asn Asp Lys Asn Lys Leu Ala Ser Asn
    530                 535                 540
```

-continued

```
Asn Ile Leu Asn Phe Leu Lys Asp Lys Glu Thr Leu Arg Asp Thr Ile
545                 550                 555                 560

Leu Gln Tyr Phe Gly Gly His Ser Leu Trp Thr Asp Phe Pro Phe Asp
                565                 570                 575

Lys Tyr Leu Ala Gly Gly Lys Asp Asp Val Asp Phe Leu Thr Asp Leu
                580                 585                 590

Lys Asp Val Ile Tyr Ser Met Arg Asn Asp Ser Phe His Tyr Ala Thr
                595                 600                 605

Glu Asn His Asn Asn Gly Lys Trp Asn Lys Glu Leu Ile Ser Ala Met
    610                 615                 620

Phe Glu His Glu Thr Glu Arg Met Thr Val Val Met Lys Asp Lys Phe
625                 630                 635                 640

Tyr Ser Asn Asn Leu Pro Met Phe Tyr Lys Asn Asp Asp Leu Lys Lys
                645                 650                 655

Leu Leu Ile Asp Leu Tyr Lys Asp Asn Val Glu Arg Ala Ser Gln Val
                660                 665                 670

Pro Ser Phe Asn Lys Val Phe Val Arg Lys Asn Phe Pro Ala Leu Val
                675                 680                 685

Arg Asp Lys Asp Asn Leu Gly Ile Glu Leu Asp Leu Lys Ala Asp Ala
    690                 695                 700

Asp Lys Gly Glu Asn Glu Leu Lys Phe Tyr Asn Ala Leu Tyr Tyr Met
705                 710                 715                 720

Phe Lys Glu Ile Tyr Tyr Asn Ala Phe Leu Asn Asp Lys Asn Val Arg
                725                 730                 735

Glu Arg Phe Ile Thr Lys Ala Thr Lys Val Ala Asp Asn Tyr Asp Arg
                740                 745                 750

Asn Lys Glu Arg Asn Leu Lys Asp Arg Ile Lys Ser Ala Gly Ser Asp
                755                 760                 765

Glu Lys Lys Lys Leu Arg Glu Gln Leu Gln Asn Tyr Ile Ala Glu Asn
    770                 775                 780

Asp Phe Gly Gln Arg Ile Lys Asn Ile Val Gln Val Asn Pro Asp Tyr
785                 790                 795                 800

Thr Leu Ala Gln Ile Cys Gln Leu Ile Met Thr Glu Tyr Asn Gln Gln
                805                 810                 815

Asn Asn Gly Cys Met Gln Lys Lys Ser Ala Ala Arg Lys Asp Ile Asn
                820                 825                 830

Lys Asp Ser Tyr Gln His Tyr Lys Met Leu Leu Leu Val Asn Leu Arg
                835                 840                 845

Lys Ala Phe Leu Glu Phe Ile Lys Glu Asn Tyr Ala Phe Val Leu Lys
    850                 855                 860

Pro Tyr Lys His Asp Leu Cys Asp Lys Ala Asp Phe Val Pro Asp Phe
865                 870                 875                 880

Ala Lys Tyr Val Lys Pro Tyr Ala Gly Leu Ile Ser Arg Val Ala Gly
                885                 890                 895

Ser Ser Glu Leu Gln Lys Trp Tyr Ile Val Ser Arg Phe Leu Ser Pro
                900                 905                 910

Ala Gln Ala Asn His Met Leu Gly Phe Leu His Ser Tyr Lys Gln Tyr
                915                 920                 925

Val Trp Asp Ile Tyr Arg Arg Ala Ser Glu Thr Gly Thr Glu Ile Asn
    930                 935                 940

His Ser Ile Ala Glu Asp Lys Ile Ala Gly Val Asp Ile Thr Asp Val
945                 950                 955                 960

Asp Ala Val Ile Asp Leu Ser Val Lys Leu Cys Gly Thr Ile Ser Ser
```

-continued

```
                  965              970                    975

Glu Ile Ser Asp Tyr Phe Lys Asp Asp Glu Val Tyr Ala Glu Tyr Ile
              980                  985                    990

Ser Ser Tyr Leu Asp Phe Glu Tyr  Asp Gly Gly Asn Tyr  Lys Asp Ser
          995              1000                    1005

Leu Asn  Arg Phe Cys Asn Ser  Asp Ala Val Asn Asp  Gln Lys Val
    1010              1015                    1020

Ala Leu  Tyr Tyr Asp Gly Glu  His Pro Lys Leu Asn  Arg Asn Ile
    1025              1030                    1035

Ile Leu  Ser Lys Leu Tyr Gly  Glu Arg Arg Phe Leu  Glu Lys Ile
    1040              1045                    1050

Thr Asp  Arg Val Ser Arg Ser  Asp Ile Val Glu Tyr  Tyr Lys Leu
    1055              1060                    1065

Lys Lys  Glu Thr Ser Gln Tyr  Gln Thr Lys Gly Ile  Phe Asp Ser
    1070              1075                    1080

Glu Asp  Glu Gln Lys Asn Ile  Lys Lys Phe Gln Glu  Met Lys Asn
    1085              1090                    1095

Ile Val  Glu Phe Arg Asp Leu  Met Asp Tyr Ser Glu  Ile Ala Asp
    1100              1105                    1110

Glu Leu  Gln Gly Gln Leu Ile  Asn Trp Ile Tyr Leu  Arg Glu Arg
    1115              1120                    1125

Asp Leu  Met Asn Phe Gln Leu  Gly Tyr His Tyr Ala  Cys Leu Asn
    1130              1135                    1140

Asn Asp  Ser Asn Lys Gln Ala  Thr Tyr Val Thr Leu  Asp Tyr Gln
    1145              1150                    1155

Gly Lys  Lys Asn Arg Lys Ile  Asn Gly Ala Ile Leu  Tyr Gln Ile
    1160              1165                    1170

Cys Ala  Met Tyr Ile Asn Gly  Leu Pro Leu Tyr Tyr  Val Asp Lys
    1175              1180                    1185

Asp Ser  Ser Glu Trp Thr Val  Ser Asp Gly Lys Glu  Ser Thr Gly
    1190              1195                    1200

Ala Lys  Ile Gly Glu Phe Tyr  Arg Tyr Ala Lys Ser  Phe Glu Asn
    1205              1210                    1215

Thr Ser  Asp Cys Tyr Ala Ser  Gly Leu Glu Ile Phe  Glu Asn Ile
    1220              1225                    1230

Ser Glu  His Asp Asn Ile Thr  Glu Leu Arg Asn Tyr  Ile Glu His
    1235              1240                    1245

Phe Arg  Tyr Tyr Ser Ser Phe  Asp Arg Ser Phe Leu  Gly Ile Tyr
    1250              1255                    1260

Ser Glu  Val Phe Asp Arg Phe  Phe Thr Tyr Asp Leu  Lys Tyr Arg
    1265              1270                    1275

Lys Asn  Val Pro Thr Ile Leu  Tyr Asn Ile Leu Leu  Gln His Phe
    1280              1285                    1290

Val Asn  Val Arg Phe Glu Phe  Val Ser Gly Lys Lys  Met Ile Gly
    1295              1300                    1305

Ile Asp  Lys Lys Asp Arg Lys  Ile Ala Lys Glu Lys  Glu Cys Ala
    1310              1315                    1320

Arg Ile  Thr Ile Arg Glu Lys  Asn Gly Val Tyr Ser  Glu Gln Phe
    1325              1330                    1335

Thr Tyr  Lys Leu Lys Asn Gly  Thr Val Tyr Val Asp  Ala Arg Asp
    1340              1345                    1350

Lys Arg  Tyr Leu Gln Ser Ile  Ile Arg Leu Leu Phe  Tyr Pro Glu
    1355              1360                    1365
```

```
Lys Val  Asn Met Asp Glu Met  Ile Glu Val Lys Glu  Lys Lys Lys
    1370             1375              1380

Pro Ser  Asp Asn Asn Thr Gly  Lys Gly Tyr Ser Lys  Arg Asp Arg
    1385             1390              1395

Gln Gln  Asp Arg Lys Glu Tyr  Asp Lys Tyr Lys Glu  Lys Lys Lys
    1400             1405              1410

Lys Glu  Gly Asn Phe Leu Ser  Gly Met Gly Gly Asn  Ile Asn Trp
    1415             1420              1425

Asp Glu  Ile Asn Ala Gln Leu  Lys Asn
    1430             1435

<210> SEQ ID NO 54
<211> LENGTH: 1182
<212> TYPE: PRT
<213> ORGANISM: Leptotrichia wadei

<400> SEQUENCE: 54

Met Tyr Met Lys Ile Thr Lys Ile Asp Gly Val Ser His Tyr Lys Lys
1               5                   10                  15

Gln Asp Lys Gly Ile Leu Lys Lys Lys Trp Lys Asp Leu Asp Glu Arg
            20                  25                  30

Lys Gln Arg Glu Lys Ile Glu Ala Arg Tyr Asn Lys Gln Ile Glu Ser
        35                  40                  45

Lys Ile Tyr Lys Glu Phe Phe Arg Leu Lys Asn Lys Lys Arg Ile Glu
    50                  55                  60

Lys Glu Glu Asp Gln Asn Ile Lys Ser Leu Tyr Phe Phe Ile Lys Glu
65                  70                  75                  80

Leu Tyr Leu Asn Glu Lys Asn Glu Glu Trp Glu Leu Lys Asn Ile Asn
                85                  90                  95

Leu Glu Ile Leu Asp Asp Lys Glu Arg Val Ile Lys Gly Tyr Lys Phe
            100                 105                 110

Lys Glu Asp Val Tyr Phe Phe Lys Glu Gly Tyr Lys Glu Tyr Tyr Leu
        115                 120                 125

Arg Ile Leu Phe Asn Asn Leu Ile Glu Lys Val Gln Asn Glu Asn Arg
    130                 135                 140

Glu Lys Val Arg Lys Asn Lys Glu Phe Leu Asp Leu Lys Glu Ile Phe
145                 150                 155                 160

Lys Lys Tyr Lys Asn Arg Lys Ile Asp Leu Leu Leu Lys Ser Ile Asn
                165                 170                 175

Asn Asn Lys Ile Asn Leu Glu Tyr Lys Lys Glu Asn Val Asn Glu Glu
            180                 185                 190

Ile Tyr Gly Ile Asn Pro Thr Asn Asp Arg Glu Met Thr Phe Tyr Glu
        195                 200                 205

Leu Leu Lys Glu Ile Ile Glu Lys Lys Asp Glu Gln Lys Ser Ile Leu
    210                 215                 220

Glu Glu Lys Leu Asp Asn Phe Asp Ile Thr Asn Phe Leu Glu Asn Ile
225                 230                 235                 240

Glu Lys Ile Phe Asn Glu Glu Thr Glu Ile Asn Ile Ile Lys Gly Lys
                245                 250                 255

Val Leu Asn Glu Leu Arg Glu Tyr Ile Lys Glu Lys Glu Glu Asn Asn
            260                 265                 270

Ser Asp Asn Lys Leu Lys Gln Ile Tyr Asn Leu Glu Leu Lys Lys Tyr
        275                 280                 285

Ile Glu Asn Asn Phe Ser Tyr Lys Lys Gln Lys Ser Lys Ser Lys Asn
```

-continued

```
            290              295              300

Gly Lys Asn Asp Tyr Leu Tyr Leu Asn Phe Leu Lys Lys Ile Met Phe
305              310              315              320

Ile Glu Glu Val Asp Glu Lys Lys Glu Ile Asn Lys Glu Lys Phe Lys
                 325              330              335

Asn Lys Ile Asn Ser Asn Phe Lys Asn Leu Phe Val Gln His Ile Leu
                 340              345              350

Asp Tyr Gly Lys Leu Leu Tyr Tyr Lys Glu Asn Asp Glu Tyr Ile Lys
                 355              360              365

Asn Thr Gly Gln Leu Glu Thr Lys Asp Leu Glu Tyr Ile Lys Thr Lys
                 370              375              380

Glu Thr Leu Ile Arg Lys Met Ala Val Leu Val Ser Phe Ala Ala Asn
385              390              395              400

Ser Tyr Tyr Asn Leu Phe Gly Arg Val Ser Gly Asp Ile Leu Gly Thr
                 405              410              415

Glu Val Val Lys Ser Ser Lys Thr Asn Val Ile Lys Val Gly Ser His
                 420              425              430

Ile Phe Lys Glu Lys Met Leu Asn Tyr Phe Phe Asp Phe Glu Ile Phe
                 435              440              445

Asp Ala Asn Lys Ile Val Glu Ile Leu Glu Ser Ile Ser Tyr Ser Ile
     450              455              460

Tyr Asn Val Arg Asn Gly Val Gly His Phe Asn Lys Leu Ile Leu Gly
465              470              475              480

Lys Tyr Lys Lys Lys Asp Ile Asn Thr Asn Lys Arg Ile Glu Glu Asp
                 485              490              495

Leu Asn Asn Asn Glu Glu Ile Lys Gly Tyr Phe Ile Lys Lys Arg Gly
                 500              505              510

Glu Ile Glu Arg Lys Val Lys Glu Lys Phe Leu Ser Asn Asn Leu Gln
                 515              520              525

Tyr Tyr Tyr Ser Lys Glu Lys Ile Glu Asn Tyr Phe Glu Val Tyr Glu
                 530              535              540

Phe Glu Ile Leu Lys Arg Lys Ile Pro Phe Ala Pro Asn Phe Lys Arg
545              550              555              560

Ile Ile Lys Lys Gly Glu Asp Leu Phe Asn Asn Lys Asn Asn Lys Lys
                 565              570              575

Tyr Glu Tyr Phe Lys Asn Phe Asp Lys Asn Ser Ala Glu Glu Lys Lys
                 580              585              590

Glu Phe Leu Lys Thr Arg Asn Phe Leu Leu Lys Glu Leu Tyr Tyr Asn
                 595              600              605

Asn Phe Tyr Lys Glu Phe Leu Ser Lys Lys Glu Glu Phe Glu Lys Ile
     610              615              620

Val Leu Glu Val Lys Glu Glu Lys Lys Ser Arg Gly Asn Ile Asn Asn
625              630              635              640

Lys Lys Ser Gly Val Ser Phe Gln Ser Ile Asp Asp Tyr Asp Thr Lys
                 645              650              655

Ile Asn Ile Ser Asp Tyr Ile Ala Ser Ile His Lys Lys Glu Met Glu
                 660              665              670

Arg Val Glu Lys Tyr Asn Glu Glu Lys Gln Lys Asp Thr Ala Lys Tyr
                 675              680              685

Ile Arg Asp Phe Val Glu Glu Ile Phe Leu Thr Gly Phe Ile Asn Tyr
     690              695              700

Leu Glu Lys Asp Lys Arg Leu His Phe Leu Lys Glu Glu Phe Ser Ile
705              710              715              720
```

-continued

```
Leu Cys Asn Asn Asn Asn Asn Val Val Asp Phe Asn Ile Asn Ile Asn
            725                 730                 735

Glu Glu Lys Ile Lys Glu Phe Leu Lys Glu Asn Asp Ser Lys Thr Leu
            740                 745                 750

Asn Leu Tyr Leu Phe Phe Asn Met Ile Asp Ser Lys Arg Ile Ser Glu
            755                 760                 765

Phe Arg Asn Glu Leu Val Lys Tyr Lys Gln Phe Thr Lys Lys Arg Leu
    770                 775                 780

Asp Glu Glu Lys Glu Phe Leu Gly Ile Lys Ile Glu Leu Tyr Glu Thr
785                 790                 795                 800

Leu Ile Glu Phe Val Ile Leu Thr Arg Glu Lys Leu Asp Thr Lys Lys
            805                 810                 815

Ser Glu Glu Ile Asp Ala Trp Leu Val Asp Lys Leu Tyr Val Lys Asp
            820                 825                 830

Ser Asn Glu Tyr Lys Glu Tyr Glu Glu Ile Leu Lys Leu Phe Val Asp
            835                 840                 845

Glu Lys Ile Leu Ser Ser Lys Glu Ala Pro Tyr Tyr Ala Thr Asp Asn
    850                 855                 860

Lys Thr Pro Ile Leu Leu Ser Asn Phe Glu Lys Thr Arg Lys Tyr Gly
865                 870                 875                 880

Thr Gln Ser Phe Leu Ser Glu Ile Gln Ser Asn Tyr Lys Tyr Ser Lys
            885                 890                 895

Val Glu Lys Glu Asn Ile Glu Asp Tyr Asn Lys Lys Glu Glu Ile Glu
            900                 905                 910

Gln Lys Lys Lys Ser Asn Ile Glu Lys Leu Gln Asp Leu Lys Val Glu
            915                 920                 925

Leu His Lys Lys Trp Glu Gln Asn Lys Ile Thr Glu Lys Glu Ile Glu
    930                 935                 940

Lys Tyr Asn Asn Thr Thr Arg Lys Ile Asn Glu Tyr Asn Tyr Leu Lys
945                 950                 955                 960

Asn Lys Glu Glu Leu Gln Asn Val Tyr Leu Leu His Glu Met Leu Ser
            965                 970                 975

Asp Leu Leu Ala Arg Asn Val Ala Phe Phe Asn Lys Trp Glu Arg Asp
            980                 985                 990

Phe Lys Phe Ile Val Ile Ala Ile  Lys Gln Phe Leu Arg  Glu Asn Asp
    995                 1000                1005

Lys Glu  Lys Val Asn Glu Phe  Leu Asn Pro Pro Asp  Asn Ser Lys
    1010                1015                1020

Gly Lys  Lys Val Tyr Phe Ser  Val Ser Lys Tyr Lys  Asn Thr Val
    1025                1030                1035

Glu Asn  Ile Asp Gly Ile His  Lys Asn Phe Met Asn  Leu Ile Phe
    1040                1045                1050

Leu Asn  Asn Lys Phe Met Asn  Arg Lys Ile Asp Lys  Met Asn Cys
    1055                1060                1065

Ala Ile  Trp Val Tyr Phe Arg  Asn Tyr Ile Ala His  Phe Leu His
    1070                1075                1080

Leu His  Thr Lys Asn Glu Lys  Ile Ser Leu Ile Ser  Gln Met Asn
    1085                1090                1095

Leu Leu  Ile Lys Leu Phe Ser  Tyr Asp Lys Lys Val  Gln Asn His
    1100                1105                1110

Ile Leu  Lys Ser Thr Lys Thr  Leu Leu Glu Lys Tyr  Asn Ile Gln
    1115                1120                1125
```

```
Ile Asn  Phe Glu Ile Ser Asn  Asp Lys Asn Glu Val  Phe Lys Tyr
    1130             1135             1140

Lys Ile  Lys Asn Arg Leu Tyr  Ser Lys Lys Gly Lys  Met Leu Gly
    1145             1150             1155

Lys Asn  Asn Lys Phe Glu Ile  Leu Glu Asn Glu Phe  Leu Glu Asn
    1160             1165             1170

Val Lys  Ala Met Leu Glu Tyr  Ser Glu
    1175             1180
```